US011266768B2

(12) United States Patent
Grinstaff et al.

(10) Patent No.: US 11,266,768 B2
(45) Date of Patent: Mar. 8, 2022

(54) STRETCH RELEASE DRUG DELIVERY MATERIALS

(71) Applicant: TRUSTEES OF BOSTON UNIVERSITY, Boston, MA (US)

(72) Inventors: Mark Grinstaff, Brookline, MA (US); Jonah Andrew Kaplan, Newton, MA (US); Julia Wang, Forest Hills, NY (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/039,136

(22) PCT Filed: Nov. 26, 2014

(86) PCT No.: PCT/US2014/067788
§ 371 (c)(1),
(2) Date: May 25, 2016

(87) PCT Pub. No.: WO2015/081310
PCT Pub. Date: Jun. 4, 2015

(65) Prior Publication Data
US 2016/0331875 A1    Nov. 17, 2016

Related U.S. Application Data

(60) Provisional application No. 61/909,798, filed on Nov. 27, 2013.

(51) Int. Cl.
| | | |
|---|---|---|
| *A61K 9/26* | (2006.01) | |
| *A61L 31/14* | (2006.01) | |
| *A61L 27/34* | (2006.01) | |
| *A61L 27/50* | (2006.01) | |
| *A61L 27/54* | (2006.01) | |
| *A61L 29/08* | (2006.01) | |
| *A61L 29/14* | (2006.01) | |
| *A61L 29/16* | (2006.01) | |
| *A61L 31/10* | (2006.01) | |
| *A61L 31/16* | (2006.01) | |
| *A61K 9/51* | (2006.01) | |
| *A61K 9/50* | (2006.01) | |

(52) U.S. Cl.
CPC ............ *A61L 31/14* (2013.01); *A61K 9/5031* (2013.01); *A61K 9/5146* (2013.01); *A61L 27/34* (2013.01); *A61L 27/50* (2013.01); *A61L 27/54* (2013.01); *A61L 29/085* (2013.01); *A61L 29/14* (2013.01); *A61L 29/16* (2013.01); *A61L 31/10* (2013.01); *A61L 31/16* (2013.01); *A61L 2400/00* (2013.01)

(58) Field of Classification Search
CPC .......... A61L 31/14; A61L 27/34; A61L 27/50; A61L 27/54; A61L 29/085; A61L 29/14; A61L 29/16; A61L 31/10; A61L 31/16; A61L 2400/00; A61K 9/5146; A61K 9/5031
See application file for complete search history.

(56) References Cited

U.S. PATENT DOCUMENTS

| 3,710,795 A | 1/1973 | Higuchi et al. | |
|---|---|---|---|
| 2010/0015239 A1* | 1/2010 | Ahmed ............... | A61K 9/5026 424/497 |
| 2012/0156135 A1 | 6/2012 | Farokhzad et al. | |

FOREIGN PATENT DOCUMENTS

| CN | 102068332 A | 5/2011 |
|---|---|---|
| WO | 2013/013038 A2 | 1/2013 |

OTHER PUBLICATIONS

Wu, C. et al., "The effect of mesoporous bioactive glass on the physiochemical, biological and drug-release properties of poly(DL-lactide-co-glycolide) films," Biomaterials 30 (2009), pp. 2199-2208.*
Z. Piao et al., "Comparison of Release-Controlling Efficiency of Polymeric Coating Materials Using Matrix-type Cased Films and Diffusion-Controlled Coated Tablet," AAPS PharmSciTech, vol. 11, No. 2, Jun. 2010, pp. 630-636.*
Y. Xia et al., "Selective laser sintering fabrication of nano-hydroyapatite/poly-ε-caprolactone scaffolds for bone tissue engineering applications," International Journal of Nanomedicine 2013:8, pp. 4197-4213.*
Dyakonov et al., "Design and Characterization of a Silk-Fibroin-Based Drug Delivery Platform Using Naproxen as a Model Drug", J Drug Deliv., 2012(490514):1-10 (2012).
Fang et al., "Poly (ε-caprolactone) coating delays vancomycin delivery from porous chitosan/β-tricalcium phosphate composites", J Biomed Mater Res B Appl Biomater., 100(7):1803-11 (2012).
Kumar et al., "An Overview of Stimuli-Induced Pulsatile Drug Delivery Systems", Int. J. of Pharm Tech Research, 2 (4):2364-78 (2010).
Lalwani et al., "Pulsatile Drug Delivery Systems", Indian J Pharm Sci., 69(4);489-497 (2007).
Moghadam et al., "Controlled release from a mechanically-stimulated thermosensitive self-heating composite hydrogel", Biomaterials, 35(1):450-5 (2014).
Rosenberg et al., "Release of Highly Hydrophilic Drugs from Poly(ε-caprolactone) Matrices", Journal of Applied Polymer Science, 107(5):3149-3156 (2008).

(Continued)

*Primary Examiner* — Brian Gulledge
(74) *Attorney, Agent, or Firm* — Nixon Peabody LLP; Ravinderjit Braich; Jeanne Jodoin

(57) ABSTRACT

The disclosure provides a drug delivery device that can release a drug or other molecule of interest in response to application of a mechanical force, such as tension, and methods of use thereof. The present disclosure provides a tension-responsive drug delivery device by exploiting a difference in mechanical properties between a drug-loaded core material and a supertiydrophobic barrier coating consisting of interconnected micro- and nano-sized particles formulated via the electrospraying of a mixture of biocompatible polymers.

16 Claims, 32 Drawing Sheets

(56) References Cited

OTHER PUBLICATIONS

Sershen et al., "Implantable, polymeric systems for modulated drug delivery", Adv Drug Deliv Rev., 54(9):1225-35 (2002).
Surnar et al., "Stimuli-Responsive Poly(caprolactone) Vesicles for Dual Drug Delivery under the Gastrointestinal Tract", Biomacromolecules, 14(12);4377-4387 (2013).
Weixin et al., "Biological Applications of Biomimetic Superhydrophobic Surfaces" Acta. Chim. Simica, 70:2393-2403, (2012).
Yohe et al., "Triggered Drug Release from Superhydrophobic Meshes using High-Intensity Focused Ultrasound", Adv Healthc Mater., 2(9):1204-8 (2013).
Zhou et al., "A novel pulsed drug-delivery system: polyelectrolyte layer-by-layer coating of chitosan-alginate microgels", Int. J. Nanomedicine 8:877-87 (2013).
Lima et al., "Synthesis of Temperature-Responsive Dextran-MA/PNIPAAm Particles for Controlled Drug Delivery Using Superhydrophobic Surfaces", Pharm Res. 28:1294-1305 (2011).
Song et al., "Bioinspired methodology to fabricate hydrogel spheres for multi-applications using superhydrophobic substrates", Soft Matter 6:5868-5871 (2010).
Yohe et al., "3D Superhydrophobic Electrospun Meshes as Reinforcement Materials for Sustained Local Drug Delivery Against Colorectal Cancer Cells", J Control Release 162(1): 92-101 (2012).
Yohe et al., "Superhydrophobic Materials for Tunable Drug Release: Using Displacement of Air to Control Delivery Rates", J Am Chem Soc. 134(4):2016-2019 (2012).

\* cited by examiner

STRETCH RELEASE DRUG DELIVERY MATERIALS

CROSS REFERENCE TO RELATED APPLICATIONS

This application is a 371 National Phase Entry of International Patent Application No. PCT/US2014/067788 filed on Nov. 26, 2014 which claims benefit under 35 U.S.C. § 119(e) of the U.S. Provisional Application No. 61/909,798, filed Nov. 27, 2013, the contents of which are incorporated herein by reference in their entirety.

GOVERNMENT SUPPORT

This invention was made with Government Support under Contract No. EB006359 awarded by the National Institutes of Health, and Contract No. DGE-1247312 awarded by the National Science Foundation. The Government has certain rights in the invention.

TECHNICAL FIELD

The present invention relates to the delivery of chemical, biological, and/or pharmaceutical agents for the treatment of medical conditions. More specifically, the present invention describes a method of delivery that exploits a difference in mechanical properties between the individual layers of multilayered polymer matrices containing entrapped, adsorbed, or otherwise incorporated agents for biomedical use, and said agents become released upon mechanical stimulation. Applications of such a method and material include, but are not limited to, their use in transarterial or intrathoracic drug administration. The device is comprised of two or more layers of polymer matrix, wherein at least two different layers exhibit a discrepancy in mechanical properties such that upon mechanical stimulation, such as tension, shear force, compression, and/or ultrasound, the weaker layer fractures to either direct diffusion of contained agents, cause an infiltration of water and subsequent drug diffusion, or a combination thereof. The form of such a device can be cylindrical (i.e., tube or rod), circular or spherical, rectangular, or any combination thereof. Further control over the release of the agent can be achieved by modulating the interactions between the agent and the core and/or the coating layer via chemical conjugation, electrostatic interactions, Van der Waals interactions and the like.

BACKGROUND

Materials responsive to stimuli, such as temperature, pH, applied magnetic field, and mechanical stress are important in biomedicine because they allow spatiotemporal control over drug release. However, there remains a need in the art for materials responsive to mechanical forces for drug delivery and methods using application of mechanical forces for timed delivery, such as drug delivery.

SUMMARY OF THE INVENTION

The present disclosure provides a tension-responsive drug delivery device by exploiting a difference in mechanical properties between a drug-loaded core material and a superhydrophobic barrier coating consisting of interconnected micro- and nano-sized particles formulated via the electrospraying of a mixture of biocompatible polymers: poly(ε-caprolactone) [PCL] and poly(glycerol stearate-co-ε-caprolactone). The textured superhydrophobic (contact angle >167°) surface employs microscopic structural topographical features commonly observed in nature to increase surface roughness and prohibit water infiltration. In the absence of tension, this superhydrophobic coating maintains a stable air layer that protects against wetting into the underlying cisplatin-loaded core. However, upon the application of force, this protective barrier breaks down through crack propagation to afford rapid water infiltration and subsequent release of cisplatin from the core. The amount of drug released is dependent on the tensile strain applied to break the superhydrophobic coating, and in vitro cell assays on cancer cell lines demonstrated release of a therapeutic cisplatin dose. Further control over the release of the agent can be achieved by modulating the interactions between the agent and the core and/or the coating layer via chemical conjugation, electrostatic interactions, Van der Waals interactions and the like.

In one aspect, the disclosure provides a drug-delivery device comprising a core and a superhydrophobic coating layer on at least one surface of the core, wherein the core comprises an agent distributed in a matrix material, and wherein the core and the coating layer have at least one mechanical property that is different.

Generally, the coating surface has a high contact angel and/or high surface roughness. Coating thickness can range from nanometer scale to millimeter scale. Further, the coating can be single layer or a multi-layered. When the coating is multilayered, each layer can be the same, each different or a combination of same and different.

Any desired material can be used for the coating. Exemplary materials for the coating include, but are not limited to, polyesters, polycarbonates, polyamides, polyethers, polyanhydrides, polyacrylates, and copolymers and mixtures thereof. In one embodiment, the coating comprises poly (caprolactone) and poly(glycerol monostearate-co-caprolatone).

Without limitation, the agent in the core can be any desired compound, molecule or composition for delivery. For example, the agent can be selected from drugs or biologically active compounds, molecules or compositions; nutrients; flavors or fragrances; fluids/liquids, oils; diagnostic agents; vaccines; and the like. In other words, any material that one needs to time deliver can be included in the core. Further, the agent can be selected from the group consisting of small organic or inorganic molecules, peptides, peptide analogs and derivatives, peptidomimetics, proteins, antibodies, antigen or epitope binding fragments of antibodies, nucleic acids, nucleic acid analogs and derivatives, an extract made from biological materials, and any combinations thereof.

The core can be of any shape or form. For example, the core can be in the form of a film, a particle, a mesh, a fiber, a gel, a hydrogel, a foam, a mesh, a mat, a non-woven mat, or any combinations thereof. Further, the core can be single layered or multilayered. In some embodiments, the core is porous or comprised of an absorbent material.

Like the coating, any desired material can be used for the core. Exemplary materials for the core include, but are not limited to, polyesters, polycarbonates, polyamides, polyethers, polyanhydrides, polyacrylates, polyurethanes, and mixture or copolymers thereof. Further, the core can be made from a hydrophilic or hydrophobic material.

In another aspect, the disclosure provides a method of controlling the release of an agent. Generally, the method comprises providing a drug-delivery device described herein and applying a mechanical force on the drug delivery device.

Without wishing to be bound by a theory, the mechanical force induces cracks or crack propagation in the coating layer thereby allowing the agent to diffuse from the core.

Exemplary mechanical forces include, but are not limited to tension, shear force, compression, ultrasound, and any combinations thereof. The mechanical force can be applied by an external source or the device can be incorporated into expandable or extendable medical devices. In another non-limiting example, the mechanical force can be from chewing on the drug-delivery device.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 1 is a photographs showing electrosprayed hydrophobic coating on cellulose/polyester mesh.

FIG. 2 is a photograph showing image of an electrosprayed hydrophobic surface coating of poly(caprolactone) with a water droplet. The apparent contact angle is 122°.

FIG. 3 is a photograph of an electrosprayed coating on an otherwise water absorbent core material.

FIG. 4 is an image of an electrosprayed superhydrophobic surface of poly(glycerol monostearate-co-ε-caprolactone) and poly(caprolactone) with a water droplet. The apparent contact angle is 170°.

FIG. 5 is a scanning electron micrograph of the surface of the superhydrophobic poly(glycerol monostearate-co-ε-caprolactone) and poly(caprolactone) electrosprayed surface from a 20% (w/v) solution. Scale bar=10 urn.

FIG. 6 shows apparent contact angles on the electrosprayed surface increase as the doping concentration of PGC-C18 is increased relative to PCL.

FIG. 7 shows advancing contact angle measurements with water droplet on electrosprayed surface. (a) A 70/30 mixture of PCL/PGC-C18, showing an apparent water contact angle of 146.6°, characteristic of a hydrophobic surface. (b) A 50/50 mixture of PGC-C18 and PCL, showing an apparent water contact angle of 160°, characteristic of a superhydrophobic surface.

FIG. 8 shows apparent contact angle dependence on electrosprayed particle size.

FIG. 9 is a scanning electron microscope (SEM) image of polymer particles on surface. (a) Average diameter size=6000 nm, (b) Average diameter size=4300 nm.

FIG. 10 shows decreasing polymer concentration yields less connected particles. Scale bar=10 μm.

FIG. 11 shows contact angle measurements with water droplet on various surfaces. (a) Water soaks into a cellulose/polyester blend (CA=0°), (b) water droplet on hydrophobic surface (CA=122°), (c) water droplet on superhydrophobic surface (CA=170°).

FIG. 12 is a low-magnification scanning electron micrograph of superhydrophobic surface (100×).

FIG. 13 is a higher magnification scanning electron micrograph of superhydrophobic surface (500×).

FIG. 14 is a scanning electron micrograph of cross-section of electropray-coated superhydrophobic surface at 100× magnification. Note presence of fibers at cellulose/polyester core.

FIG. 15 shows (from left to right) hydroentangled cellulose/polyester mesh, an uncoated mesh loaded with hydrophilic green dye, and a mesh loaded with green dye and surface-treated with an electrosprayed coating of PGC-C18 and PCL.

FIG. 16 is a UV-vis trace of a hydrophilic green dye. The local maximum absorbance at 630 nm was used for quantification of dye concentration in aliquots sampled at varying time points.

FIG. 17 shows constructed standard curve for a hydrophilic green dye as using UV-Visible spectrophotometry. The absorbance wavelength used for detection was 630 nm.

FIG. 18 shows (from top to bottom) unloaded hydroentangled cellulose and polyester mesh; a mesh loaded with FITC-BSA and subsequently surface-treated with an electrosprayed coating of PGC-C18 and PCL; and a mesh loaded with FITC-BSA prior to surface treatment.

FIG. 19 shows constructed standard curve for FITC-BSA as measured with fluorimeter. The excitation wavelength is 495 nm and the emission wavelength is 520 nm.

FIG. 20 is a fluorescence emission scan of FITC-BSA at excitation of 495 nm, showing maximum emission at 520 nm.

FIG. 21 is a fluorescence excitation scan of FITC-BSA at emission wavelength of 520 nm, showing an excitation maximum at 495 nm.

FIG. 22 shows a cisplatin-loaded core nanofiber mesh for use as a mechanoresponsive drug delivery device.

FIG. 23 shows tension-triggered release of a hydrophilic dye from a mechanoresponsive drug delivery material. The blue curve shows rapid release after the application of 100% strain (t=0), whereas the control (no applied tension) shows minimal release.

FIG. 24. shows tension-triggered release of the protein FITC-BSA from a mechanoresponsive drug delivery material. The blue curve shows rapid release after the application of 100% strain (t=0), whereas the control (no applied tension) shows minimal release.

FIG. 25 shows tension-triggered release of cisplatin from a mechanoresponsive drug delivery material. The blue curve shows rapid release after the application of 100% strain (t=30 min), whereas the control (no applied tension) shows minimal release.

FIG. 26 shows tension-triggered release of a hydrophilic dye from a mechanoresponsive drug delivery material in the presence of 10% serum. The blue curve shows rapid release after the application of 100% strain (t=0), whereas the control (no applied tension) shows minimal release.

FIG. 27 shows strain-modulated release of a hydrophilic dye from a mechanoresponsive drug delivery material in the presence of PBS or PBS supplemented with 10% serum. The blue curve shows rapid release after the application of 100% strain (t=0), the red curve shows a more modest release profile generated under 30% strain, and the black curve shows the control (no applied tension) exhibiting minimal release. Error bars represent +/−SD.

FIG. 28 is a cross-section scanning electron microscopy of dye-loaded drug delivery system electrosprayed at a tip-to-collector distance of 10 cm, with inserts of magnified coating (upper left) and crack pattern (right). The morphology of the coating is described as wet due to melded particles. Scale bar=100 μm, scale bar of insert=10 μm.

FIG. 29 is a cross-section scanning electron microscopy of dye-loaded drug delivery system electrosprayed at a tip-to-collector distance of 15 cm, with inserts of magnified coating (upper left) and crack pattern (right). The morphology of the coating is described as dry due to decreased particle connectivity. Scale bar=100 μm, scale bar of insert=10 μm.

FIG. 30 shows strain-modulated release of a hydrophilic dye from a mechanoresponsive drug delivery material in the presence of PBS supplemented with 10% serum. The dark green curve shows rapid release after the application of 100% strain (t=0), the light green curve shows a modest release profile generated under 50% strain, the green curve shows a more modest release profile generated under 30% strain, and the black curve shows the control (no applied tension) exhibiting minimal release. Error bar represents+1 SD.

FIG. 31 shows tension-triggered release of the protein FITC-BSA from a mechanoresponsive drug delivery material. The brown curve shows rapid release after the application of 100% strain (t=0), the orange curve shows a modest release profile generated under 50% strain, and the black curve shows the control (no applied tension) exhibiting minimal release. Error bar represents+/−1 SD.

Figure 39:
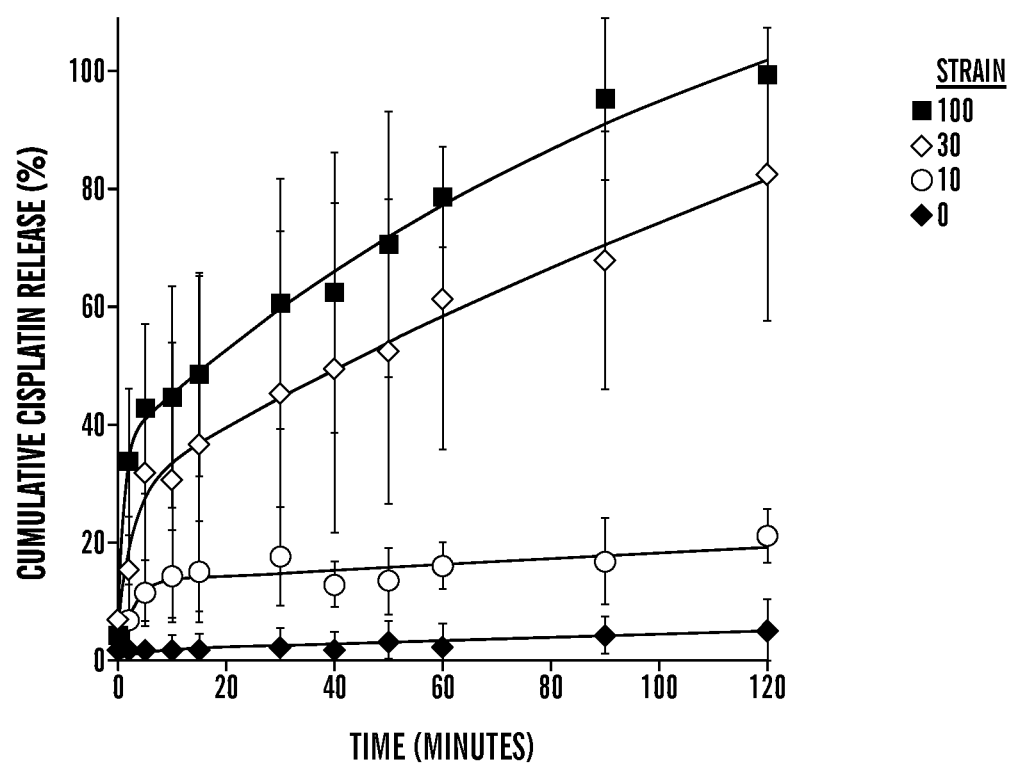

FIG. 39 shows tension-dependent release of cisplatin. After application of strain, cisplatin was released into cell media solution (RPMI) with fetal bovine serum (10% v/v). The amount of cisplatin was determined by atomic absorption spectroscopy (Example 16).

Figure 40:
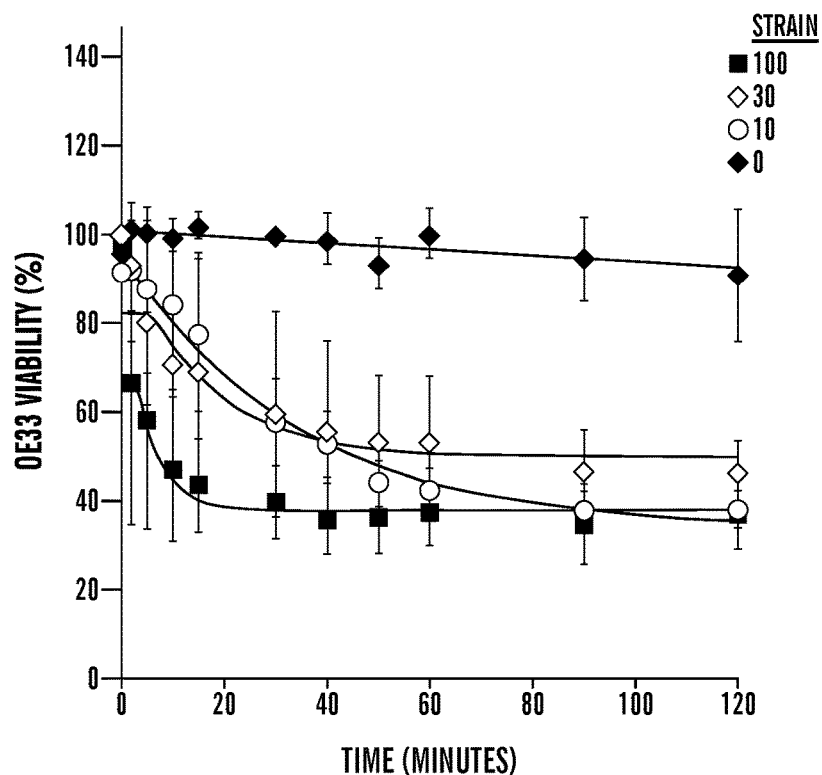
Figure 40:
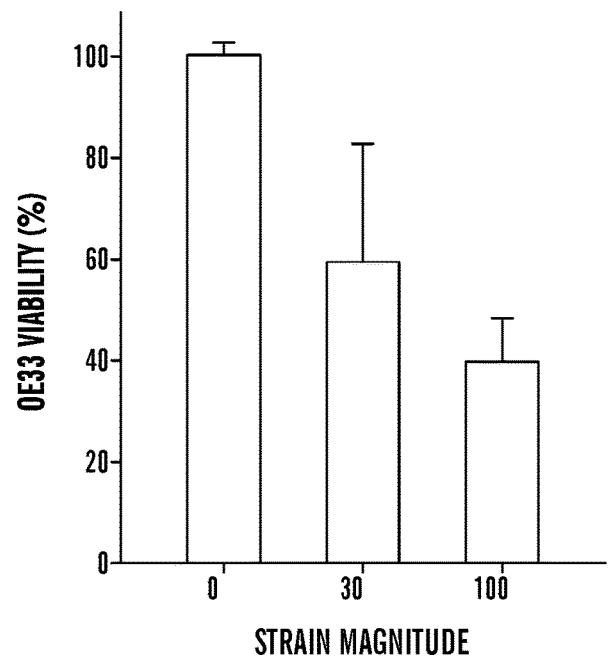

FIG. 40 shows cell viability depends on the strain input and corresponding drug release. Aliquots from release (FIG. 39) were incubated for 72 hours with OE33 cells, an oesophageal cell line. Cell viability from incubation of release aliquots over two hours were determined by MTS Assay, left. Cell viability at the 30-minute release at various strain magnitude are shown, right ($p<0.05$ for 30%, 100% when compared to 0%).

Figure 41:
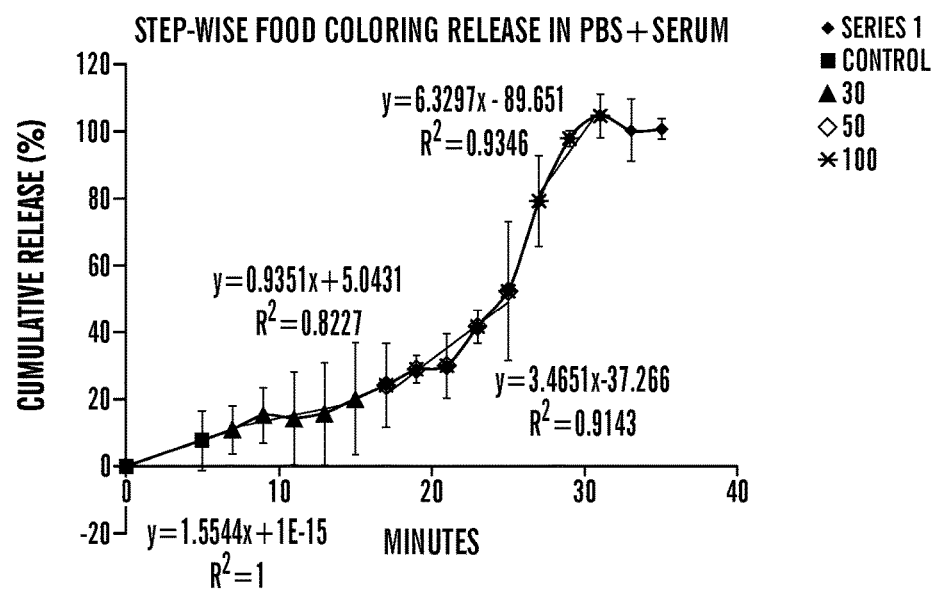
Figure 41:
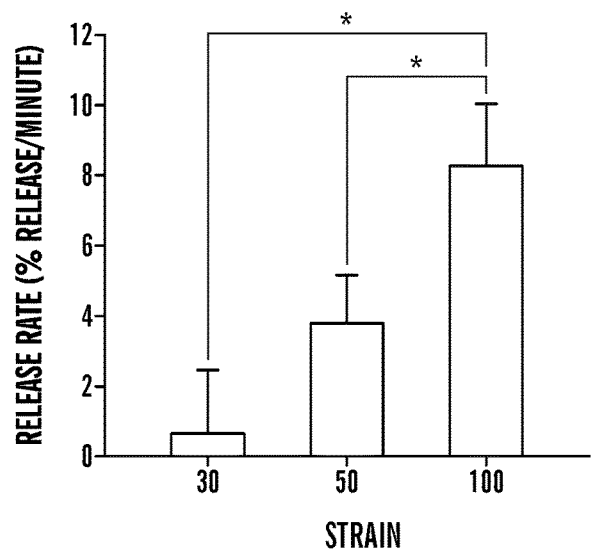

FIG. 41 Step-wise release of loaded dye. The dye release rate increases with increasing applied strain, as quantified through cumulative release and rate of release.

Figure 42:
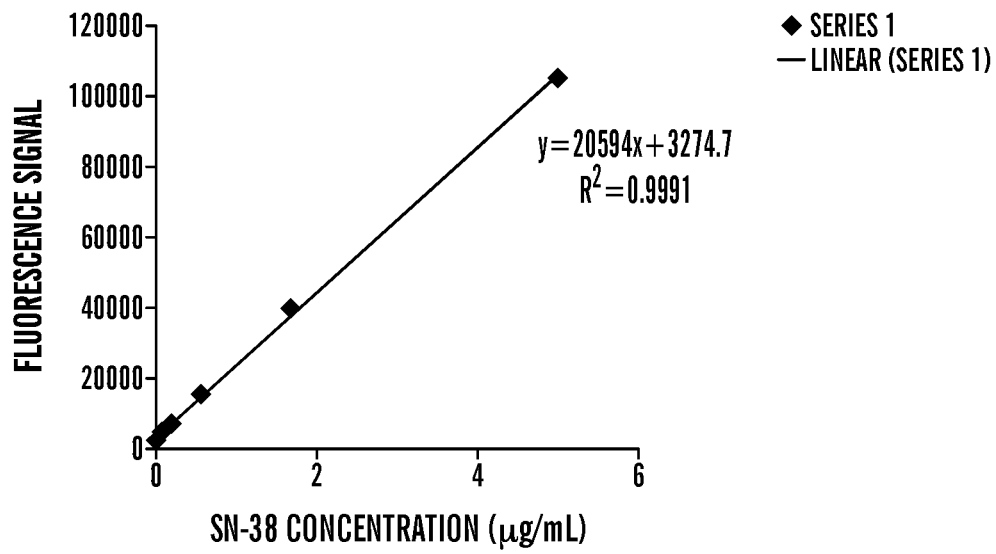

FIG. 42 Standard curve for detection of SN-38 in borate buffer by fluorimetry.

Figure 43:
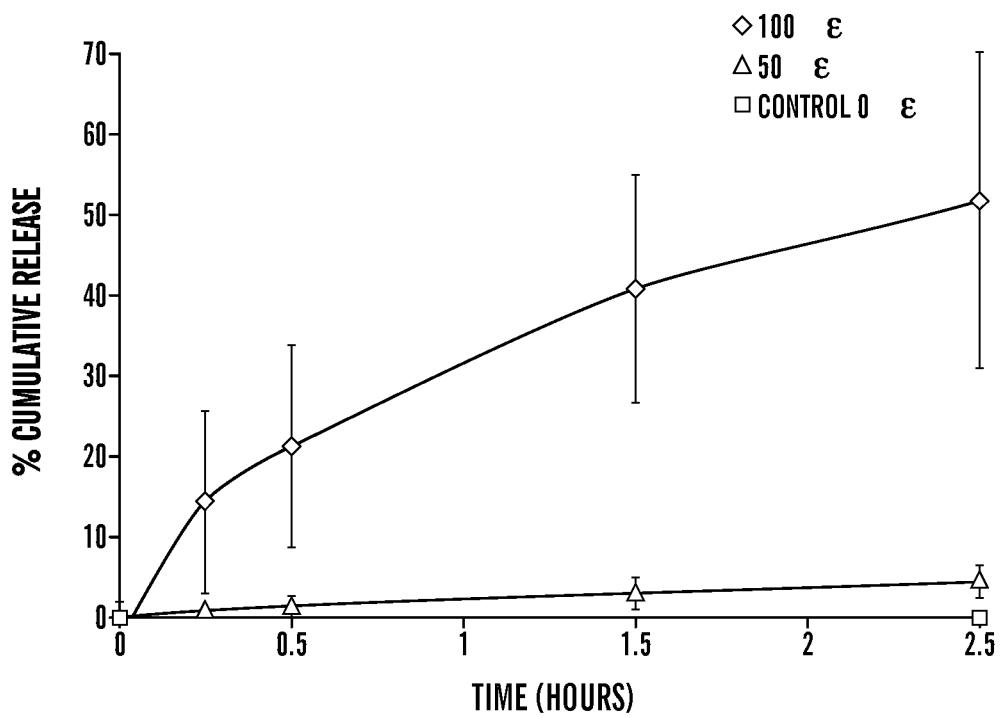

FIG. 43 Cumulative release of SN-38 by applying strain on mechanoresponsive drug delivery device.

Figure 44:
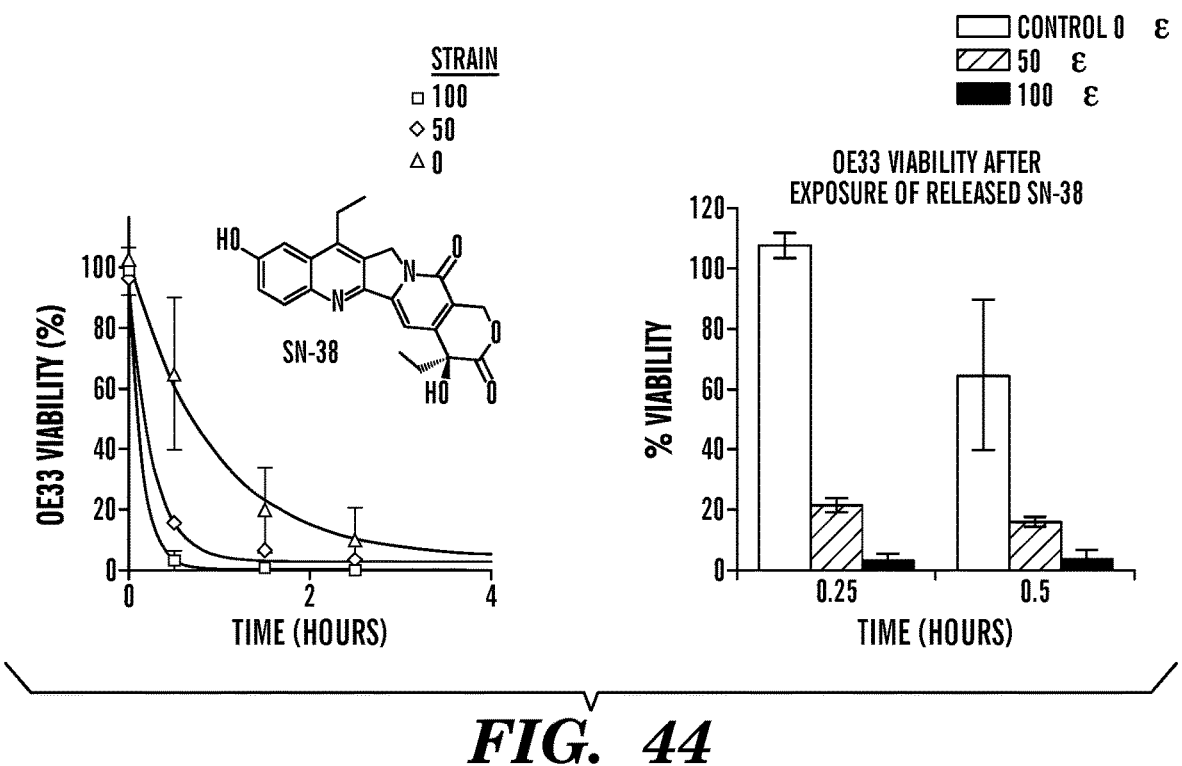

FIG. 44 Aliquots of SN-38 release in media (RPMI) with 10% fetal bovine serum were incubated for 96 hours with significant decreases in viability with increasing strain.

Figure 45:
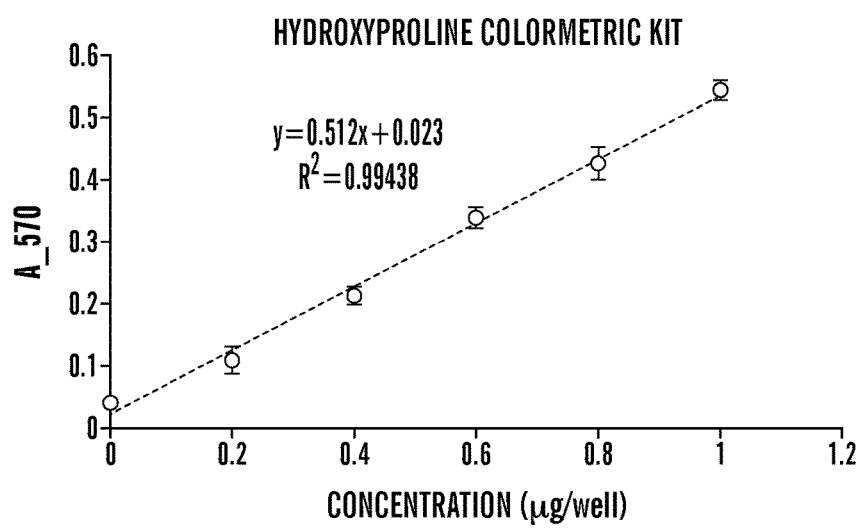

FIG. 45 Standard curve with spiked hydroxyproline samples analyzed by hydroxyproline assay kit.

Figure 46:
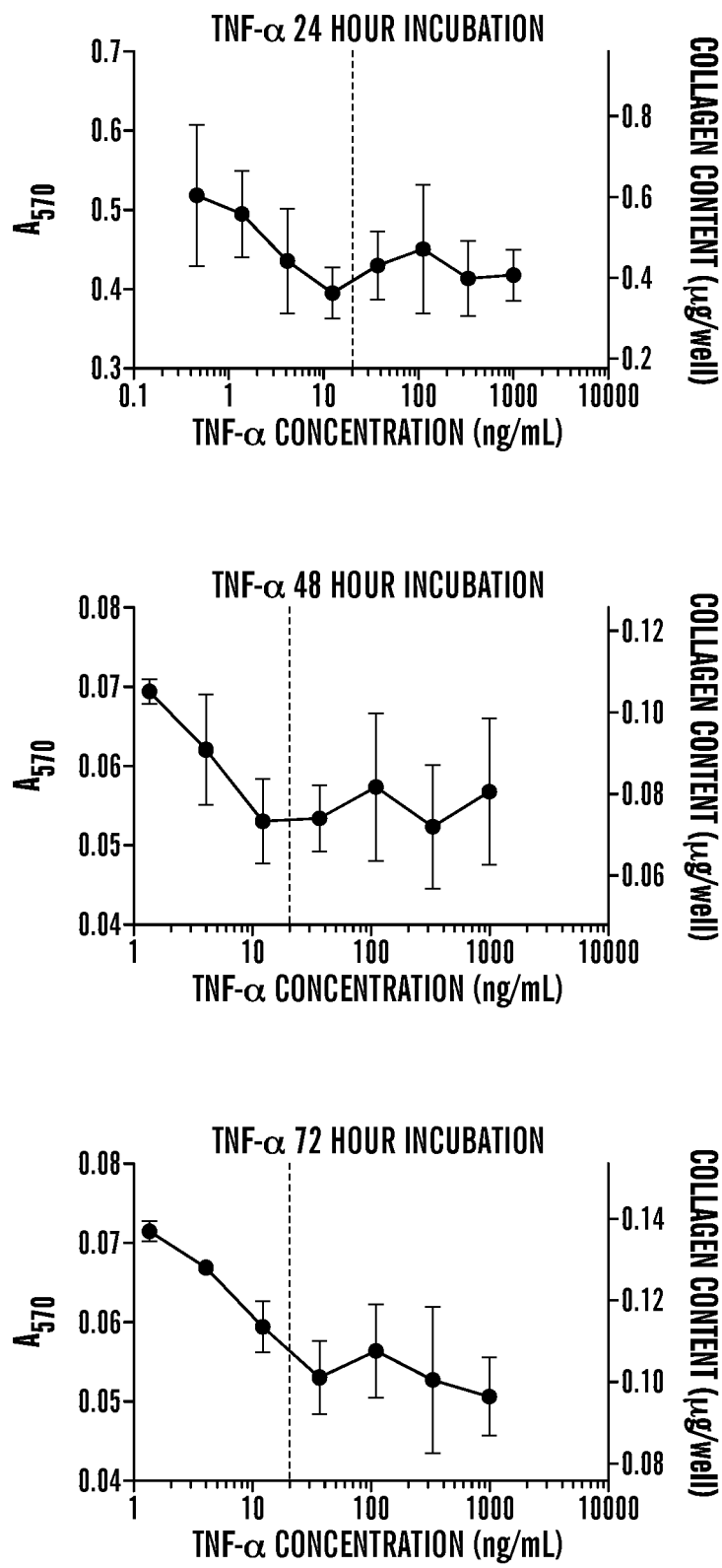

FIG. 46 Examples of expected cellular collagen response to TNF-α delivery. In these cases the 3T3 fibroblasts were incubated with a known concentration of TNF-α.

Figure 47:
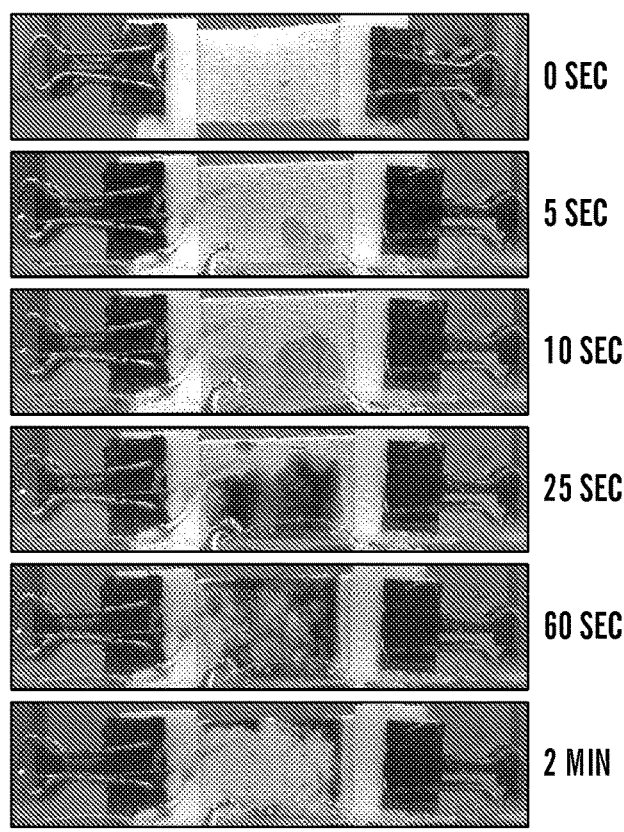
Figure 47:
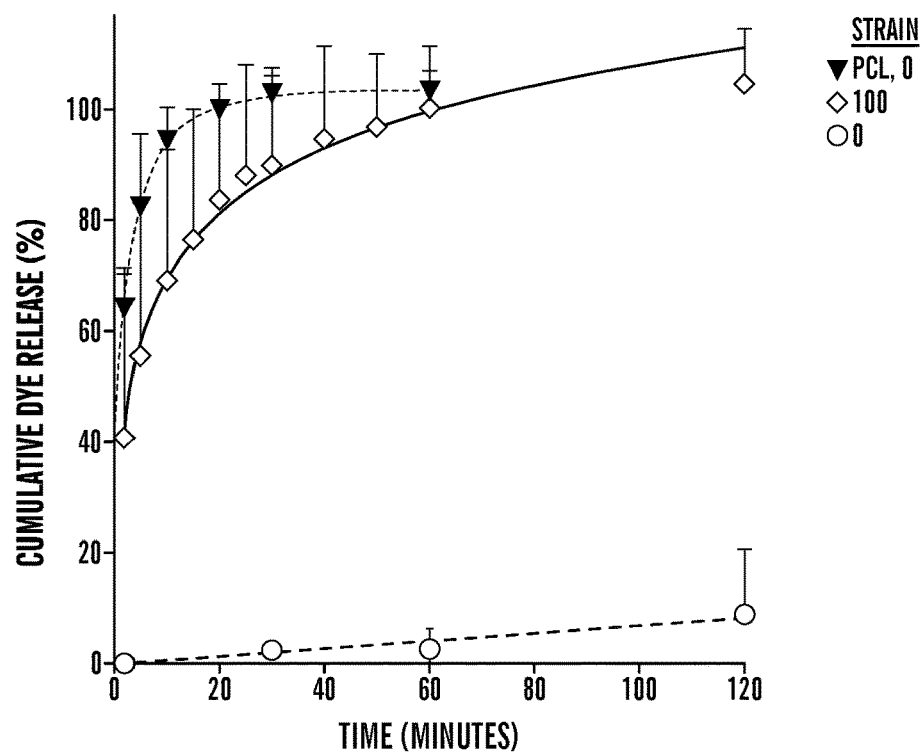

FIG. 47 Dye release from hydrophobic coating with no applied tension or strain with corresponding times (right). Quantified dye release from hydrophobic coating (PCL, 0%; blue) compared to dye release from superhydrophobic coating under the absence of tension (0%; black) and in the presence of 100% strain (100%; green).

Figure 48:
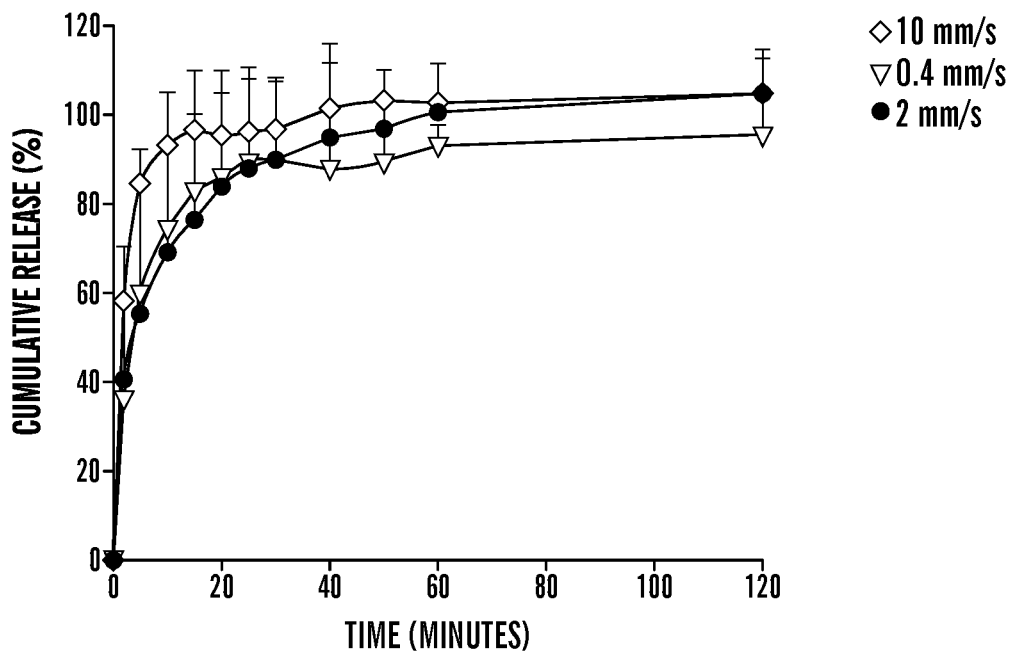

FIG. 48 Release of dye-loaded mechanoresponsive drug delivery device at various loading rates (10 mm/s, 0.4 mm/s, 2 mm/s) at 100% strain.

Figure 49:
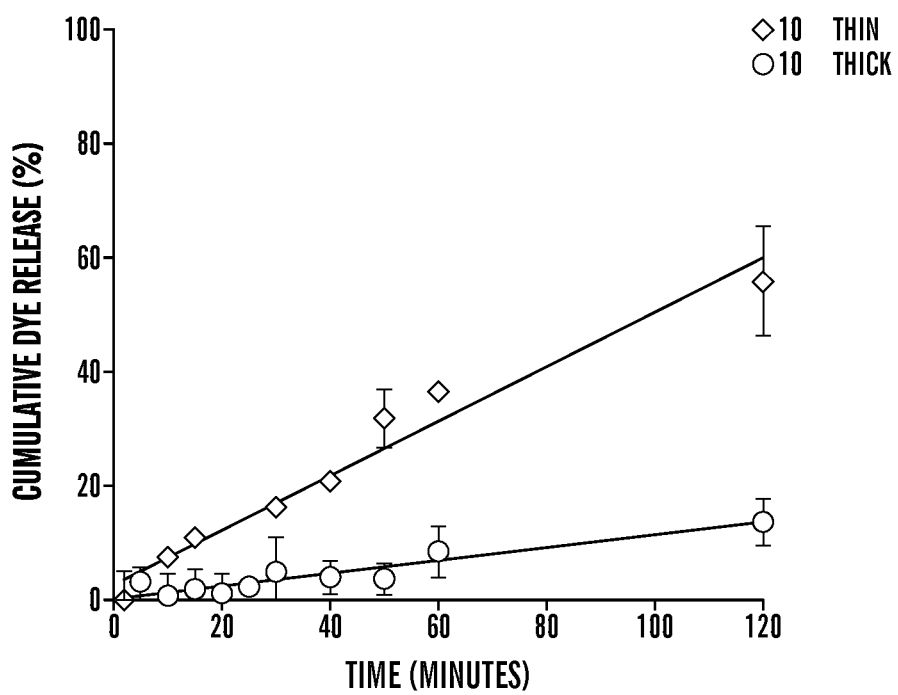

FIG. 49 Significant decreases in dye release rate with thicker superhydrophobic coating.

Figure 50:
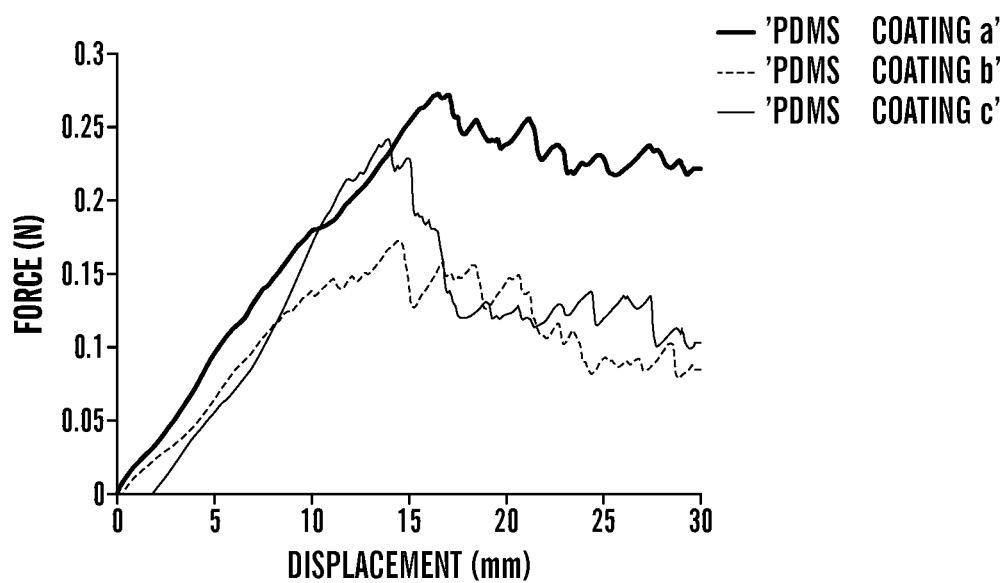

FIG. 50 Force vs displacement traces with compact-tension specimens used to determine $G_{Ic}$, $K_{Ic}$, and E.

Figure 51:
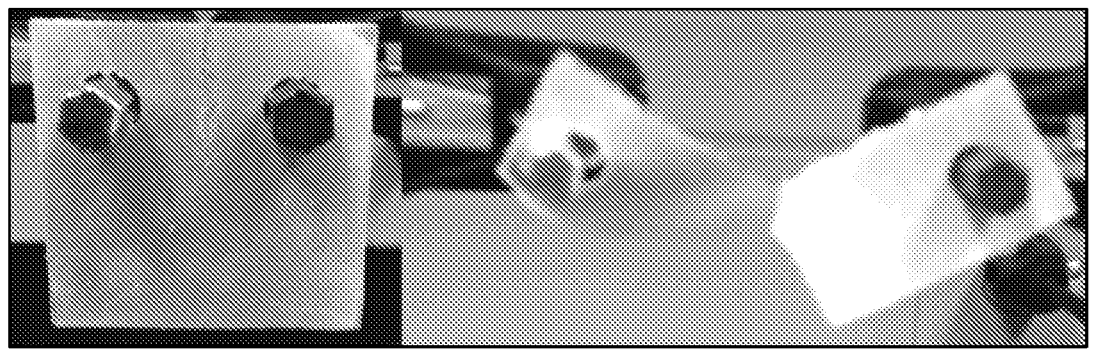

FIG. 51 Compact-tension specimens before (left) and during (right) tensile testing. Specimens were composed of PDMS, sputtercoated with gold, and electrosprayed with the superhydrophobic coating.

Figure 52:
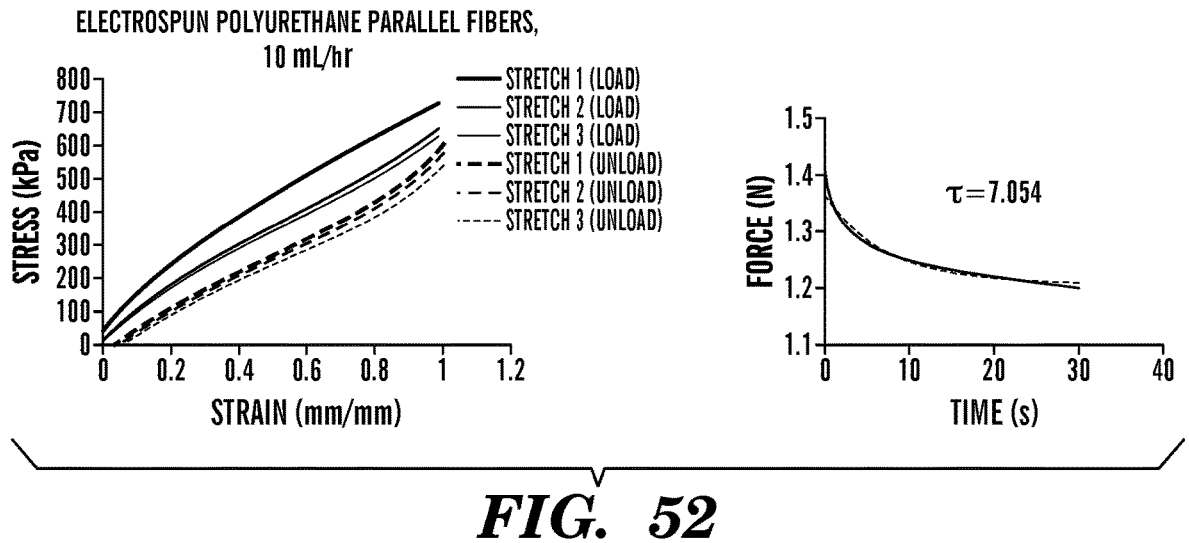

FIG. 52 Polyurethane meshes undergoing cyclic tension to determine modulus (left) and stress relaxation (right).

Figure 53:
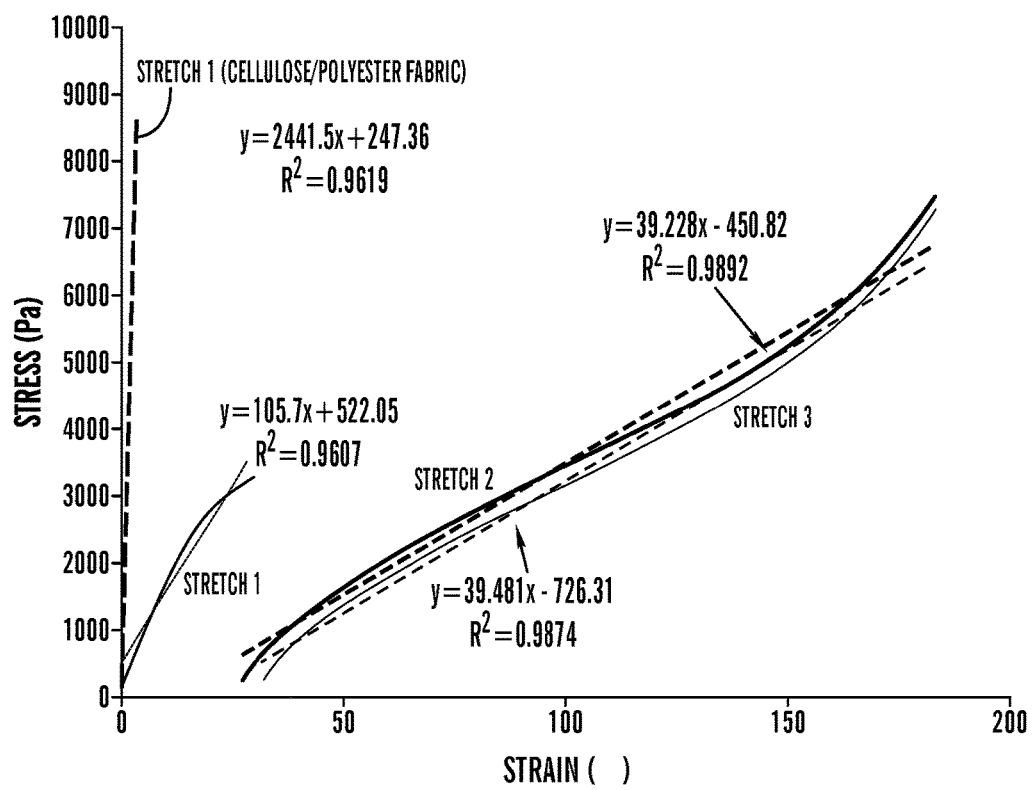

FIG. 53 Cyclic mechanical testing on a polyurethane substrate with low hysteresis between cycles.

Figure 54:
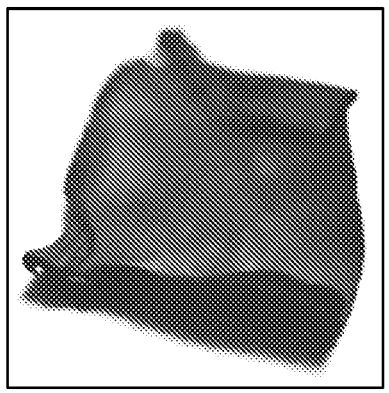

FIG. 54 Photograph of dye loaded polyurethane mesh.

Figure 55:
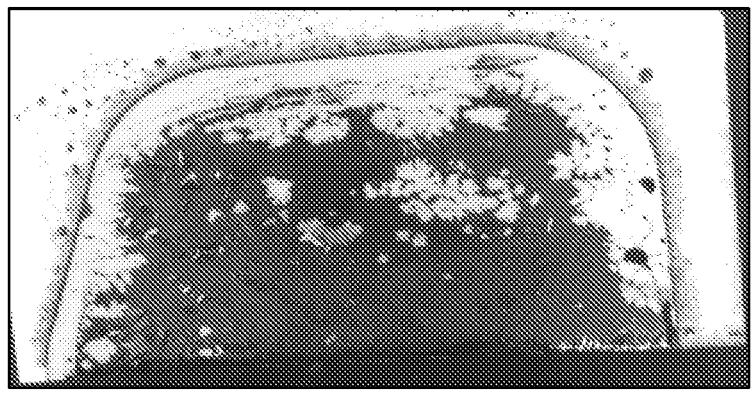

FIG. 55 Photograph of polyurethane substrate with rhodamine incorporation (dissolved in EtOH and MeOH).

Figure 56:
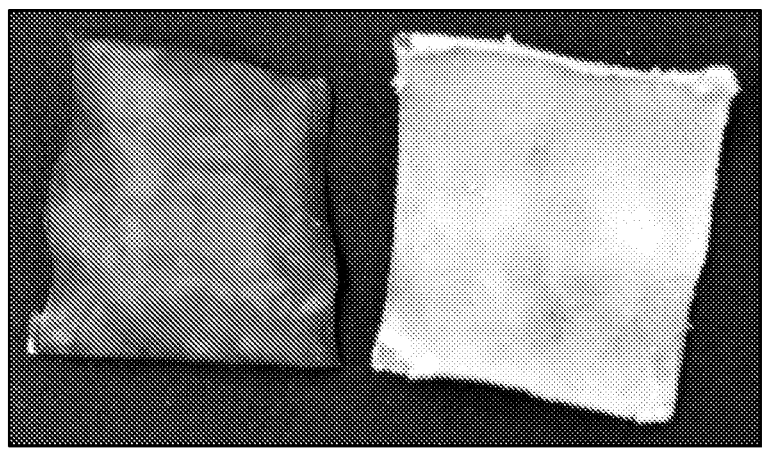

FIG. 56 Photograph of a dye-loaded electrospun polyurethane mesh (left) and an electrosprayed superhydrophobic system (right).

Figure 57:
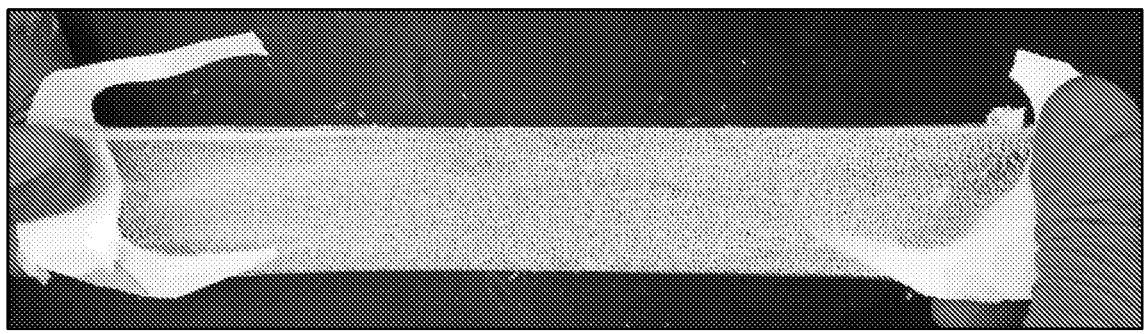

FIG. 57 Superhydrophobic coating electrosprayed on a polyurethane substrate under tension develops crack pattern to allow release.

Figure 58:
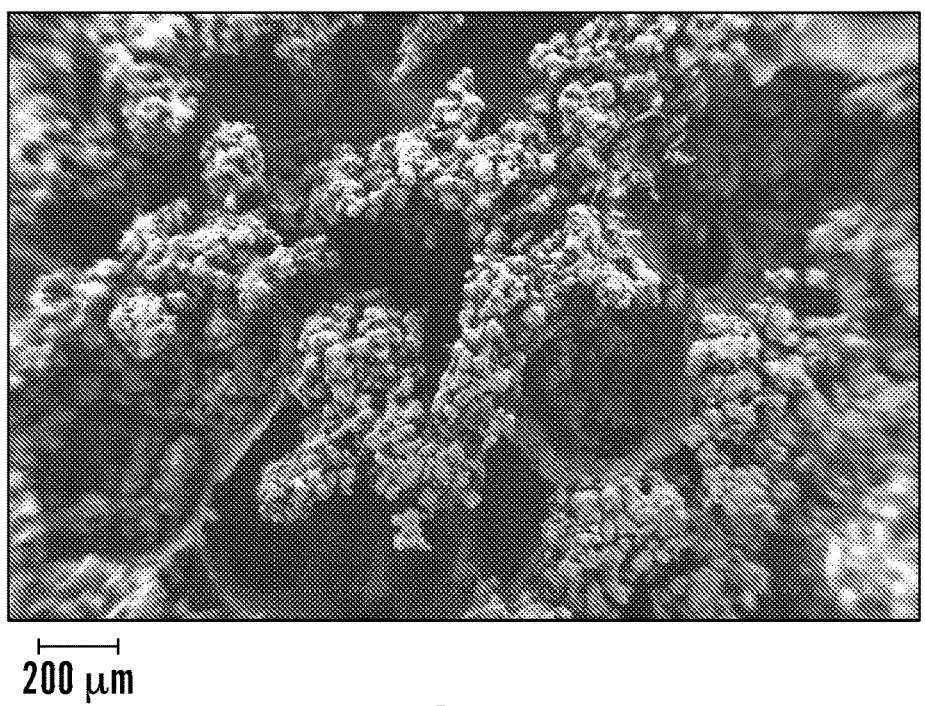

FIG. 58 Scanning electron micrograph of superhydrophobic surface electrosprayed on a porous material.

Figure 59:
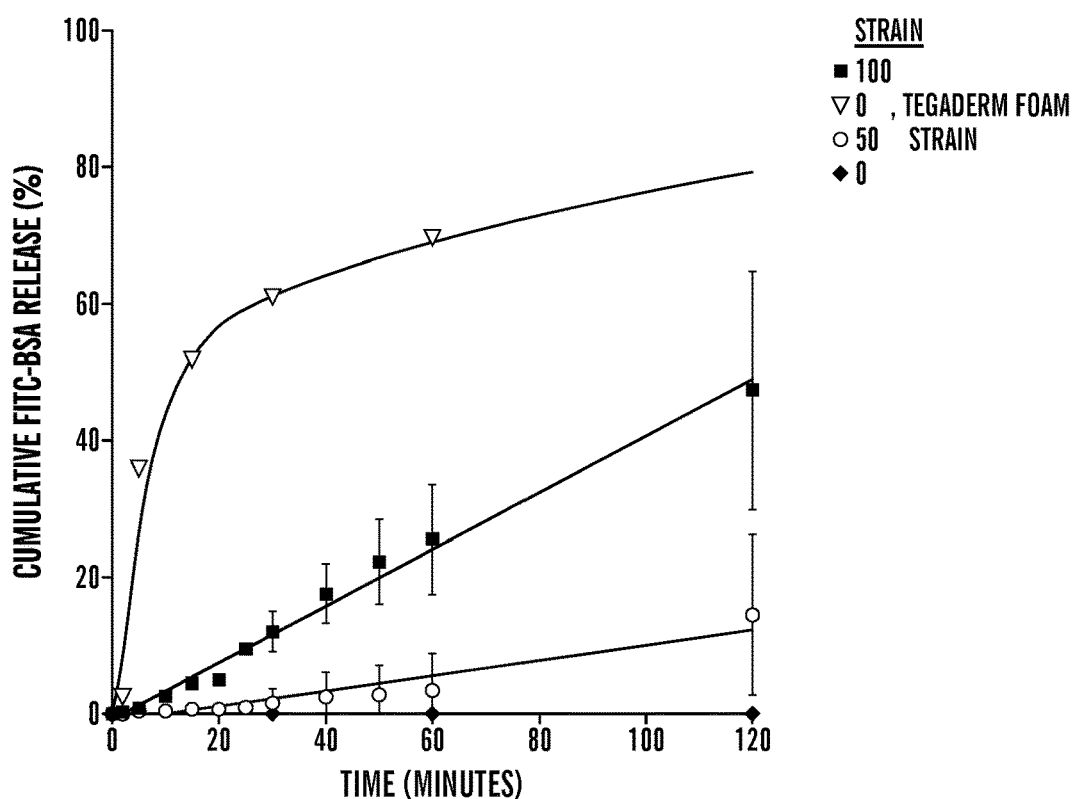

FIG. 59 Release of protein-loaded polyurethane foam as compared to superhydrophobic coated, protein-loaded mechanoresponsive drug delivery system.

DETAILED DESCRIPTION

Materials responsive to stimuli, such as temperature, pH, applied magnetic field, and mechanical stress are important in biomedicine because they allow spatiotemporal control over drug release. The focus of this study is the development of a tension-responsive drug delivery device, by exploiting a difference in mechanical properties between a agent-loaded core material and a superhydrophobic barrier coating. In the absence of tension, this superhydrophobic coating maintains a stable air layer that protects against wetting into the underlying drug-loaded core. However, upon the application of force, this protective barrier breaks down through crack propagation, causing water to rapidly infiltrate to release the agent from the core.

In one aspect, the disclosure provides a drug delivery device comprising an agent, (e.g., drug) loaded core material coated with a hydrophobic or superhydrophobic coating layer. It is noted that any reference to a drug loaded core herein is meant to include a core that comprises a molecule of interest (e.g., a drug). Thus, any reference to a drug is meant to include any molecule of interest that can be loaded into the core. Accordingly, the agent in the drug-loaded core can be selected the group consisting of small organic or inorganic molecules, peptides, peptide analogs and derivatives, peptidomimetics, proteins, antibodies, antigen or epitope binding fragments of antibodies, nucleic acids, nucleic acid analogs and derivatives, an extract made from biological materials, and any combinations thereof. Further, the agent in the drug-loaded core can be neutral or charged. Moreover, the agent in the drug-loaded core can be hydrophilic, or hydrophobic. While the disclosure describes drugs as the agent in the drug-loaded core, the agent can be any material that needs to be time delivered. For example, the agent can be selected from drugs, nutrients, flavors, oils, diagnostic agents, vaccines, materials that need stabilization and the like.

As used herein, the term "superhydrophobic" means and includes any surface with which a water droplet has a contact angle in air of at least 150°. The contact angle can be measured by a contact angle goniometer as described in ASTM Standard D7334-08. As used herein, the term "hydrophobic" refers to surfaces with a water contact angle from about 90° to about 120°. As used herein, the term "hydrophilic" refers to surfaces with water contact angles well below 90°.

In some embodiments, the superhydrophobic coating has a contact angle of from about 150° to about 175°. In some embodiments, the coating has a contact angle of at least 150°. In some embodiments, the coating has a contact angle of at least 155°, at least 160°, at least 165°, at least 170°, at least 175°, or higher.

The coating layer disclosed herein undergoes physical changes when a mechanical force is applied thereto. For example, the coating layer is responsive to mechanical forces. By "responsive to mechanical force" is meant that the coating layer undergoes permanent or non-permanent deformation when a mechanical force is applied to the drug delivery device. The coating layer is also referred to as a tension-responsive coating or layer herein.

Without wishing to be bound by a theory, the inventors have discovered that wettability of the surface depends on the thickness of the hydrophobic or superhydrophobic coating. The coating thickness can range from about a few nanometers to micrometers. For example, the coating thickness can range from about 10 nm to about 5000 µm. In some embodiments, the coating thickness can range from about 10 µm to about 1000 µm. In some embodiments, the coating thickness is 25 µm, 50 µm, 75 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm, 625 µm, 650 µm, 675 µm, 700 µm, 825 µm, 850 µm, 875 µm, 900 µm, 925 µm, 950 µm, 975 µm, 1000 µm or more. In some embodiments, the coating thickness is 25 µm, 50 µm, 75 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, 500 µm, 625 µm, 650 µm, 675 µm, 700 µm, 825 µm, 850 µm, 875 µm, 900 µm, 925 µm, 950 µm, 975 µm, 1000 µm or less. In some embodiments, the coating thickness is about 100 µm. In some other embodiments, the coating thickness is about 300 µm. In some embodiments, the coating thickness is about 50 µm to about 250 µm.

The coating layer surface can be smooth or rough. The term "surface roughness" means unevenness or ruggedness present of the surface of an object at narrow spacing. Surface roughness, often shortened to roughness, is a component of surface texture. It is quantified by the vertical deviations of a real surface from its ideal form. If these deviations are large, the surface is rough; if they are small, the surface is smooth. There are many different roughness parameters in use, but $R_a$ is by far the most common. Other common parameters include $R_z$, $R_q$ and $R_{sk}$. As used herein the term "smooth surface" is characterized by a surface roughness (Ra) less than or equal to 0.25 microns Increasing the roughness of a hydrophobic surface can increase its hydrophobicity. Accordingly, the coating layer generally has a high surface roughness. The coating layer can have an average surface roughness (Ra), as measured on a 5 µm×5 µm area, within a range having a lower limit and/or an upper limit. The range can include or exclude the lower limit and/or the upper limit. The lower limit and/or upper limit can be selected from 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, and 250 nm. For example, according to some embodiments, the coating layer can have an average surface roughness (Ra) of from 90 to 120 nm, or of about 104, nm, as measured on a 5 µm×5 µm area. In some embodiments, the coating layer can have an average surface roughness of from about 50 nm to about 100 nm, from about 105 nm to about 200 nm, or from about 200 nm to about 250 nm.

There are known generally two different types of methods for measuring surface roughness: a direct tracer method in which surface roughness of the object is measured directly with a tracer, and an optical method in which light rays are applied to the object surface and its roughness is measured optically by way of reflection or interference of the light rays applied.

One of skill in the art is well aware of the different methods that can be employed for forming a coating layer on a core. Exemplary methods include, but are not limited to, electrospraying, dip-coating, spray painting, and the like. In some embodiments, the coating can be formed by electrospraying.

In some embodiments, the coating layer comprises particles. As used herein, the term "particle" includes spheres; rods; shells; and prisms; and these particles can be part of a network or an aggregate. Without limitations, the particle can have any size from nm to millimeters. In some embodiments, the particle is a microparticle or a nanoparticle. As used herein, the term "microparticle" refers to a particle having a particle size of about 1 µm to about 1000 µm. As used herein, the term "nanoparticle" refers to particle having a particle size of about 1 nm to about 1000 nm.

The inventors have discovered that degree of hydrophobicity of the coating can be varied by changing the particle size comprised in the coating layer. Accordingly, the particle size can range from about 100 nm to about 25 µm. In some embodiments, the particle size can range from about 150 nm to about 10 µm. In some embodiments, the particle size is 500 nm, 1000 nm, 1250 nm, 1500 nm, 1750 nm, 2000 nm, 2250 nm, 2500 nm, 2750 nm, 3000 nm, 3250 nm, 3500 nm, 3750 nm, 4000 nm, 4250 nm, 4500 nm, 4750 nm, 5000 nm, 5250 nm, 5500 nm, 5750 nm, 6000 nm, 6250 nm, 6500 nm, 6750 nm, 7000 nm, 7250 nm, 7500 nm, 7750 nm, 8000 nm, 8250 nm, 8500 nm, 8750 nm, 8000 nm, 8250 nm, 8500 nm, 8750 nm, 9000 nm, 9250 nm, 9500 nm, 9750 nm or more. In some embodiments, the particle size is 100 µm, 75 µm, 50 µm, 25 µm, 15 µm, 10 µm or less. In some embodiments, the particle size is from about 3500 nm to about 6500 nm. In one embodiment, the particle size is from about 4000 nm to about 6000 nm.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photo-correlation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

Without limitations, the particles can be discrete particles or they can be interconnected. The degree of interconnection can be controlled by varying the concentration of the material used for forming the coating layer. For example, decreasing the concentration of the material used for forming the coating layer yields less connected particles.

In some embodiments, the coating layer is comprised of fibers, i.e., the material forming the coating layer is in the form of fibers.

In some embodiments, the material forming the coating layers is in the form of particles and fibers, i.e., part of the coating is comprised of fibers and part of the coating is comprised of particles. The fibers and particles can be present in discrete regions of the coating or mixed with each other.

In some embodiments, the coating layer is multilayer coating. For example, the coating layer can comprise two or more layers. Each layer in the multilayer structure can be the same or different. For example, the layers can be of the same thickness, each is of different thickness, or some are of same thickness and others are of different thickness. Further, each layer can be made from the same material, different materials or some from same materials and some from different materials.

The material for forming the coating layer can be any desired material that can form a hydrophobic or superhydrophobic layer. In some embodiments, the coating forming material is a polymeric material. For example, the coating material can be selected from polyesters, polycarbonates, polyamides, polyethers, polyanhydrides, polyacrylates and copolymers or mixtures thereof.

In some embodiments, the coating material comprises poly(caprolactone), poly(lactide-co-glycolide), poly(glycerol monostearate-co-caprolatone), or a mixture thereof.

In some embodiments, the coating layer comprises a mixture of two different materials, for example, two different polymeric materials. The ratio of the two different materials can be varied to optimize the properties of the coating layer. For example, the ratio can be varied to optimize one or more of the hydrophobicity, thickness, mechanical properties, particle size, and the like. Without limitation, ratio of first material to the second material can range from about 99:1 to about 1:99. In some embodiments, the ratio can be from about 50:1 to about 1:50. Preferably, the ratio is from about 10:1 to about 1:10. In some embodiments, the ratio is from about 7:3 to about 3:7. The ratio can be based on weight, mass, moles or volumes.

In one embodiment, the coating layer comprises a mixture of poly(caprolactone) (PCL) and poly(glycerol monostearate-co-caprolatone) (PGC-C18). In some embodiments, the ratio of PCL to PGC-C18 can range from about 10:1 to about 1:10. In some embodiments, the ratio is from about 7:3 to about 3:7. In one embodiment, the ratio is about 7:3.

In some embodiments, the coating layer also comprises a drug or agent. The drug incorporated into the coating layer can be the same as the one in the drug loaded core or a different drug.

The drug loaded core can comprise a matrix material and a drug or other molecule of interest dispersed or encapsulated in the matrix material. Without limitation, the matrix material of the drug loaded core can be any desired material. For example, the matrix material can be a polymeric material. In some embodiments, the core matrix material comprises one or more polymers independently selected from the group consisting of a polyester, a polycarbonate, a polyamide, a polyether, a polyanhydride, polyacrylate, polyurethane, and a copolymer thereof. In some embodiments, the core matrix material comprise one or more polymers independently selected from the group consisting of poly (caprolactone), poly(lactide-co-glycolide), and poly(glycerol monostearate-co-caprolactone), polyurethane, polyurea, collagen, hyaluronic acid, dextran, alginate, fibrin, alginate, PDMS, cellulose, and hydroentangled cellulose and polyester mesh.

In some embodiments, the core matrix material comprises or is made from a hydrophilic material. In some other embodiments, the core matrix material comprises or is made from a hydrophobic material.

In some embodiments, the drug loaded core comprises an absorbent material and the drug is absorbed thereon or therein. The term "absorbent material" as used herein refers to materials that receive and contain fluids.

In some embodiments, the core matrix can be porous. For example, the matrix can have a porosity of at least about 10%, at least about 20%, at least about 30%, at least about 40%, at least about 50%, at least about 60%, at least about 70%, at least about 80%, at least about 90%, or higher (up to and including 99%). As used herein, the term "porosity" is a measure of void spaces in a material and is a fraction of volume of voids over the total volume, as a percentage between 0 and about 99% (or between 0 and 0.99). Determination of porosity is well known to a skilled artisan, e.g., using standardized techniques, such as mercury porosimetry and gas adsorption, e.g., nitrogen adsorption. The porous matrix can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In porous matrix, the drug can be present in the pores, in the matrix material, or a combination of the pores and matrix material.

When the drug loaded core comprises two or more different surfaces, each surface can be coated with a hydrophobic or superhydrophobic coating layer or only some (e.g., one, two, three, up to all but one) surfaces can be coated with the coating layer. Without limitations, each coating layer can be the same, all different, or some same and some different.

In some embodiments, the drug loaded core is a multi-layer structure. For example a multilayered film or a multilayered particle. In the multilayered drug loaded core, each layer can be the same, all different or some same and some different. Further, all layers can comprises the same drug, all different drugs, or some same and some different.

Without limitation, the drug-delivery device described herein can be any shape or form. For example, the drug delivery device can be in the form of, but not limited, to cylindrical (i.e., tube or rod), circular or spherical, rectangular, cubic, polyhedron, prism, disc, other geometric shape, or any combination thereof. In some embodiments, the drug delivery device is in form of an implant or an implantable drug delivery device.

In some embodiments, a drug delivery device disclosed herein can be implemented on a balloon catheter or a stent. In some embodiments, the drug delivery device itself is a balloon catheter or a stent. For example, a surface of the balloon catheter or the stent can be coated with a tension responsive coating layer. In some embodiments, a surface of the balloon catheter or the stent can be coated with a drug loaded core followed by a tension responsive coating layer. Balloon catheters and stents exhibit radial extension in order to unblock blood vessels. The radial extension can provide the tension to the tension responsive coating layer there by releasing the drug from the drug loaded core.

The drug delivery device disclosed herein can also be incorporated into expandable or extendable medical devices. These expandable or extendable medical devices can serve as an external mechanical stimulus for the tension-responsive drug delivery device incorporated therein.

In one non-limiting example, the tension-responsive drug delivery system can be implemented onto gastric bands that can reversibly expand with ingestion. For example, a drug-delivery device disclosed herein can be implemented on a surface of a gastric band. In some other embodiments, a drug can be incorporated into the gastric band and a surface of the gastric band can be coated with a tension responsive coating layer. In some other embodiments, a surface of the gastric band can be coated with a layer of drug loaded core and a tension responsive coating layer formed on the drug loaded core layer. The incorporated system can deliver increased drug, protein, or cytokines upon expansion, in tune with physiological responses.

In some embodiments, the tension-responsive drug delivery devices can incorporated into a cell scaffold or implantable material used in tissue expanders. Tissue expanders, as may be found in the breast, have step-wise increases in tension/strain/expansion. A tension-responsive drug delivery device incorporated into these scaffolds can therefore deliver increasing amounts of drug as time/tension/expansion increases over time.

In embodiments of the drug delivery device described herein, the coating layer and the core have different mechanical properties. For example, the coating layer and the core can have different Young's modulus, tensile strength, fracture toughness, has compressive strength, compressive toughness or compressive elastic modulus.

Compressive elastic modulus is the mathematical description of the tendency of a material to be deformed elastically (i.e. non-permanently) when a force is applied to it. The Young's modulus (E) describes tensile elasticity, or the tendency of a material to deform along an axis when opposing forces are applied along that axis; it is defined as the ratio of tensile stress to tensile strain (measured in MPa) and is otherwise known as a measure of stiffness of the material. The elastic modulus of an object is defined as the slope of the stress-strain curve in the elastic deformation region.

Generally, the modulus of the coating can range from about 0.01 MPa to about 1 MPa. For example, modulus of the coating can be from about 0.1 MPa to about 0.8 MPa, from about 0.15 MPa to about 0.75 MPa, from about 0.25 MPa to about 0.5 MPa or from about 0.3 MPa to about 0.4 MPa. In some embodiments, the modulus of the coating can be about 0.35 MPa.

In some embodiments, the coating layer has a lower compressive elastic modulus relative to the core. For example, the coating layer can have a compressive elastic modulus that is 90%, 85%, 80%, 75%, 70%, 65%, 60%, 55%, 50%, 45%, 40%, 35%, 30%, 25%, 20%, 15%, 10%, 5%, 2.5%, 2%, 1.5%, 1% or lower of the compressive elastic modulus of the core.

In some embodiments, the coating layer has a higher compressive elastic modulus relative to the core. For example, the coating layer can have a compressive elastic modulus that is 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 2-fold, 2.5-fold, 5-fold, 10-fold or higher than the compressive elastic modulus of the core.

In some embodiments, the core has a higher compressive elastic modulus relative to the coating layer. For example, the core can have a compressive elastic modulus that is 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 2-fold, 2.5-fold, 5-fold, 10-fold or higher than the compressive elastic modulus of the coating layer.

In some embodiments, the core has a lower compressive elastic modulus relative to the coating layer. For example, the core can have a compressive elastic modulus that is 90%, 85%, 80%, 75%, 70%, 65%, 60%, 55%, 50%, 45%, 40%, 35%, 30%, 25%, 20%, 15%, 10%, 5%, 2.5%, 2%, 1.5%, 1% or lower of the compressive elastic modulus of the coating layer.

Generally, the elastic modulus of the device itself can range from about 1 kPa to about 150 kPa. For example, the drug delivery device can have an elastic modulus of from about 5 kPa to about 100 kPa. In some embodiments, the drug delivery device can have an elastic modulus of from about 10 kPa to about 75 kPa., from about 25 kPa to about 50 kPa, from about 25 kPa to about 40 kPa, or from about 3 kPa to about 35 kPa. In one embodiment, the drug delivery device can have an elastic modulus of about 33 kPa.

Compressive toughness is the capacity of a material to resist fracture when subjected to axially directed pushing forces. By definition, the compressive toughness of a material is the ability to absorb mechanical (or kinetic) energy up to the point of failure. Toughness is measured in units of joules per cubic meter ($Jm^{-3}$) and can be measured as the area under a stress-strain curve. In some embodiments, the coating layer has a lower compressive toughness relative to the core. For example, the coating layer can have a compressive toughness that is 90%, 85%, 80%, 75%, 70%, 65%, 60%, 55%, 50%, 45%, 40%, 35%, 30%, 25%, 20%, 15%, 10%, 5% or lower of the compressive toughness of the core. In some embodiments, the coating layer can have a compressive toughness of from about 70% to about 90%, from about 40% to about 65%, from about 5% to about 25% of the compressive toughness of the core Compressive strength is the capacity of a material to withstand axially directed pushing forces. By definition, the compressive strength of a material is that value of uniaxial compressive stress reached when the material fails completely. A stress-strain curve is a graphical representation of the relationship between stress derived from measuring the load applied on the sample (measured in MPa) and strain derived from measuring the displacement as a result of compression of the sample. The ultimate compressive strength of the material can depend upon the target site of implantation. In some embodiments, the coating layer has a lower compressive strength relative to the core. For example, the coating layer can have a compressive strength that is 90%, 85%, 80%, 75%, 70%, 65%, 60%, 55%, 50%, 45%, 40%, 35%, 30%, 25%, 20%, 15%, 10%, 5% or lower of the compressive strength of the core. In some embodiments, the coating layer can have a compressive strength that is from about 1% to about 25% or from about 30% to about 60% of the compressive strength of the core.

Any desired material or molecule or agent can be incorporated into the drug loaded core or the coating layer. Acceptable agents include, but are not limited to, chemotherapeutic agents, such as radiosensitizers, receptor inhibitors and agonists or other anti-neoplastic agents; immune modulators and bioactive agents, such as cytokines, growth factors, or steroids with or without the co-incorporation of tumor or pathogen antigens to increase the anti-neoplastic response as a means of vaccine development; local anesthetic agents; antibiotics; or nucleic acids as a means of local gene therapy. In vitro cell assays on cancer cell lines demonstrate our ability to load and release a therapeutic amount of cisplatin. Here we show the development of superhydrophobic coatings using the electrospraying technique to achieve contact angles as great as 167° and demonstrate the ability to release a drug payload upon mechanical tension.

This study has shown that the wettability of the absorbent drug-loaded matrix is dependent on the thickness of the coating, and requires a difference in strain of the materials to achieve mechanically-stimulated release. The latter is accomplished through electrospun coatings of the same material; instead of discrete particles, fibers can be subjected to higher strain without breaking, preventing drug release despite mechanical stimulation.

Without limitation, the drug loaded core can be in the form of a film, a particle, a mesh, a fiber, a gel, a hydrogel, a foam, a mesh, a mat, a non-woven mat. In some embodiments, the drug loaded core is in the form of a film, a particle or a mesh.

Any agent can be incorporated within the drug loaded core described herein. For example, a polymer film or particle described herein can incorporate a pharmaceutical agent selected from among (1) nonsteroidal anti-inflammatory drugs (NSAIDs) analgesics, such as diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) anti-anaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous beta-lactam antibiotic anti-infectives, such as aztreonam and imipenem; (11) penicillin antibiotic anti-infectives, such as nafcillin, oxacillin, penicillin G, and penicillin V; (12) quinolone antibiotic anti-infectives, such as ciprofloxacin and norfloxacin; (13) tetracycline antibiotic anti-infectives, such as doxycycline, minocycline, and tetracycline; (14) antituberculosis antimycobacterial anti-infectives such as isoniazid (INH), and rifampin; (15) antiprotozoal anti-infectives, such as atovaquone and dapsone; (16) antimalarial antiprotozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon alpha, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antimetabolite antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide (VP-16), interferon alpha, paclitaxel, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) alpha-blocker sympatholytics, such as prazosin; (34) beta-blocker sympatholytics, such as atenolol; (35) adrenergic agonist sympathomimetics, such as albuterol and dobutamine; (36) cardiovascular agents, such as aspirin (ASA), plavix (Clopidogrel bisulfate) etc; (37) beta-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as digoxin; (41) class I anti-arrhythmics, such as lidocaine, mexiletine, phenytoin, procainamide, and quinidine; (42) class II antiarrhythmics, such as atenolol, metoprolol, propranolol, and timolol; (43) class III antiarrhythmics, such as amiodarone; (44) class IV antiarrhythmics, such as diltiazem and verapamil; (45) alpha-blocker antihypertensives, such as prazosin; (46) angiotensin-converting enzyme inhibitor (ACE inhibitor) antihypertensives, such as captopril and enalapril; (47) beta blocker antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as hydralazine and minoxidil; (52) antilipemics, such as gemfibrozil and probucol; (53) bile acid sequestrant antilipemics, such as cholestyramine; (54) HMG-CoA reductase inhibitor antilipemics, such as lovastatin and pravastatin; (55) inotropes, such as amrinone, dobutamine, and dopamine; (56) cardiac glycoside inotropes, such as digoxin; (57) thrombolytic agents or enzymes, such as alteplase (TPA), anistreplase, streptokinase, and urokinase; (58) dermatological agents, such as colchicine, isotretinoin, methotrexate, minoxidil, tretinoin (ATRA); (59) dermatological corticosteroid anti-inflammatory agents, such as betamethasone and dexamethasone; (60) antifungal topical antiinfectives, such as amphotericin B, clotrimazole, miconazole, and nystatin; (61) antiviral topical anti-infectives, such as acyclovir; (62) topical antineoplastics, such as fluorouracil (5-FU); (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes such as RNase and DNase; (69) immunosupressive agents, such as cyclosporine, steroids, methotrexate tacrolimus, sirolimus, rapamycin; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) H$_2$-blocker anti-ulcer agents, such as cimetidine, famotidine, nizatidine, and ranitidine; (74) digestants, such as pancrelipase; (75) prokinetic agents, such as erythromycin; (76) opiate agonist intravenous anesthetics such as fentanyl; (77) hematopoietic antianemia agents, such as erythropoietin, filgrastim (G-CSF), and sargramostim (GM-CSF); (78) coagulation agents, such as antihemophilic factors 1-10 (AHF 1-10); (79) anticoagulants, such as warfarin, heparin, and argatroban; (80) growth receptor inhibitors, such as erlotinib and gefetinib; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadatropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin IM, IMIG, IGIM and immune globulin IV, WIG, IGIV; (94) amide local anesthetics, such as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs (NSAIDs), such as diclofenac, ibuprofen, ketoprofen, ketorlac, and naproxen; (99) skeletal muscle relaxants, such as baclofen, cyclobenzaprine, and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-parkisonian agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) beta-blocker anti-glaucoma agents, such as timolol; (110) miotic anti-glaucoma agents, such as pilocarpine; (111) ophthalmic aminoglycoside antiinfectives, such as gentamicin, neomycin, and tobramycin; (112) ophthalmic quinolone anti-infectives, such as ciprofloxacin, norfloxacin, and ofloxacin; (113) ophthalmic corticosteroid anti-inflammatory agents, such as dexamethasone and prednisolone; (114) ophthalmic nonsteroidal anti-inflammatory drugs (NSAIDs), such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) antitussives, such as codeine; (119) bronchodilators, such as theophylline; (120) adrenergic agonist bronchodilators, such as albuterol; (121) respiratory corticosteroid anti-inflammatory agents, such as dexamethasone; (122) antidotes, such as flumazenil and naloxone; (123) heavy metal antagonists/chelating agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; (129) vitamin D compounds, such as calcitriol; (130) vitamin A, vitamin E, and vitamin E compounds; (131) poisons, such as racin; (132) anti-bleeding agents, such as protamine; (133) antihelminth anti-infectives, such as metronidazole; and (134) sclerosants such as talc, alcohol, and doxycyclin.

In addition to the foregoing, the following less common drugs can also be used: chlorhexidine; estradiol cypionate in oil; estradiol valerate in oil; flurbiprofen; flurbiprofen sodium; ivermectin; levodopa; nafarelin; and somatropin. Further, the following drugs can also be used: recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-la; lenograstim (G-CSF); olanzapine; recombinant thyroid stimulating hormone (r-TSH); and topotecan. Further still, the following intravenous products can be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alpha; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT).

Further specific examples of useful pharmaceutical agents from the above categories include: (a) anti-neoplastics such as androgen inhibitors, antimetabolites, cytotoxic agents, receptor inhibitors, and immunomodulators; (b) anti-tussives such as dextromethorphan, dextromethorphan hydrobromide, noscapine, carbetapentane citrate, and chlorphedianol hydrochloride; (c) antihistamines such as chlorpheniramine maleate, phenindamine tartrate, pyrilamine maleate, doxylamine succinate, and phenyltoloxamine citrate; (d) decongestants such as phenylephrine hydrochloride, phenylpropanolamine hydrochloride, pseudoephedrine hydrochloride, and ephedrine; (e) various alkaloids such as codeine phosphate, codeine sulfate and morphine; (I) mineral supplements such as potassium chloride, zinc chloride, calcium carbonates, magnesium oxide, and other alkali metal and alkaline earth metal salts; (g) ion exchange resins such as cholestryramine; (h) anti-arrhythmics such as N-acetylprocainamide; (i) antipyretics and analgesics such as acetaminophen, aspirin and ibuprofen; (j) appetite suppressants such as phenyl-propanolamine hydrochloride or caffeine; (k) expectorants such as guaifenesin; (l) antacids such as aluminum hydroxide and magnesium hydroxide; (m) biologicals such as peptides, polypeptides, proteins and amino acids, hormones, interferons or cytokines, and other bioactive peptidic compounds, such as inter-leukins 1-18 including mutants and analogues, RNase, DNase, luteinizing hormone releasing hormone (LHRH) and analogues, gonadotropin releasing hormone (GnRH), transforming growth factor-β. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morpho genetic proteins 1-7 (BMP 1-7), somatostatin, thymosin-alpha-1, gamma-globulin, superoxide dismutase (SOD), complement factors, hGH, tPA, calcitonin, ANF, EPO and insulin; (n) anti-infective agents such as antifungals, anti-virals, antihelminths, antiseptics and antibiotics; and (m) oxygen, hemoglobin, nitric or sliver oxide Non-limiting examples of broad categories of useful pharmaceutical agents include the following therapeutic categories: anabolic agents, anesthetic agents, antacids, anti-asthmatic agents, anticholesterolemic and anti-lipid agents, anti-coagulants, anti-convulsants, anti-diarrheals, antiemetics, anti-infective agents, anti-inflammatory agents, anti-manic agents, anti-nauseants, antineoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, stimulants, thyroid and antithyroid agents, uterine relaxants, vitamins, and prodrugs.

Examples of specific drugs that can be used include: asparaginase, bleomycin, busulfan, capecitabine, carboplatin, carmustine, chlorambucil, cisplatin, cyclophosphamide, cytarabine, dacarbizine, dactinomycin, daunorubicin, dexrazoxane, docetaxel, doxorubicin, etoposide, floxuridine, fludarabine, fluoruracil, gemcitabine, hydroxyurea, idarubicin, ifosfamide, irinotecan, lomustine, mechlorethamine, melphalan, mercaptopurine, methotrexate, mitomycin, mitotane, mitoxantrone, paclitaxel, pentostatin, plicamycin, premextred procarbazine, rituximabe, streptozocin, teniposid, thioguanine, thiotepa, vinplastine, vinchristine, and vinorelbine. In some embodiments, the drugs for lung cancer treatment is paclitaxel, pemetrexed, 10-hydrocamptothecin, irinotecan, erlotinibil/gefetinib or derivates of these molecules.

Examples of anticancer, antineoplastic agents are camptothecins. These drugs are antineoplastic by virtue of their ability to inhibit topoisomerase I. Camptothecin is a plant alkaloid isolated from trees indigenous to China and analogs thereof such as 9-aminocamptothecin, 9-nitrocamptothecin, 10-hydroxycamptothecin, 10,11-methylenedioxycamptothecin, 9-nitro-10,11-methylenehydroxycamptothecin, 9-chloro-10,11-methylenehydroxycamptothecin, 9-amino-10,11-methylenehydroxycamptothecin, 7-ethyl-10-hydroxycamptothecin (SN-38), topotecan, DX-8951, Lurtotecan (GII147221C), and other analogs (collectively referred to herein as camptothecin drugs) are presently under study worldwide in research laboratories for treatment of colon, breast, and other cancers.

Additionally, the pharmaceutical agent can be a radiosensitizer, such as metoclopramide, sensamide or neusensamide (manufactured by Oxigene); profiromycin (made by Vion); RSR13 (made by Allos); THYMITAQ® (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by Terrapin); agents that minimize hypoxia, and the like.

The agent can be selected from a biologically active substance. The biologically active substance can be selected from the group consisting of peptides, poly-peptides, proteins, amino acids, polysaccharides, growth factors, hormones, anti-angiogenesis factors, interferons or cytokines, elements, and pro-drugs. In useful embodiments, the biologically active substance is a therapeutic drug or pro-drug, in some embodiments, a drug selected from the group consisting of chemotherapeutic agents and other antineoplastics such as paclitaxel, antibiotics, anti-virals, antifungals, anesthetics, antihelminths, anti-inflammatories, and anticoagulants. In certain useful embodiments, the therapeutic drug or pro-drug is selected from the group consisting of chemotherapeutic agents and other antineoplastics such as paclitaxel, carboplatin and cisplatin; nitrosourea alkylating antineoplastic agents, such as carmustine (BCNU); fluoruracil (5-FU) and gemcitabine; hormonal antineoplastics, such as goserelin, leuprolide, and tamoxifen; receptor inhibitors such as erlotinib, gefetinib, sutent or anti-ckit inhibitors, such as GLEEVEC®; natural antineoplastics, such as aldesleukin, interleukin-2, docetaxel, etoposide (VP-16), interferon alpha, paclitaxel, and tretinoin (ATRA).

In another embodiment, the biologically active substance is a nucleic acid sequence. The nucleic acid sequence can be selected from among any DNA or RNA sequence. In certain embodiments, the biologically active substance is a DNA sequence that encodes a genetic marker selected from among luciferase gene, β-galactosidase gene, resistance, neomycin resistance, and chloramphenicol acetyl transferase. In certain embodiments, the biologically active substance is a DNA sequence that encodes a lectin, a mannose receptor, a sialoadhesin, or a retroviral transactivating factor. In certain embodiments, the biologically active substance is a DNA sequence that encodes a RNA selected from the group consisting of a sense RNA, an antisense RNA, siRNA and a ribozyme.

Biologically active agents amenable for use with drug delivery device described herein include, without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Useful active agents amenable for use in the new compositions include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are preferred. Members of the TGF supergene family include the beta-transforming growth factors (for example, TGF-b1, TGF-b2, and TGF-b3); bone morphogenetic proteins (for example, BMP-1, BMP-2, BMP-3, BMP-4, BMP-5, BMP-6, BMP-7, BMP-8, and BMP-9); heparin-binding growth factors (for example, fibroblast growth factor (FGF), epidermal growth factor (EGF), platelet-derived growth factor (PDGF), and insulin-like growth factor (IGF)); inhibins (for example, Inhibin A, Inhibin B); growth differentiating factors (for example, GDF-1); and activins (for example, Activin A, Activin B, and Activin AB).

In some embodiments, each of the bioactive agents is independently selected from the group consisting of an antibiotic, an antimitotic, an anti-inflammatory agent, a growth factor, a targeting compound, a cytokine, an immunotoxin, an anti-tumor antibody, an anti-angiogenic agent, an anti-edema agent, a radiosensitizer, and a chemotherapeutic. In some embodiments, at least one of the one or more independently selected bioactive agents is camptothecin. In some embodiments, at least one of the one or more independently selected bioactive agents is 10-hydroxycamptothecin. In some embodiments, at least one of the one or more independently selected bioactive agents is paclitaxel.

In some embodiments, at least one of the one or more independently selected bioactive agents is a platinum containing molecule. In some embodiments, the platinum containing molecule is selected from the group consisting of cisplatin and carboplatinum.

While the drug loaded core is described as comprising a drug, other materials or molecules of interest can also be loaded in the core. Accordingly, in some embodiments, the core comprises an imaging agent or contrast agent. As used herein, the term "imaging agent" refers to an element or functional group in a molecule that allows for the detection, imaging, and/or monitoring of the presence and/or progression of a condition(s), pathological disorder(s), and/or disease(s). The imaging agent may be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p (2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H,15H-Xantheno [2,3,4-ij:5,6,7-i'j']diquinolizin-18-ium, 9-[2 (or 4)-[[[6-[2,5-dioxo-l-pyrrolidinyl)oxy]-6-oxohexyl]amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, *Mol. Microbiol,* 55:1767-1781 (2005), the GFP variant described in Crameri et al, *Nat. Biotechnol.,* 14:315319 (1996), the cerulean fluorescent proteins described in Rizzo et al, *Nat. Biotechnol,* 22:445 (2004) and Tsien, *Annu. Rev. Biochem.,* 67:509 (1998), and the yellow fluorescent protein described in Nagal et al, *Nat. Biotechnol.,* 20:87-90 (2002). DsRed variants are described in, e.g., Shaner et al, *Nat. Biotechnol.*, 22:1567-1572 (2004), and include mStrawberry, mCherry, mOrange, mBanana, mHoneydew, and mTangerine. Additional DsRed variants are described in, e.g., Wang et al, *Proc. Natl. Acad. Sci. U.S.A.*, 101:16745-16749 (2004) and include mRaspberry and mPlum. Further examples of DsRed variants include mRFPmars described in Fischer et al, *FEBS Lett.*, 577:227-232 (2004) and mRFPruby described in Fischer et al, *FEBS Lett*, 580:2495-2502 (2006).

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane. Suitable non-metallic isotopes include, but are not limited to, $^{11}$C, $^{14}$C, $^{13}$N, $^{18}$F, $^{123}$I, $^{124}$I, and $^{125}$I. Suitable radioisotopes include, but are not limited to, $^{99m}$Tc, $^{95}$Tc, $^{111}$In, $^{62}$Cu, $^{64}$Cu, Ga, $^{68}$Ga, and $^{153}$Gd. Suitable paramagnetic metal ions include, but are not limited to, Gd(III), Dy(III), Fe(III), and Mn(II). Suitable X-ray absorbers include, but are not limited to, Re, Sm, Ho, Lu, Pm, Y, Bi, Pd, Gd, La, Au, Au, Yb, Dy, Cu, Rh, Ag, and Ir.

It is to be understood that the core can comprise two or more different drugs and/or other molecules of interest.

In some embodiments, the drug delivery device is comprised of two or more layers of polymer matrix, wherein at least two different layers exhibit a discrepancy in mechanical properties such that upon mechanical stimulation, such as tension, shear force, compression, and/or ultrasound, the weaker layer fractures to either direct diffusion of contained agents, cause an infiltration of water and subsequent drug diffusion, or a combination thereof.

The drug-delivery device can be used to provide tunable drug release. As used herein, "tunable drug release" refers to the ability to reduce either the cumulative amount of released drug over a fixed time period by at least 20 percent, or the ability to alter the rate of drug release over a fixed time period by at least 20 percent, or both.

Accordingly, in another aspect, the disclosure provides a method for controlling the release of a drug or other molecule of interest from the drug delivery device described herein. Generally the method comprises applying a mechanical force to the drug delivery device. The mechanical force is of sufficient magnitude or duration to induce a permanent deformation in the coating layer. For example, upon application of the mechanical force, the coating layer can break down through crack propagation. This can lead to water or other fluid infiltrating the drug loaded core to release the drug or other molecule of interest from the core.

In some embodiments, the mechanical force can be selected from the group consisting of tension, shear force, compression, ultrasound, and any combinations thereof. In some embodiments, the mechanical force is tension. Tension can be applied by stretching the drug delivery device. In one non-limiting example, the force for releasing the agent can be applied by chewing the delivery device.

The ultrasound intensity can be from about 0.1 W/cm$^{-2}$ to about 1500 W/cm$^{-2}$. In some embodiments, the ultrasound intensity is equal to or less than about 1000 W/cm$^{-2}$, 975 W/cm$^{-2}$, 950 W/cm$^{-2}$, 925 W/cm$^{-2}$, 900 W/cm$^{-2}$, 875 W/cm$^{-2}$, 850 W/cm$^{-2}$, 825 W/cm$^{-2}$, 800 W/cm$^{-2}$, 775 W/cm$^{-2}$, 750 W/cm$^{-2}$, 725 W/cm$^{-2}$, 700 W/cm$^{-2}$, 675 W/cm$^{-2}$, 650 W/cm$^{-2}$, 625 W/cm$^{-2}$, 600 W/cm$^{-2}$, 575 W/cm$^{-2}$, 550 W/cm$^{-2}$, 525 W/cm$^{-2}$, 500 W/cm$^{-2}$, 475 W/cm$^{-2}$, 450 W/cm$^{-2}$, 425 W/cm$^{-2}$, 400 W/cm$^{-2}$, 375 W/cm$^{-2}$, 350 W/cm$^{-2}$, 325 W/cm$^{-2}$, 300 W/cm$^{-2}$, 275 W/cm$^{-2}$, 250 W/cm$^{-2}$, 225 W/cm$^{-2}$, 200 W/cm$^{-2}$, 175 W/cm$^{-2}$, 150 W/cm$^{-2}$, 125 W/cm$^{-2}$, 100 W/cm$^{-2}$, 75 W/cm$^{-2}$, 50 W/cm$^{-2}$, 25 W/cm$^{-2}$, 20 W/cm$^{-2}$, 15 W/cm$^{-2}$, 10 W/cm$^{-2}$, 7.5 W/cm$^{-2}$, 5 W/cm$^{-2}$, or 2.5 W/cm$^{-2}$. In some embodiments, the ultrasound intensity can be between 0.1 W/cm$^{-2}$ and 20 W/cm$^{-2}$; between 0.5 W/cm$^{-2}$ and 15 W/cm$^{-2}$; or between 1 W/cm$^{-2}$ and 10 W/cm$^{-2}$.

In some embodiments, the release can be achieved in a pulsatile manner by repeated application of a mechanical force. For example, the mechanical force is of such a magnitude or duration that only a small deformation of the coating layer takes place and only a portion of the drug in core is released. A second application of the mechanical force, which can be the same as the force applied the first time, then further deforms the coating layer, thereby releasing additional drug from the core. This ability for on-demand pulsatile release of drugs is useful in a variety of settings, including immunizations, which typically provide an initial immunization, followed by distinct booster doses at later times. Moreover, repeated administration of well-defined doses of allergen, in the absence of immune-stimulatory molecules, from the drug delivery device can be useful for inducing tolerance. It also can be advantageous to use an mechanical force to deliver drugs in a pulsatile manner so as to time the delivery to coincide with a particular biological event (e.g. the circadian rhythm) in order to maximize the effectiveness of the drug (e.g. against tumors).

In some embodiments, the drug-delivery device is in vivo when the mechanical force is applied to it. For example, the device can be in a mammal when the mechanical force is applied to it. Without limitations, the mammal can be a human or a non-human primate, mouse, rat, dog, cat, horse, or cow, but is not limited to these examples.

In various embodiments, the release (e.g., rate or amount) of the agent from the drug-delivery device can be controlled by varying the material of the coating layer, thickness of the coating layer, magnitude of the mechanical force applied, duration of the mechanical force, and any combinations thereof. Generally, the drug-delivery device release very little or no drug in absence of the mechanical force. Further, a mechanical force of a lower magnitude releases the drug at a lower rate or amount relative to a mechanical force of a higher magnitude. As show in the various examples, the drug release with application of 30% strain to the drug-delivery device is lower than application of 100% strain.

The release (e.g., rate or amount) of the agent from the drug-delivery device can be controlled by modulating the interactions of the agent with the core matrix material and/or the coating. Generally, the agent can be present freely in the core matrix material or bound covalently or non-covalently with the matrix material. Non-covalent interactions include, but are not limited to, hydrophobic interactions, ionic interactions, hydrogen bonding, van der Waals interactions, dipole-dipole interactions, electrostatic interactions, shape recognition interactions, ionic charge complex formation, π-π interactions, and host guest interaction (e.g., cyclodextrin/adamantine). The strength of the interactions can be modulated to modulate the release. Stronger interactions lowering/decreasing the release.

In some embodiments, the agent can be covalently linked with the core matrix material, e.g., via a linker. As used herein, the term "linker" means an organic moiety that connects two parts of a compound. Linkers typically comprise a direct bond or an atom such as oxygen or sulfur, a unit such as NH, C(O), C(O)NH, SO, SO$_2$, SO$_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, C(O). In some embodiments, the linker can be a branched linker. The branch point of the branched linker may be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branch point is glycerol or derivative thereof, and normal chain sugars such as monosaccharides and polysaccharides.

Generally, the linker comprises at least one cleavable linking group. A cleavable linking group is one which is sufficiently stable under a first condition, but which is cleaved under a second condition to release the two parts the linker is holding together. In a preferred embodiment, the cleavable linking group is cleaved at least 10 times or more, preferably at least 100 times faster under a first reference than under a second reference condition.

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases. The cleavable linking group can comprise esters, peptides, carbamates, acid-labile, reduction-labile, oxidation-labile, disulfides, and modifications thereof.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid celavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.0 5.5, 5.0, or lower), or by agents such as enzymes that can act as a general acid.

In some embodiments, the linker comprises an acid labile group, e.g., hydrazone or carbamate. In some embodiments, the linker comprises an enzyme labile group e.g., maleimidecaproyl-valyl-citrullinyl-p-aminobenzylcarbamate.

Without wishing to be bound by a theory, inducing cracks or crack propagation in the coating can allow a reagent or cleavage agent to enter the core and thereby cleaving the agent from the matrix material. The amount of the cleavage agent entering the core can be controlled by controlling the number and/or size of the cracks by varying the magnitude or duration of the mechanical force applied.

In some embodiments, a stepwise release of the drug can be accomplished by applying a mechanical force of first magnitude followed by a applying a mechanical force of second magnitude. The first magnitude is smaller than the second magnitude and releases the drug at a lower rate and/or amount. The second magnitude is higher than the first magnitude and releases the drug release at a higher rate and/or amount from the drug-delivery device.

In some embodiments, by altering the mechanical force, such as strain, drug release can be controlled in order to provide a range of concentrations at fixed time points. The concentration of the drug can be either lower or higher than the $IC_{50}$ value such that similar dosage regimes can be created using force and/or strain, rather than, or in addition to, concentration.

Exemplary embodiments of the various aspects disclosed herein can be described by one or more of the following numbered paragraphs:

Paragraph 1: A drug-delivery device comprising a core and a superhydrophobic coating layer on at least one surface of the core, wherein the core comprises an agent distributed in a matrix material, and wherein the core and the coating layer have at least one mechanical property that is different.

Paragraph 2. The drug-delivery device of paragraph 1, wherein the coating layer has a contact angle of 150° or higher.

Paragraph 3: The drug-delivery device of paragraph 1 or 2, wherein the coating layer has a thickness of from about 10 µm to about 5,000 µm.

Paragraph 4: The drug-delivery device of any of paragraphs 1-3, wherein the coating layer has high surface roughness.

Paragraph 5: The drug-delivery device of any of paragraphs 1-4, wherein the an average surface roughness (Ra) of about 50 nm to about 250 nm, as measured on a 5 µm×5 µm area.

Paragraph 6: The drug-delivery device of any of paragraphs 1-5, wherein the coating layer is composed of particles.

Paragraph 7: The drug-delivery device of paragraph 6, wherein the particles have a size of from about 100 nm to about 25 µm.

Paragraph 8: The drug-delivery device of any of paragraphs 1-7, wherein the coating layer is multilayered.

Paragraph 9: The drug-delivery device of any of paragraphs 1-8, wherein the coating layer comprises a material selected from the group consisting of polyesters, polycarbonates, polyamides, polyethers, polyanhydrides, polyacrylates, copolymers thereof, and any mixtures thereof.

Paragraph 10: The drug-delivery device of any of paragraphs 1-9, wherein the coating layer comprises a material selected from the group consisting of poly (caprolactone), poly(lactide-co-glycolide), poly(glycerol monostearate-co-caprolatone), and any mixtures thereof.

Paragraph 11: The drug-delivery device of any of paragraphs 1-10, wherein the coating layer comprises poly (caprolactone) and poly(glycerol monostearate-co-caprolatone).

Paragraph 12: The drug-delivery device of any of paragraphs 1-11, wherein the coating layer has a lower compressive toughness relative to the core.

Paragraph 13: The drug-delivery device of any of paragraphs 1-12, wherein the coating layer has a lower compressive strength relative to the core.

Paragraph 14: The drug-delivery device of any of paragraphs 1-13, wherein the coating layer has a lower compressive elastic modulus relative to the core.

Paragraph 15: The drug-delivery device of any of paragraphs 1-14, wherein the core is in the form of a a film, a particle, a mesh, a fiber, a gel, a hydrogel, a foam, a mesh, a mat, a non-woven mat, or any combinations thereof.

Paragraph 16: The drug-delivery device of any of paragraphs 1-15, wherein the matrix material of the core is porous.

Paragraph 17: The drug-delivery device of any of paragraphs 1-16, wherein the matrix material of the core is comprised of an absorbent material.

Paragraph 18: The drug-delivery device of any of paragraphs 1-17, wherein the matrix material of the core comprises a material selected from the group consisting of polyesters, polycarbonates, polyamides, polyethers, polyanhydrides, polyacrylates, polyurethanes, and mixture or copolymers thereof.

Paragraph 19: The drug-delivery device of any of paragraphs 1-18, wherein the matrix material of the core comprises poly(caprolactone), poly(lactide-co-glycolide), poly(glycerol monostearate-co-caprolactone), polyurethane, polyurea, collagen, hyaluronic acid, dextran, alginate, fibrin, alginate, PDMS, cellulose, hydroentangled cellulose, polyester mesh, or any combinations thereof.

Paragraph 20: The drug-delivery device of any of paragraphs 1-19, wherein the core is comprises a multilayered structure.

Paragraph 21: The drug-delivery device of any of paragraphs 1-20, wherein the drug-delivery device is cylindrical (i.e., tube or rod), circular or spherical, rectangular, cubic, polyhedron, prism, disc, other geometric shape, or any combinations thereof.

Paragraph 22: The drug-delivery device of any of paragraphs 1-21, wherein the in form of an implant or an implantable device.

Paragraph 23: The drug-delivery device of any of paragraphs 1-22, wherein the drug-delivery device is a balloon catheter or a stent.

Paragraph 24: The drug-delivery device of any of paragraphs 1-23, wherein the drug-delivery device is part of a cell scaffold or an implantable material used in a tissue expander.

Paragraph 25: The drug-delivery device of any of paragraphs 1-24, wherein the drug-delivery device is a gastric band.

Paragraph 26: The drug-delivery device of any of paragraphs 1-25, wherein the agent is selected from the group consisting of small organic or inorganic molecules, peptides, peptide analogs and derivatives, peptidomimetics, proteins, antibodies, antigen or epitope binding fragments of antibodies, nucleic acids, nucleic acid analogs and derivatives, an extract made from biological materials, and any combinations thereof.

Paragraph 27: The drug-delivery device of any of paragraphs 1-26, wherein the agent is selected from the group consisting of chemotherapeutic agents, radiosensitizers, receptor inhibitors and agonists, anti-neoplastic agents; immune modulators, cytokines, growth factors, or steroids with or without the co-incorporation of tumor or pathogen antigens, anesthetic agents; antibiotics, imaging agents, and any combinations thereof.

Paragraph 28: A method for controlling the release of an agent, the method comprising: (a) providing a drug-delivery device of any of paragraphs 1-27; and (b) applying a mechanical force on the drug delivery device.

Paragraph 29: The method of paragraph 28, wherein said mechanical force is selected from the group consisting of tension, shear force, compression, ultrasound, and any combinations thereof.

Paragraph 30: The method of paragraph 28 or 29, wherein said mechanical force induces cracks or crack propagation in the coating layer.

Paragraph 31: The method of any of paragraphs 28-30, wherein the drug-delivery device is in vivo.

Paragraph 32: The method of any of paragraphs 28-31, wherein the drug-delivery device is in a mammal.

Applications of the drug delivery devices and methods described herein can include, but are not limited to, their use in transarterial or intrathoracic drug, protein, or cytokine administration. Expandable and extendable medical devices can serve as an external mechanical stimulus for the tension-responsive drug delivery device described herein.

In one such embodiment, a tension-responsive device or tension-responsive coating can be implemented onto a balloon catheter for angioplasty. In another embodiment, the tension-responsive coating can be applied to a stent. In these two embodiments, where stents and balloon catheters both exhibit an instantaneous radial extension in order to unblock blood vessels, the tension-responsive devices and/or coatings can release therapeutic agents at the time of tension or expansion.

In another embodiment, tension-responsive drug delivery devices can be a component of a cell scaffold or implantable material used in tissue expanders. Tissue expanders, as may be found in the breast, have step-wise increases in tension/strain/expansion. A tension-responsive drug delivery device incorporated into these scaffolds can therefore deliver increasing amounts of drug as time/tension/expansion increases over time.

As another embodiment, the tension-responsive drug delivery system can be implemented onto gastric bands that can reversibly expand with ingestion. The incorporated system can deliver increased drug, protein, or cytokines upon expansion, in tune with physiological responses.

In addition to the versatile loading ability, herein described, the tension responsive drug delivery system can also be integrated with, but not limited to, these medical devices for the treatment of a variety of diseases.

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not. As used herein, the term "comprising" or "comprises" includes "consisting essentially of" and "consisting of."

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The terms "lower" is used herein generally to mean a decrease by a statistically significant amount. However, for avoidance of doubt, "lower" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "higher" is used herein to generally mean an increase by a statically significant amount; for the avoidance of any doubt, "higher" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the term "nucleic acid" or "oligonucleotide" or grammatical equivalents herein means at least two nucleotides, including analogs or derivatives thereof, that are covalently linked together. Exemplary oligonucleotides include, but are not limited to, single-stranded and double-stranded siRNAs and other RNA interference reagents (RNAi agents or iRNA agents), shRNA (short hairpin RNAs), antisense oligonucleotides, aptamers, ribozymes, and microRNAs (miRNAs). The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10): 1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); and Nielsen, Nature, 365:566 (1993), content of all of which is herein incorporated by reference. The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl.

As used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)).

As used herein, the term "polymer" is intended to include both oligomeric and polymeric species, i.e., compounds which include two or more monomeric units, which may be a homopolymer or a copolymer. The term "homopolymer" is a polymer incorporating a single species of monomer units. The term "copolymer" is a polymer constructed from two or more chemically distinct species of monomer units in the same polymer chain. A "block copolymer" is a polymer which incorporates two or more segments of two or more distinct species of homopolymers or copolymers.

As used herein, the term "small molecule" can refer to compounds that are "natural product-like." However, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons. In some embodiments, "small molecule" as used herein refers to an organic compound that may serve a regulator or a biological process of the present invention and whose molecular weight limit is approximately 900 Dalton, allowing for the possibility to rapidly diffuse across cell membranes so that they can reach intracellular sites of action.

As used herein, the term "therapeutic agent" refers to any substance used internally or externally as a medicine for the treatment, cure, prevention, slowing down, or lessening of a disease or disorder, even if the treatment, cure, prevention, slowing down, or lessening of the disease or disorder is ultimately unsuccessful.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1

Figure 2:
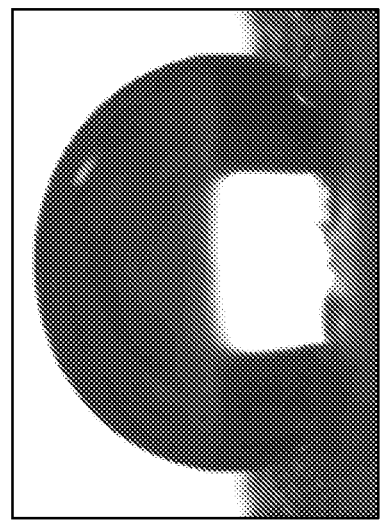
Figure 1:
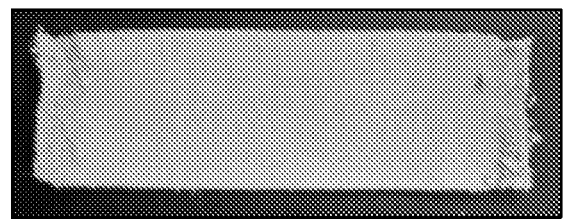

Electrospraying a Hydrophobic Coating on an Otherwise Hydrophilic, Absorbent Material Poly(ε-caprolactone) was dissolved in chloroform to make a 10% (w/v) solution. This solution was electrosprayed (flow rate of 3-5 mL/hr, a voltage of 10-25 kV, and distance of 10-15 cm) to create a layer or barrier comprised of discrete or interconnected polymer particles. The particles collected onto an absorbent hydroentangled cellulose/polyester mesh, which was attached to a grounded target through conductive copper tape. After one side had been treated, the meshes were gently removed from the copper tape, turned over, and placed back on the copper tape such that the untreated side could then be coated. The resulting surface of the hydroentangled cellulose/polyester mesh was altered from the deposition of particles, such that rather than absorbing a water drop on its surface, it became water-repellent, having a water contact angle greater than 90 degrees. (FIGS. 1 and 2)

Example 2

Figure 3:
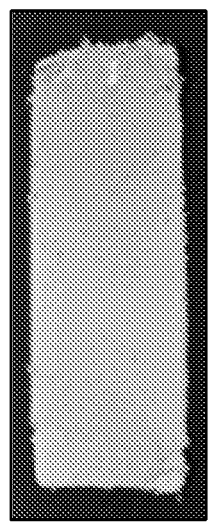
Figure 4:
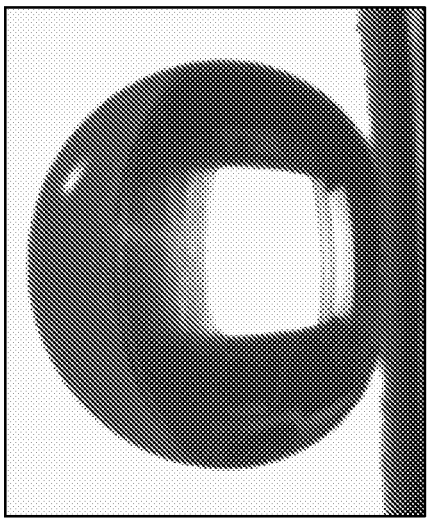

Electrospraying a Superhydrophobic Coating on an Otherwise Hydrophilic, Absorbent Material Poly(glycerol monostearatre-co-ε-caprolactone) and poly (ε-caprolactone) were dissolved in 1:1 ratio in chloroform to make a 10% (w/v) solution. This solution was electrosprayed (flow rate of 3-5 mL/hr, a voltage of 10-25 kV, and distance of 10-15 cm) to create a layer or barrier comprised of discrete or interconnected polymer particles. The particles collected onto an absorbent hydroentangled cellulose/polyester mesh, which was attached to a grounded target through conductive copper tape. After one side had been treated, the meshes were gently removed from the copper tape, turned over, and placed back on the copper tape such that the untreated side could then be coated. The resulting surface of the hydroentangled cellulose/polyester mesh was altered from the deposition of particles, such that rather than absorbing a water drop on its surface, it became extremely water-repellent, with water contact angles greater than or equal to 150 degrees. (FIGS. 3 and 4)

Example 3

Figure 5:
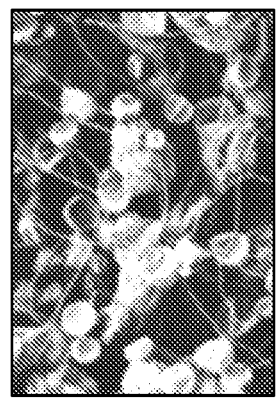

Electrospraying a Superhydrophobic Coating on an Otherwise Hydrophilic, Absorbent Material at Higher Polymer Concentrations Poly(glycerol monostearate-co-ε-caprolactone) and poly(ε-caprolactone) were dissolved in 1:1 ratio in chloroform to make a 20% (w/v) solution. This solution was electrosprayed (flow rate of 3-5 mL/hr, a voltage of 10-25 kV, and distance of 10-15 cm) to create a layer or barrier comprised of discrete or interconnected polymer particles. The particles collected onto an absorbent hydroentangled cellulose/polyester mesh, which was attached to a grounded target through conductive copper tape. After one side had been treated, the meshes were gently removed from the copper tape, turned over, and placed back on the copper tape such that the untreated side could then be coated. The resulting surface of the hydroentangled cellulose/polyester mesh was altered from the deposition of particles, such that rather than absorbing a water drop on its surface, it became water-repellent. (FIG. 5)

Example 4

Varying the Degree of Hydrophobicity by Choice of Polymer Proportions

Figure 6:
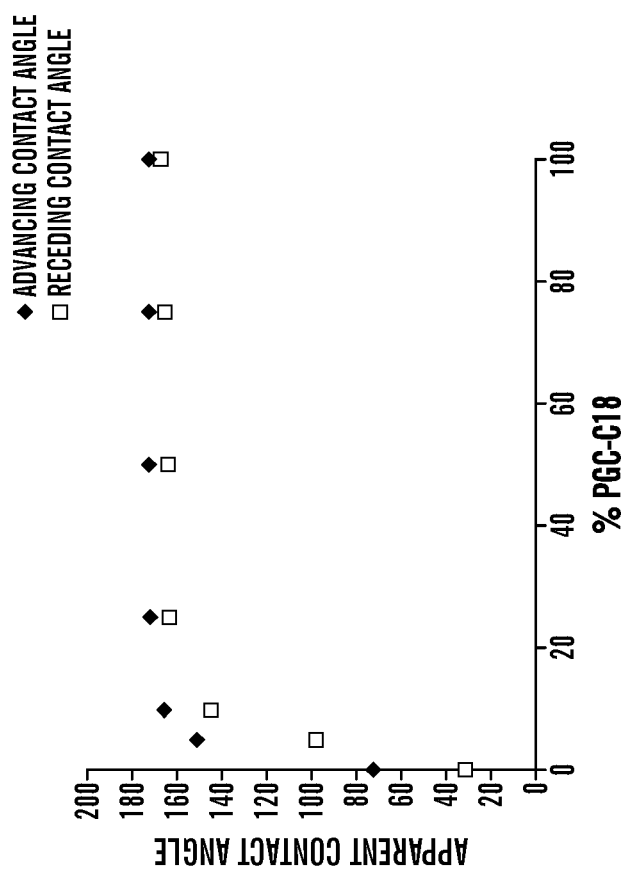
Figure 7A:
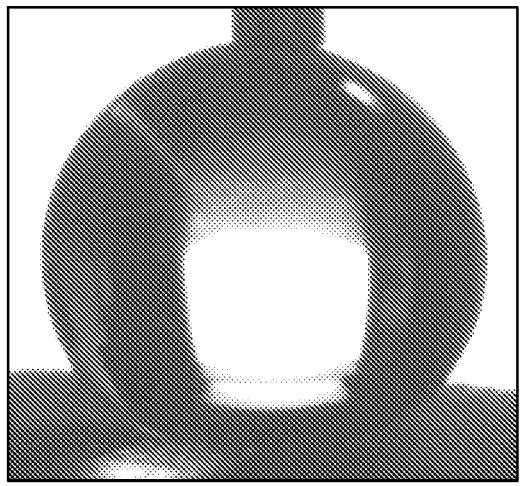
Figure 7B:
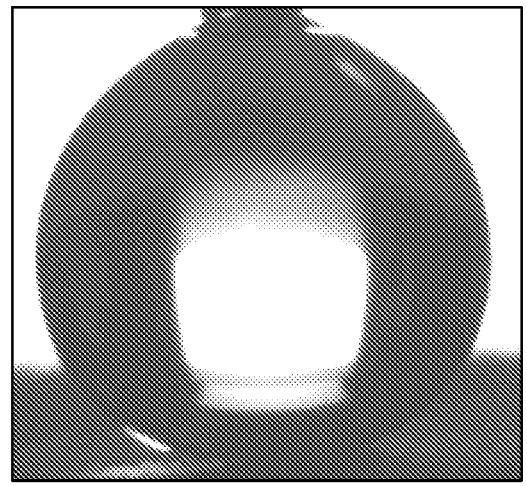

The degree of water-repellency was dependent on the relative proportions of poly(glycerol monostearate-co-ε-caprolactone) [hereafter known also as PGC-C18] and poly(ε-caprolactone) in the polymer solution, and was analyzed through water contact angle measurements, as elaborated in further examples below. Advancing contact angles varied from 70° to 170°, altering the surface from hydrophilic to hydrophobic and superhydrophobic states. With a 70/30 mixture (based on polymer mass) of PCL and PGC-C18, respectively, the contact angle was measured to be 146.6° and thus the surface was hydrophobic. With a 50/50 mixture of PCL and PGC-C18, the contact angle was measured to be 160° and thus the surface was superhydrophobic. (FIGS. 6 and 7)

Example 5

Varying the Degree of Hydrophobicity by Changing Particle Size

Figure 8:
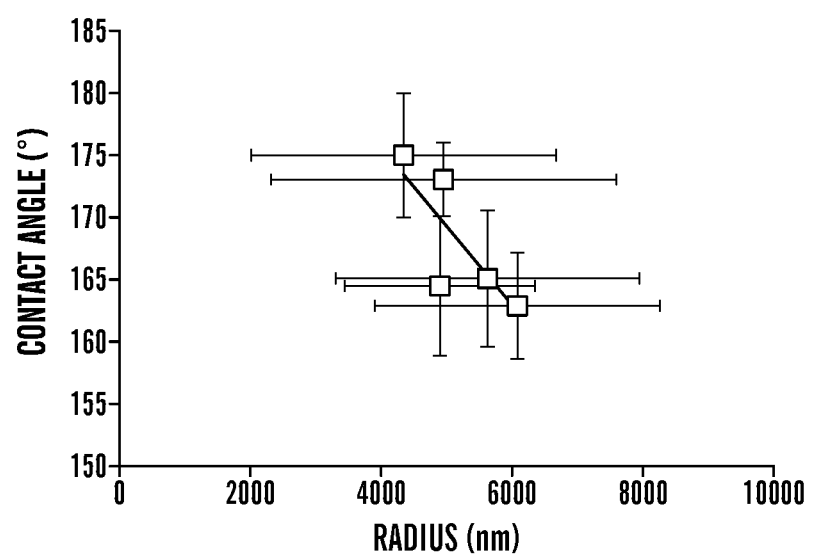
Figure 9:
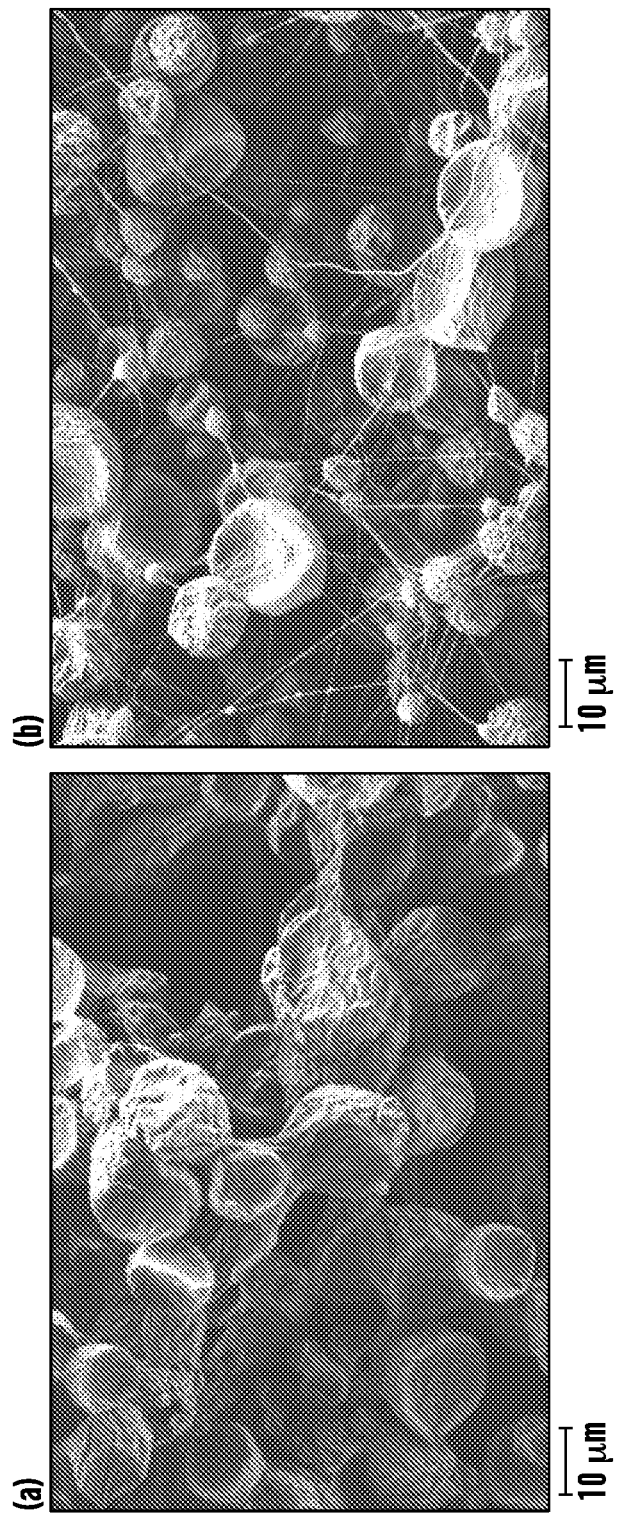

The degree of water-repellency was dependent on the size of the electrosprayed particles, and was analyzed through water contact angle measurements, as elaborated in further examples below. Particle size was determined using SEM, as described in Example 9 below. Contact angles varied from 162° to 174° as particle size decreased from 6000 to 4000 nm. (FIGS. 8 and 9)

Example 6

Varying the Degree of Hydrophobicity by Changing Particle Connectivity

Figure 10:
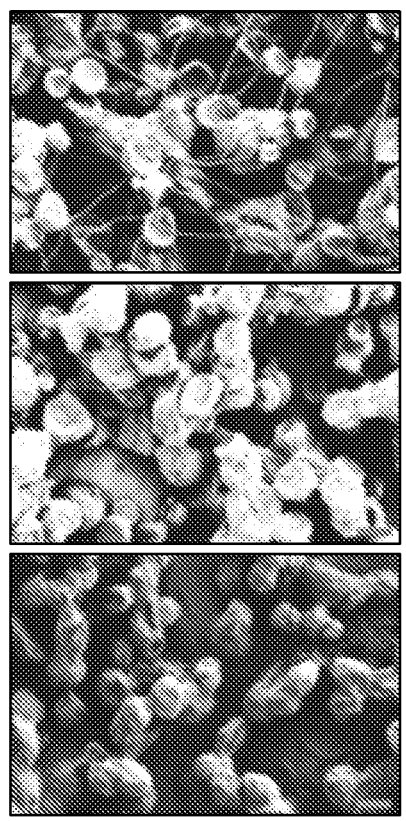

The degree of water-repellency was dependent on the relative dryness of the particles as they deposited on the surface of the material coated. Dryness of electrosprayed polymer particles was controlled by varying the total polymer concentration used for electrospraying, or by changing the tip-to-collector distance. Hydrophobicity was analyzed through water contact angle measurements, as elaborated in further examples below. Contact angles varied from 150° to 170°. (FIG. 10)

Example 7

Electrospinning a Hydrophobic or Superhydrophobic Coating on an Otherwise Hydrophilic, Absorbent Material Poly(glycerol monostearate-co-ε-caprolactone) and poly(ε-caprolactone) were dissolved in chloroform to make a 15% w/v solution. This solution was electrospun (flow rate of 10 mL/hr, a voltage of 10-20 kV, and distance of 10-15 cm) to create a layer or barrier comprised of an entangled polymer fiber or fibers. The fibers collected onto an absorbent hydroentangled cellulose/polyester mesh, which was attached to a grounded target through conductive copper tape. After one side had been treated, the meshes were gently removed from the copper tape, turned over, and placed back on the copper tape such that the untreated side could then be coated. The resulting surface of the cellulose/polyester mesh was altered from the deposition of particles, such that rather than absorbing water on its surface, it became water-repellent.

Example 8

Figure 11:
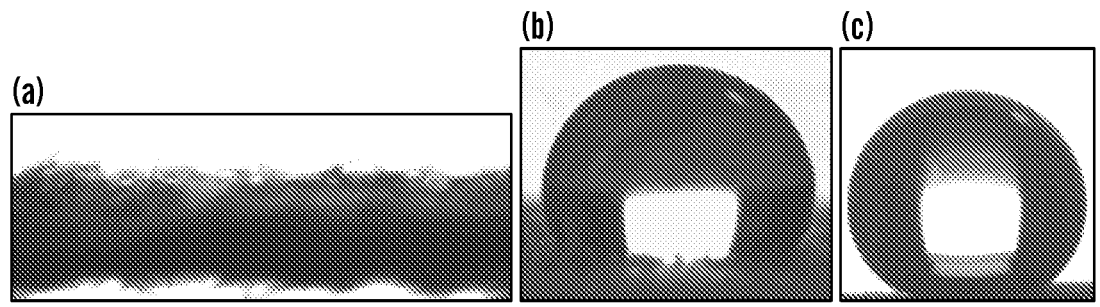

Characterizing the Surface of Electrosprayed Coatings Using Water Contact Angle Measurements The surface of the device, both before and after electrospraying, was characterized through contact angle measurements using a goniometer (Kruss DSA 100 Contact Angle Goniometer). A water droplet was added to the surface of the material, and the angle the droplet made with the surface was measured using a high-resolution, high-magnification camera and image analysis software, respectively. The water contact angles measured for a device fabricated in accordance with Examples 1-7, whereby the hydrophobicity could be varied from hydrophobic to superhydrophobic, ranged from 120° to 172°, respectively. A water droplet making an angle greater than 150° with the surface was generally considered superhydrophobic. (FIG. 11)

Example 9

Figure 13:
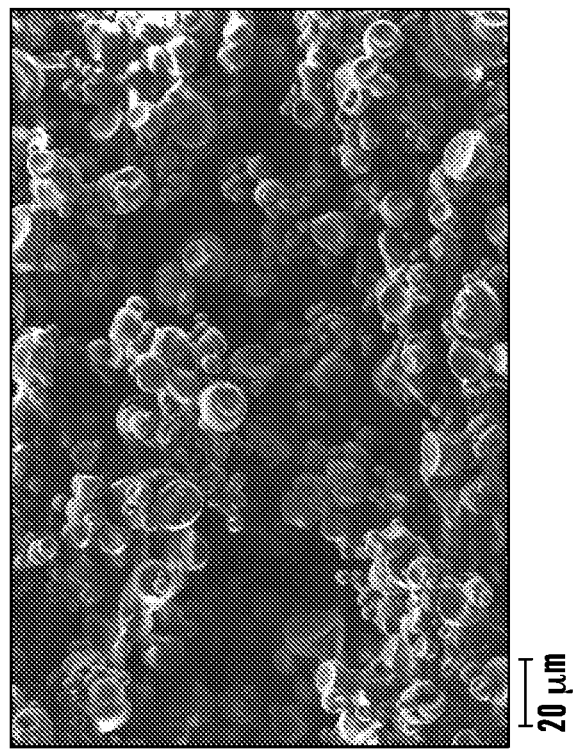
Figure 12:
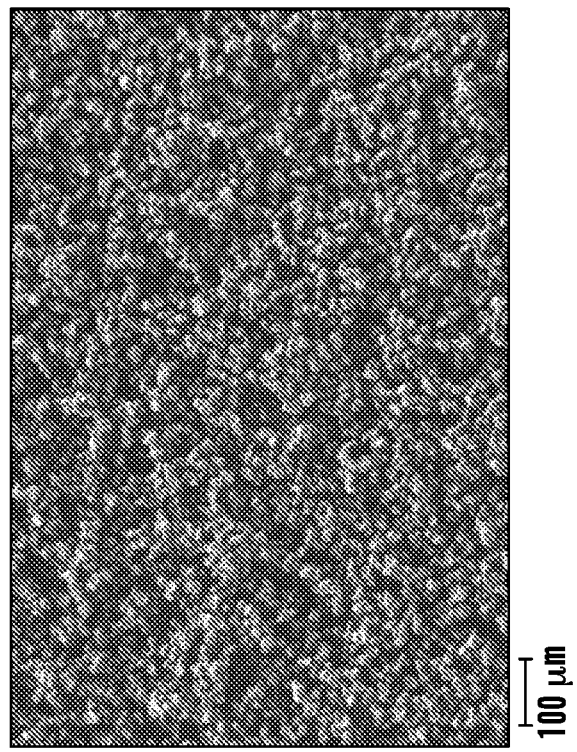
Figure 14:
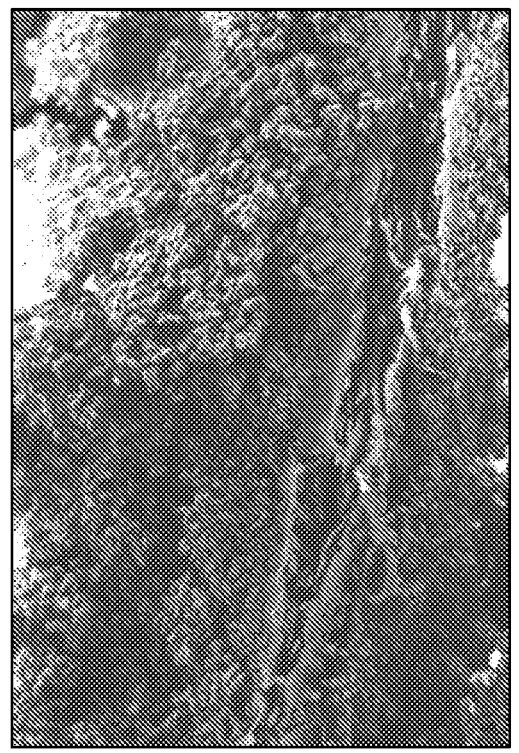

Characterizing the Surface of an Electrosprayed Mechanoresponsive Drug Delivery Device Using Electron Microscopy The surface of the device was imaged using scanning electron microscopy (SEM). The device was mounted, via adhesive conductive copper tape, onto an aluminum sample stub, and coated with a thin layer of gold-palladium via plasma deposition. The samples were then placed into the SEM and imaged at an accelerating voltage of 2 kV and a working distance of 6 cm. Magnification was varied: low magnifications were used to obtain a gross morphological characterization of the surface; higher magnifications were used to characterize the relative interconnectivity and/or size of the electrosprayed particles. SEM also was used to determine the thickness of the electrosprayed layers. This method was also used to image the cross-section of the drug delivery device. (FIGS. 12-14)

Example 10

Incorporating a Hydrophilic Dye into a Mechanoresponsive Drug Delivery Device

Figure 15:
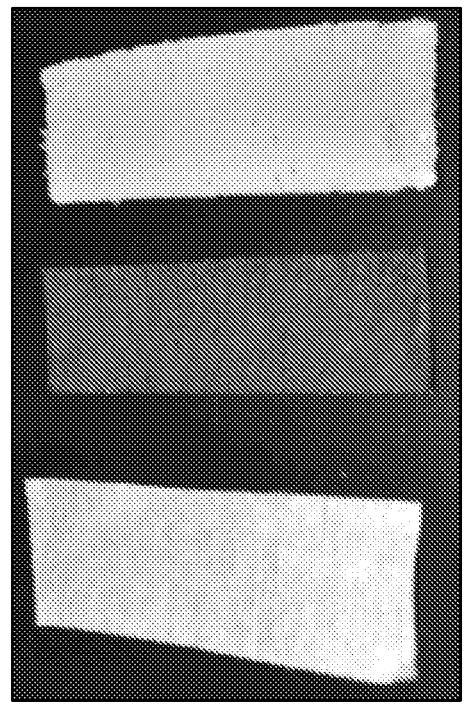

Fifty microliters of an aqueous solution of a hydrophilic green dye, serving as a model hydrophilic drug, was added on top of an absorbent hydroentangled cellulose and polyester mesh. The solution soaked into the mesh, turning the entirety of the mesh green. The mesh was allowed to dry at room temperature overnight to evaporate the solvent. The surface was then coated with a hydrophobic or superhydrophobic barrier comprised of polymer particles or fiber(s), as described in Examples 1-7 above, and subsequently characterized as described in Examples 8 and 9 above. (FIG. 15)

Example 11

Quantification of Dye Released from a Mechanoresponsive Drug Delivery Device

Figure 16:
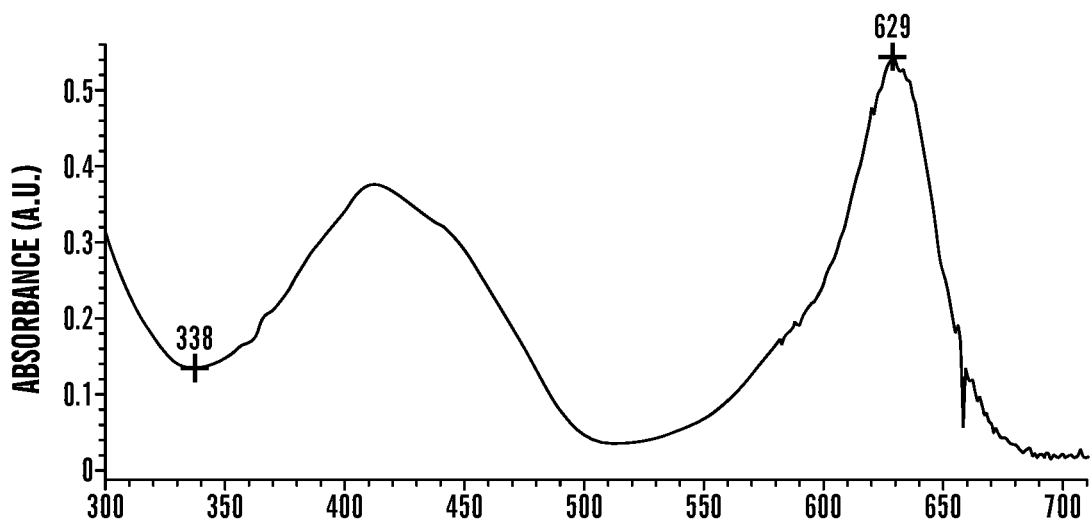
Figure 17:
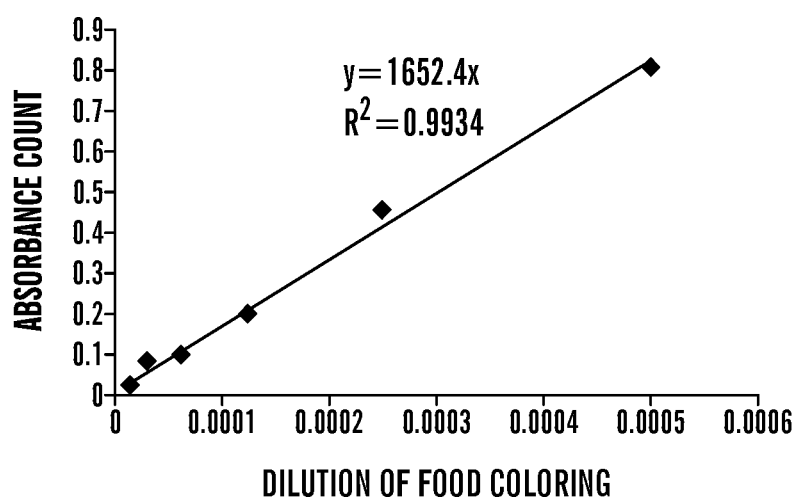

The amount of dye released from the drug delivery system into the surrounding aqueous environment was quantified through UV-visible spectrophotometry. The green colored dye had a local absorbance maximum at 630 nm. The absorbance value at this local maximum was used for determination of dye concentration in the release medium. A standard curve of absorbance versus dye concentration was first constructed, and unknown dye concentrations in the release medium were calculated from this standard curve. The concentration values were then converted to amount (mass) of dye released by multiplying by the total volume of solution into which the dye released. The amount of dye actually released was then divided by the amount of dye initially loaded into the device, to get a percentage of dye released as a function of time. (FIGS. 16 and 17)

Example 12

Incorporating a Protein into a Mechanoresponsive Drug Delivery Device

Figure 18:
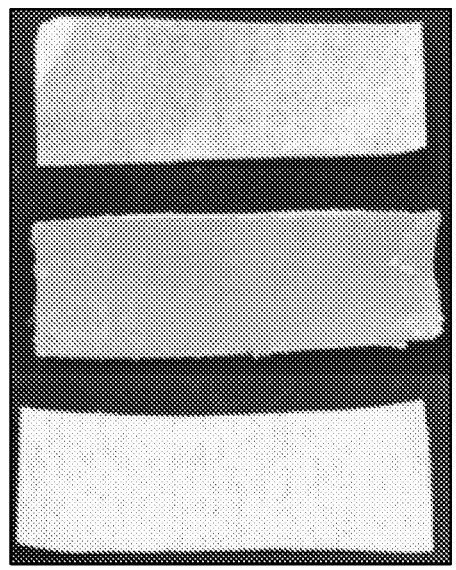

Fluorescein isothiocyanate-labeled bovine serum albumin (FITC-BSA) was dissolved in 10 mM Tris buffer at pH 7 to make a 10 mg/mL solution and dispensed onto the hydroentangled cellulose and polyester matrix core. After 24 hours of air-drying at room temperature to remove the solvent, the matrix contained incorporated protein, which had an orange color. The matrix was then coated on both sides by electrosprayed polymer particles or electrospun polymer fiber(s), in accordance with Examples 1-7. (FIG. 18)

Example 13

Figure 19:
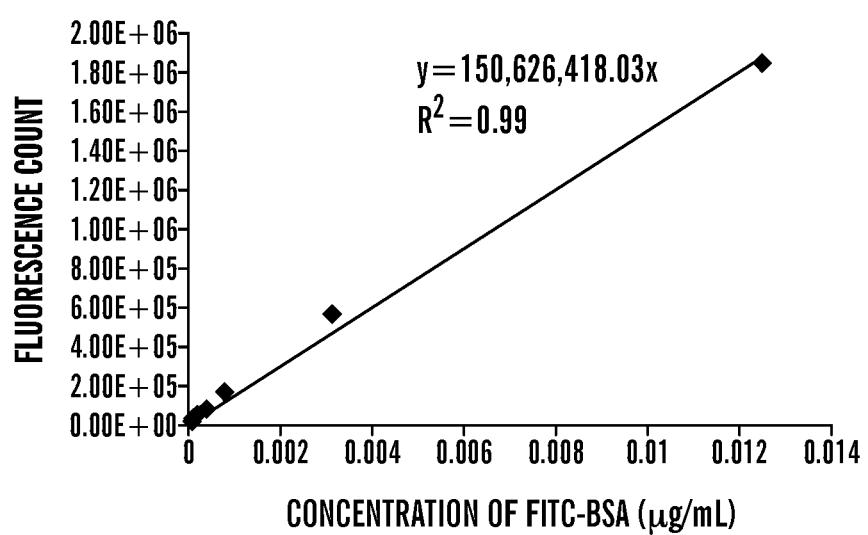
Figure 20:
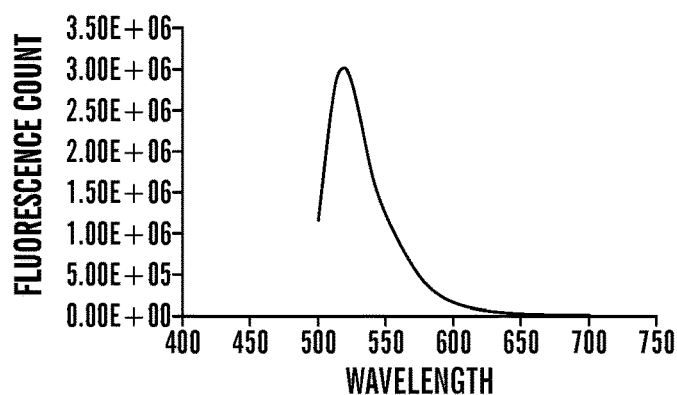
Figure 21:
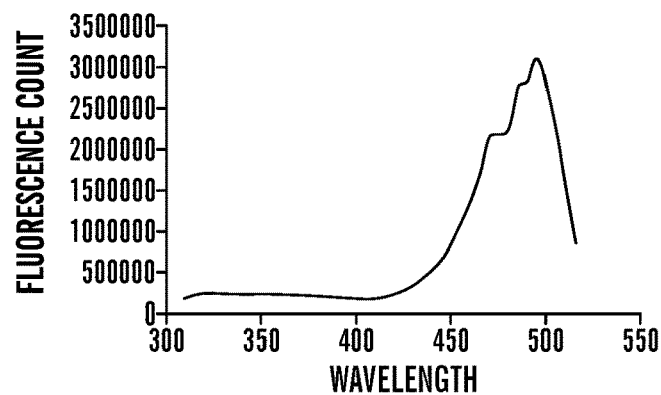

Quantification of a Fluorescently-Tagged Protein Released from a Mechanoresponsive Drug Delivery Device The amount of fluorescein isothiocyanate-labeled bovine serum albumin (FITC-BSA) released from the drug delivery system into the surrounding aqueous environment was quantified through fluorescence spectrophotometry. The fluorescein isothiocyanate is a fluorophore that is maximally excited around 495 nm and maximally emits at around 520 nm. The fluorescence intensity emitted at 520 nm was used to construct a standard curve of fluorescence versus FITC-BSA concentration. Unknown FITC-BSA concentrations in the release medium were calculated from this standard curve. The concentration values were then converted to amount (mass) of FITC-BSA released by multiplying by the concentration values by the total volume of solution into which the protein released. The amount of FITC-BSA actually released was then divided by the amount of FITC-BSA initially loaded into the device, to get a percentage of protein released as a function of time. (FIGS. 19-21)

Example 14

Incorporation of a Chemotherapy Agent (Cisplatin) into a Mechanoresponsive Drug Delivery Device Cis-diamminedichloroplatinum(II) (cisplatin) was dissolved in N,N-dimethylformamide (DMF) at 25 mg/mL, and 50 µL of this solution was dispensed on top of an absorbent hydroentangled cellulose and polyester mesh, and soaked into the mesh. The mesh was allowed to air-dry at room temperature overnight to evaporate the solvent, leaving behind the chemotherapy agent. The surface was then coated with a hydrophobic or superhydrophobic barrier comprised of polymer particles or fiber(s), as described in Examples 1-7 above, and subsequently characterized as described in Examples 8 and 9 above.

Example 15

Figure 22:
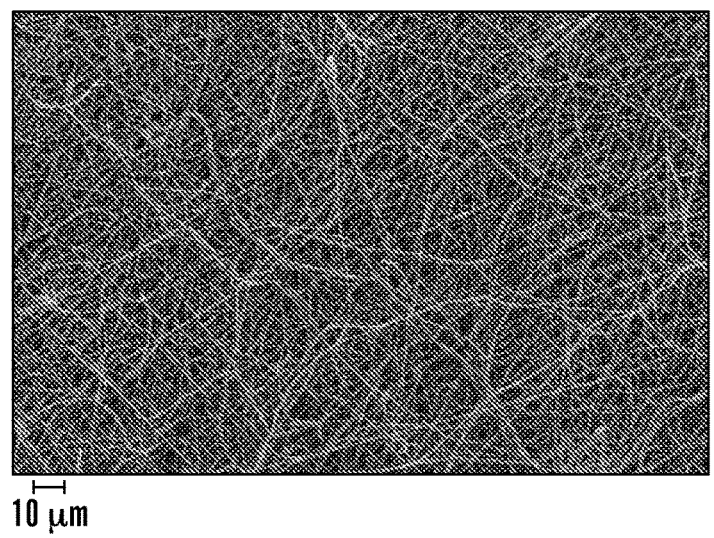

Incorporation of a Chemotherapy Agent (Cisplatin) into an Electrospun Mechanoresponsive Drug Delivery Device Dichloromethane (1.5 mL) was added to a vial containing 1.170 g polycaprolactone and 0.130 g poly(glycerol succinate-co-ε-caprolactone). Then, 2.5 mL of DMF was added to the vial and the contents were vigorously mixed. Cisplatin (38 mg) was then dissolved in 2.5 mL of N,N-dimethylformamide (DMF), and this solution was added to the polymer solution and vigorously mixed. The solution was transferred to a syringe and electrospun at 3.5 mL/hr, 16 cm tip-to-collector distance, and 13 kV to form an entangled nanofiber mesh that rapidly absorbs water when a droplet is placed on the surface. The surface of this mesh was then coated with a hydrophobic or superhydrophobic barrier comprised of polymer particles or fiber(s), as described in Examples 1-7 above, and subsequently characterized as described in Examples 8 and 9 above. (FIG. 22)

Example 16

Quantification of a Chemotherapy Agent (Cisplatin) Released from a Mechanoresponsive Drug Delivery Device The amount of cisplatin released from the drug delivery system into the surrounding aqueous environment was quantified through flameless atomic absorption spectroscopy (also known as graphite furnace atomic absorption or electrothermal absorption (Varian AA240Z Atomic Absorption)). The platinum atom has a strong absorbance band at 265.9 nm, and was used for detecting the presence of platinum (the major component of the anticancer agent cisplatin) in the release medium. A standard curve was first created, and aliquots (sampled at different timepoints) from the release medium with unknown cisplatin concentrations were determined from this standard curve. The concentration values were then converted to amount (mass) of cisplatin released by multiplying the concentration by the total volume of solution into which the agent released. The amount of cisplatin actually released was then divided by the amount of cisplatin initially loaded into the device, to get a percentage of cisplatin released as a function of time.

Example 17

Figure 23:
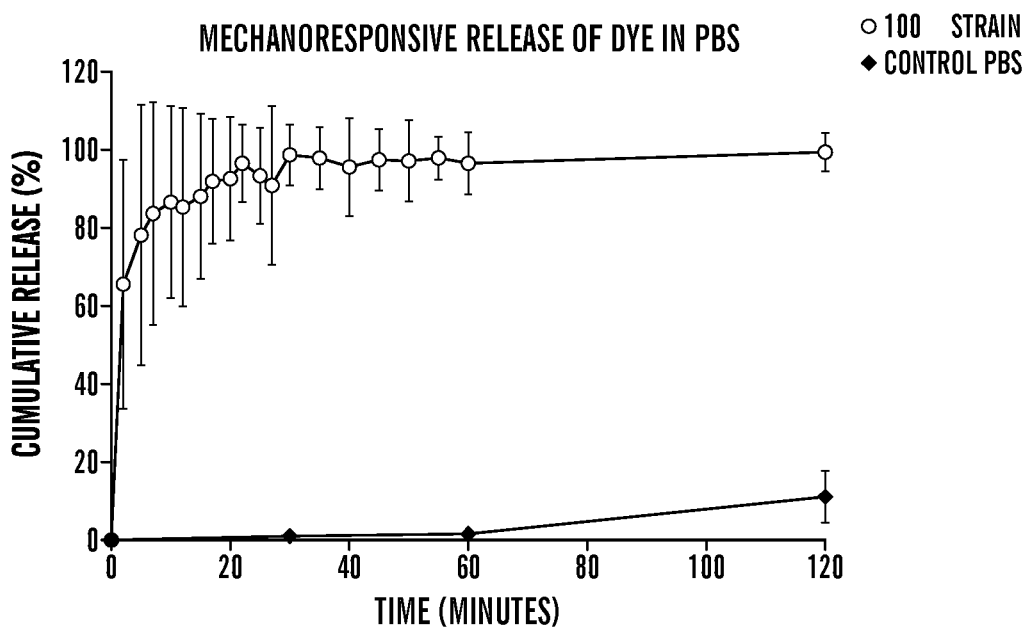

Demonstration of a Mechanoresponsive Drug Delivery Device Using a Hydrophilic Dye A dye-incorporated drug delivery device was fabricated in accordance with Example 1 above. The ends of the material were placed between two pieces of foam tape and further secured by applying glue to the ends in contact with the foam tape. The ends were then placed between the grips of a tensile tester machine (Instron 5848 Microtester) and the sample length between the grips was recorded. A water bath was placed under the sample arms, and the drug delivery device was submerged beneath 300 mL of phosphate-buffered saline (PBS). A magnetic stir bar was also added to the bath to ensure thorough mixing during the study. The Instron software was then programmed to extend the sample arms at a constant rate of 2 mm/s until a travel distance equivalent to the initial sample length was reached (corresponding to 100% strain). Once the device was stretched, aliquots of release medium were sampled at predetermined time points. The percentage of dye released into the surrounding aqueous environment was calculated from UV-Vis spectrophotometry, as described in Example 11. Devices were also placed on the tensile tester, but in this instance they were not stretch (0% strain), to serve as control experiments. Release of the dye from devices subjected to strain was rapid, and was achieved only under the application of strain. Devices not subjected to strain (i.e., controls) did not release appreciable amounts of dye. (FIG. 23)

Example 18

Demonstration of a Mechanoresponsive Drug Delivery Device Using a Protein

Figure 24:
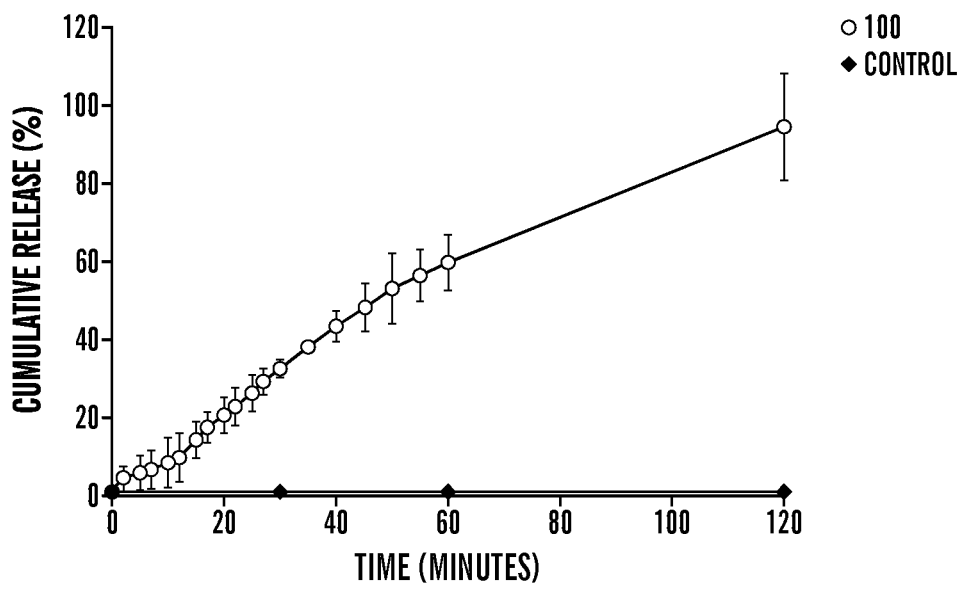

A drug delivery device with incorporated fluorescein isothiocyanate-labeled bovine serum albumin (FITC-BSA) was fabricated in accordance with Example 1 above. The ends of the material were placed between two pieces of foam tape and further secured by applying glue to the ends in contact with the foam tape. The ends were then placed between the grips of a tensile tester machine (Instron 5848 Microtester) and the sample length between the grips was recorded. A water bath was placed under the sample arms, and the drug delivery device was submerged beneath 300 mL of phosphate-buffered saline (PBS) with 10% serum (fetal bovine serum). A magnetic stir bar was also added to the bath to ensure thorough mixing during the study. The Instron software was then programmed to extend the sample arms at a constant rate of 2 mm/s until a travel distance equivalent to the initial sample length was reached (corresponding to 100% strain). Once the device was stretched, aliquots of release medium were sampled at predetermined time points. The percentage of protein released into the surrounding aqueous environment was calculated using fluorescence spectrophotometry, as described in Example 13 above. Devices were also placed on the tensile tester, but in this instance they were not stretched (0% strain), to serve as control experiments. Release of the fluorescent protein from devices subjected to strain was rapid, and was achieved only under the application of strain. Devices not subjected to strain (i.e., controls) did not release appreciable amounts of protein. (FIG. 24)

Example 19

Figure 25:
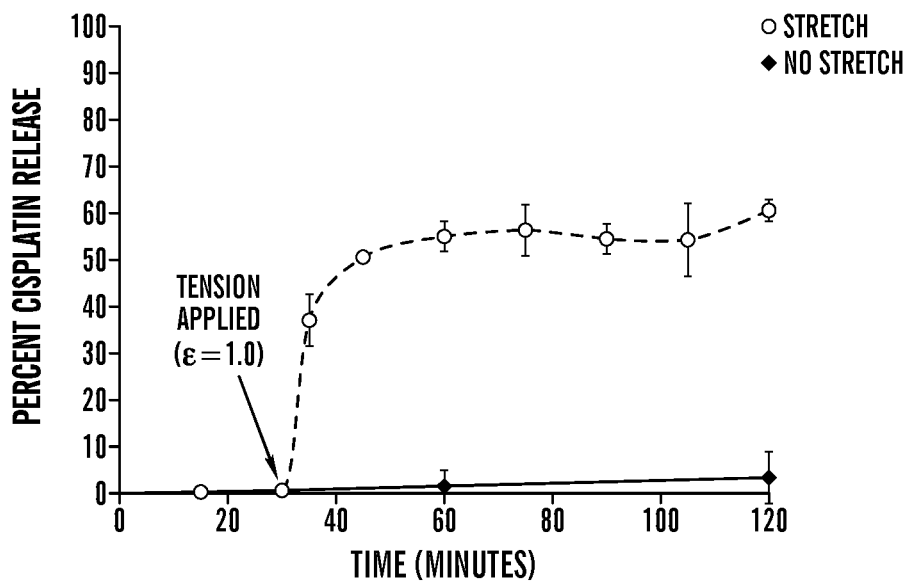

Demonstration of a Mechanoresponsive Drug Delivery Device Using a Chemotherapy Agent A drug delivery device with incorporated cisplatin was fabricated in accordance with Example 1 above. The ends of the material were placed between two pieces of foam tape and further secured by applying glue to the ends in contact with the foam tape. The ends were then placed between the grips of a tensile tester machine (Instron 5848 Microtester) and the sample length between the grips was recorded. A water bath was placed under the sample arms, and the drug delivery device was submerged beneath 300 mL of phosphate-buffered saline (PBS). A magnetic stir bar was also added to the bath to ensure thorough mixing during the study. The Instron software was then programmed to extend the sample arms at a constant rate of 2 mm/s until a travel distance equivalent to the initial sample length was reached (corresponding to 100% strain). Once the device was stretched, aliquots of release medium were sampled at predetermined time points. The percentage of cisplatin released into the surrounding aqueous environment was calculated using flameless atomic absorption spectroscopy, as described in Example 16. Devices were also placed on the tensile tester, but in this instance they were not stretched (0% strain), to serve as control experiments. Release of the chemotherapy agent from devices subjected to strain was rapid, and was achieved only under the application of strain. Devices not subjected to strain (i.e., controls) did not release appreciable amounts of drug. (FIG. 25)

Example 20

Figure 26:
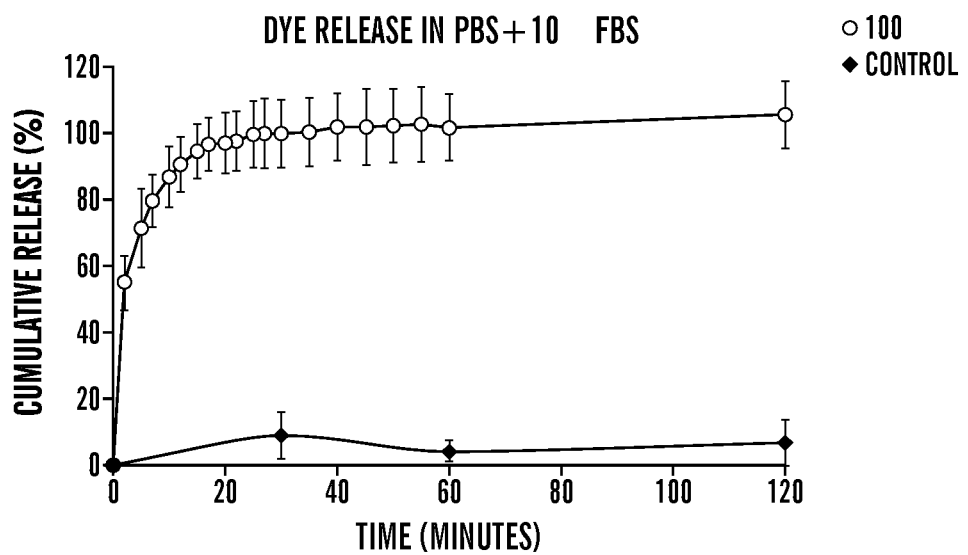

Demonstration of a Mechanoresponsive Drug Delivery Device into a Protein-Rich Aqueous Environment Embodiments of Examples 17 and 18 were extended to include a study on the release behavior of the dye and protein from mechanoresponsive delivery devices in the presence of 10% fetal bovine serum (FBS) in phosphate buffered saline (PBS), to mimic the biological milieu. Similar release behavior to that shown in Examples 17 and 18 was observed, whereby the unstretched (control) devices did not release appreciable amounts of drug. On the other hand, samples stretched to 100% strain experienced rapid drug release. (FIG. 26)

Example 21

Figure 27:
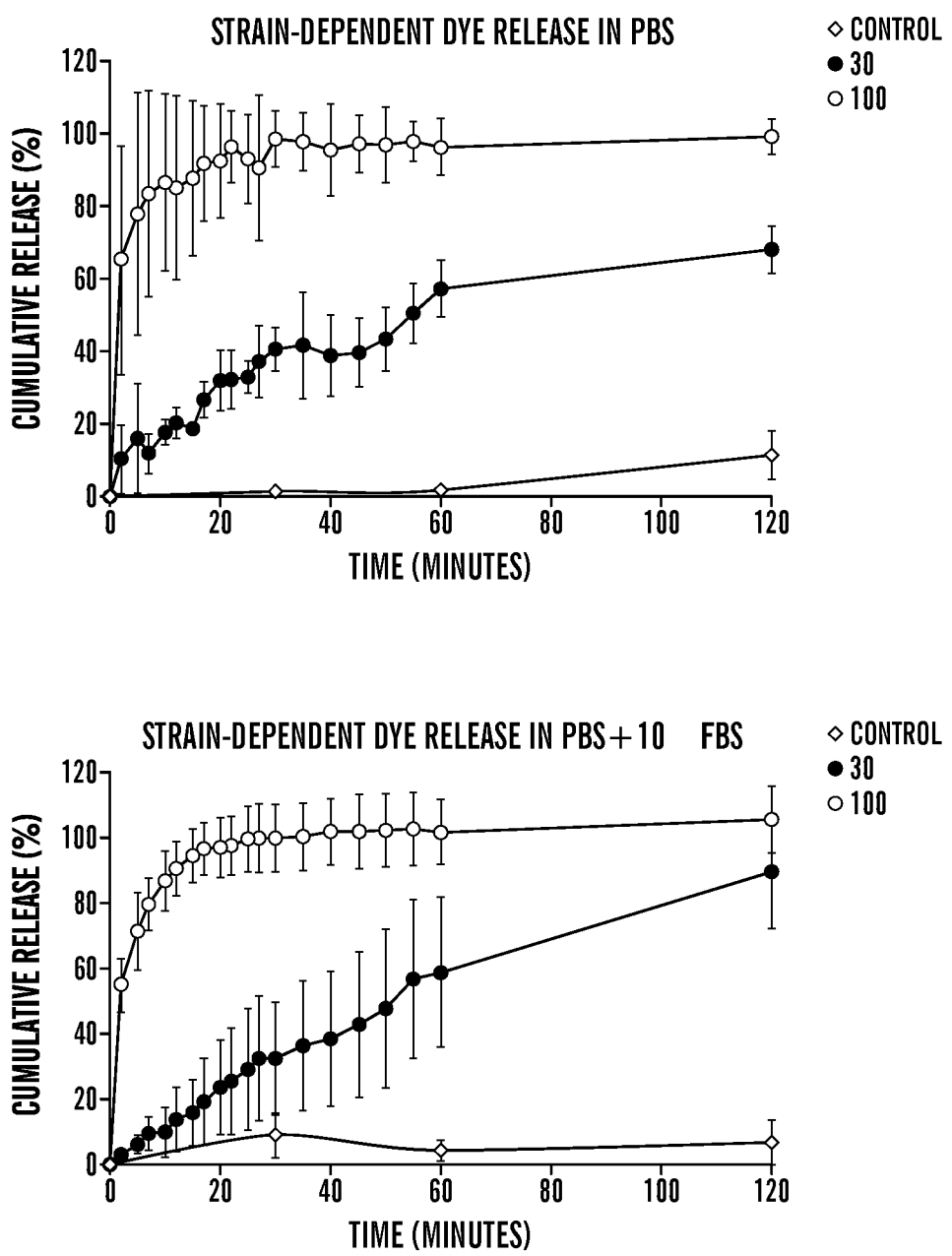

Modulating Release of Hydrophilic Dye by Varying the Magnitude of Applied Strain A dye-incorporated drug delivery device was fabricated in accordance with Examples 1 and 10 above. The coating was electrosprayed using a tip-to-collector distance of 10 cm. The ends of the material were placed between two pieces of foam tape and further secured by applying glue to the ends in contact with the foam tape. The ends were then placed between the grips of a tensile tester machine (Instron 5848 Microtester) and the sample length between the grips was recorded. A water bath was placed under the sample arms, and the drug delivery device was submerged beneath 300 mL of phosphate-buffered saline (PBS), or 300 mL PBS containing 10% fetal bovine serum (FBS). A magnetic stir bar was also added to the bath to ensure thorough mixing during the study. The Instron software was then programmed to extend the sample arms at a constant rate of 2 mm/s until a travel distance equivalent to thirty percent of the initial sample length was reached (corresponding to 30% strain), or equivalent to the entire initial sample length was reached (corresponding to 100% strain). Once the device was stretched, aliquots of release medium were sampled at predetermined time points. The percentage of dye released into the surrounding aqueous environment was calculated from UV-Vis spectrophotometry, as described in Example 11. Devices were also placed on the tensile tester, but in this instance they were not stretched (0% strain) to serve as a control experiment. Release of the dye was most rapid from devices subjected to 100% strain and more moderate from devices subjected to 30% strain. Devices not subjected to strain did not release appreciable amounts of dye. (FIG. 27)

Example 22

Scanning Electron Microscopy of Different Electrosprayed Coating Morphologies

Figure 28:
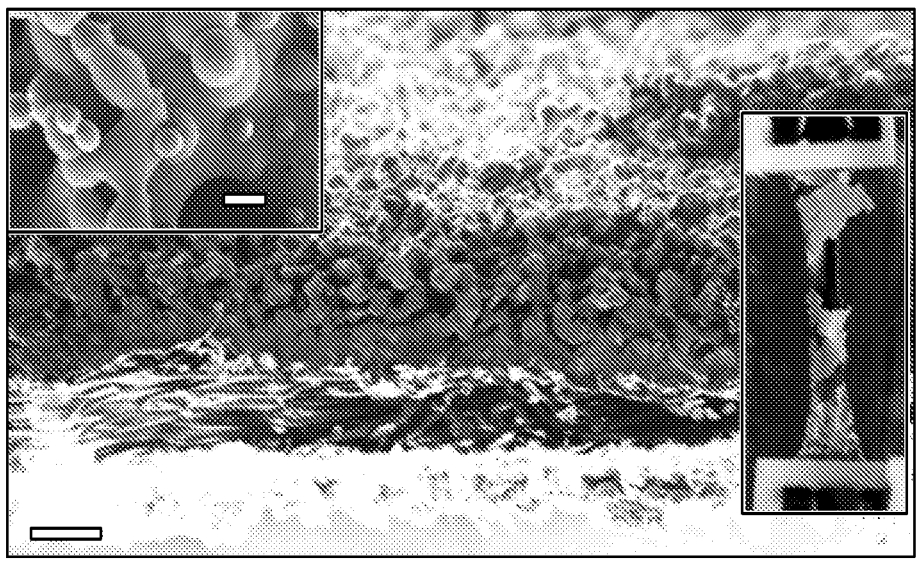
Figure 29:
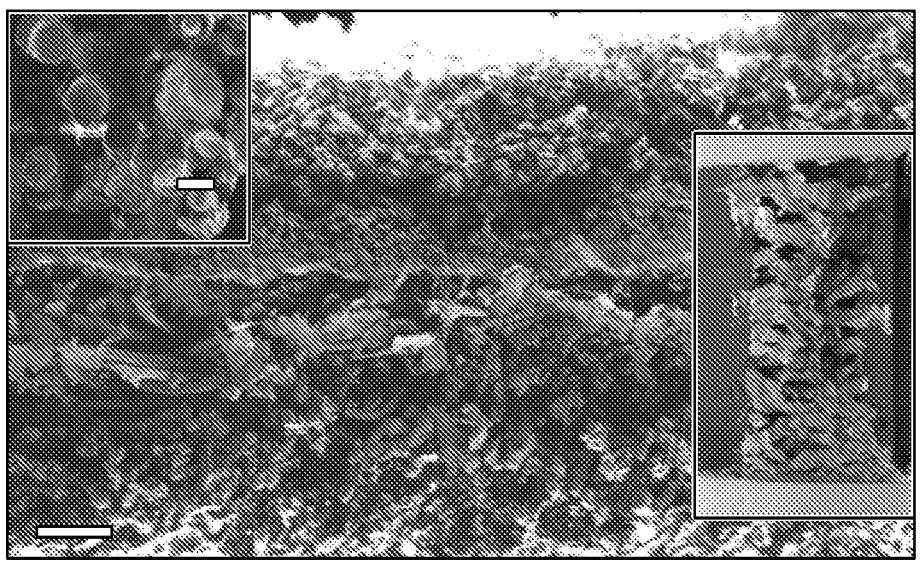

Electrosprayed coatings were fabricated as described above in Example 17. The tip-to-collector distance was held at 10 cm at first. From FIG. 28, scanning electron microscopy was used to image the connectivity of the electrosprayed polymer particles. The morphology is described as "wet" since the particles meld into each other. Another set of dye-loaded core meshes were coated with an increased tip-to-collector distance of 15 cm. From FIG. 29, scanning electron microscopy of the coating shows the polymer particles are less connected and described as "dry". These changes in morphology have implications in how the cracks are formed and thus influences the release profile of the adsorbed substrate.

Example 23

Figure 30:
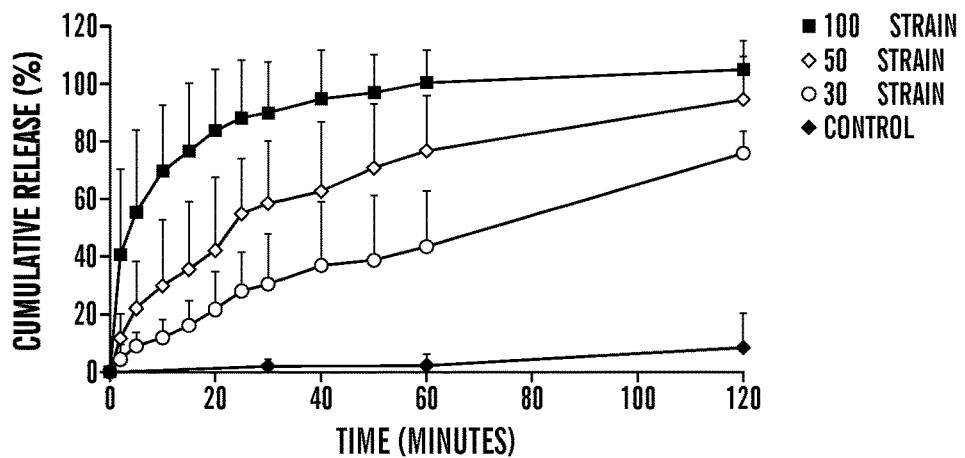

Modulating Release of Hydrophilic Dye by Varying the Magnitude of Applied Strain with Dry Superhydrophobic Electrosprayed Coating A dye-incorporated drug delivery device was fabricated in accordance with Examples 1 and 10 above. The coating was electrosprayed using a tip-to-collector distance of 15 cm. The ends of the material were placed between two pieces of foam tape and further secured by applying glue to the ends in contact with the foam tape. The ends were then placed between the grips of a tensile tester machine (Instron 5848 Microtester) and the sample length between the grips was recorded. A water bath was placed under the sample arms, and the drug delivery device was submerged beneath 300 mL PBS containing 10% fetal bovine serum (FBS). A magnetic stir bar was also added to the bath to ensure thorough mixing during the study. The Instron software was then programmed to extend the sample arms at a constant rate of 2 mm/s until a travel distance equivalent to thirty percent of the initial sample length was reached (corresponding to 30% strain), equivalent to half of the initial sample length was reached (corresponding to 50% strain), or equivalent to the entire initial sample length was reached (corresponding to 100% strain). Once the device was stretched, aliquots of release medium were sampled at predetermined time points. The percentage of dye released into the surrounding aqueous environment was calculated from UV-Vis spectrophotometry, as described in Example 11. Devices were also placed on the tensile tester, but in this instance they were not stretched (0% strain) to serve as a control experiment. Release of the dye was most rapid from devices subjected to 100% strain and more moderate from devices subjected to 50% and 30% strain. Devices not subjected to strain did not release appreciable amounts of dye (FIG. 30).

Example 24

Figure 31:
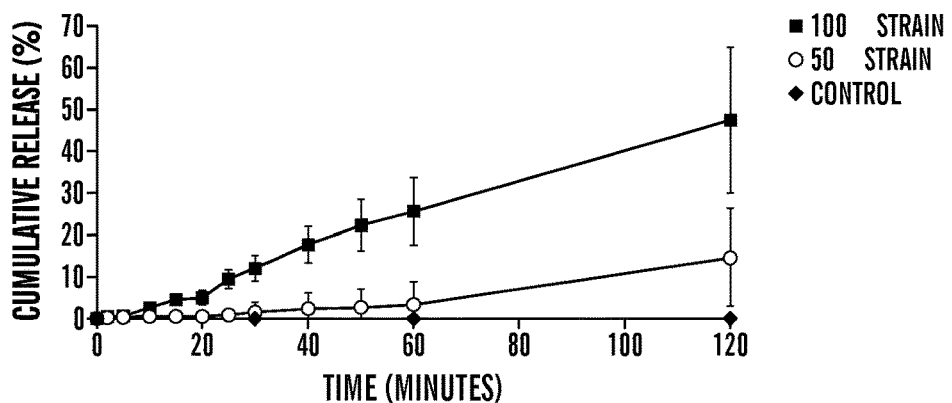

Demonstration of a Strain-Dependent Mechanoresponsive Drug Delivery Device Using a Protein with Dry Superhydrophobic Electrosprayed Coating A drug delivery device with incorporated fluorescein isothiocyanate-labeled bovine serum albumin (FITC-BSA) was fabricated in accordance with Example 1 above. The coating was electrosprayed using a tip-to-collector distance of 15 cm. The ends of the material were placed between two pieces of foam tape and further secured by applying glue to the ends in contact with the foam tape. The ends were then placed between the grips of a tensile tester machine (Instron 5848 Microtester) and the sample length between the grips was recorded. A water bath was placed under the sample arms, and the drug delivery device was submerged beneath 300 mL of phosphate-buffered saline (PBS) with 10% serum (fetal bovine serum). A magnetic stir bar was also added to the bath to ensure thorough mixing during the study. The Instron software was then programmed to extend the sample arms at a constant rate of 2 mm/s until a travel distance equivalent to half of the initial sample length was reached (corresponding to 50% strain), or equivalent to the entire initial sample length was reached (corresponding to 100% strain). Once the device was stretched, aliquots of release medium were sampled at predetermined time points. The percentage of protein released into the surrounding aqueous environment was calculated using fluorescence spectrophotometry, as described in Example 13 above. Devices were also placed on the tensile tester, but in this instance they were not stretched (0% strain) to serve as a control experiment. Release of the fluorescent protein was most rapid from devices subjected to 100% strain and more moderate from devices subjected to 50% strain. Devices not subjected to strain did not release appreciable amounts of protein (FIG. 31).

Example 25

Electrospraying Various Coating Thicknesses

Figure 32:
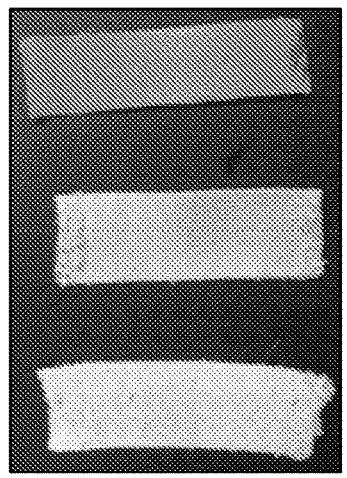
FIG. 32 is a picture showing electrosprayed coatings of various thicknesses (top to bottom): 0.67 mm, 0.87 mm, and 1.05 mm.

Dye-loaded core material was electrosprayed as described in Example 10. The thicknesses were measured with a micrometer (Mitutoyo IP 65). The core material has a thickness of 0.25 mm, and we have demonstrated the ability to spray various thicknesses in FIG. 32: 0.67 mm, 0.87 mm, and 1.05 mm (from top to bottom). The coatings are all electrosprayed in the same manner; thicknesses is controlled by increasing deposition time. Additionally, the release profiles of the dye-loaded drug delivery systems can be quantified in a similar way as demonstrated in Examples 17-24. (FIG. 32)

Example 26

Analysis of Strain-Dependent Release with Crack Propagation

Figure 33:
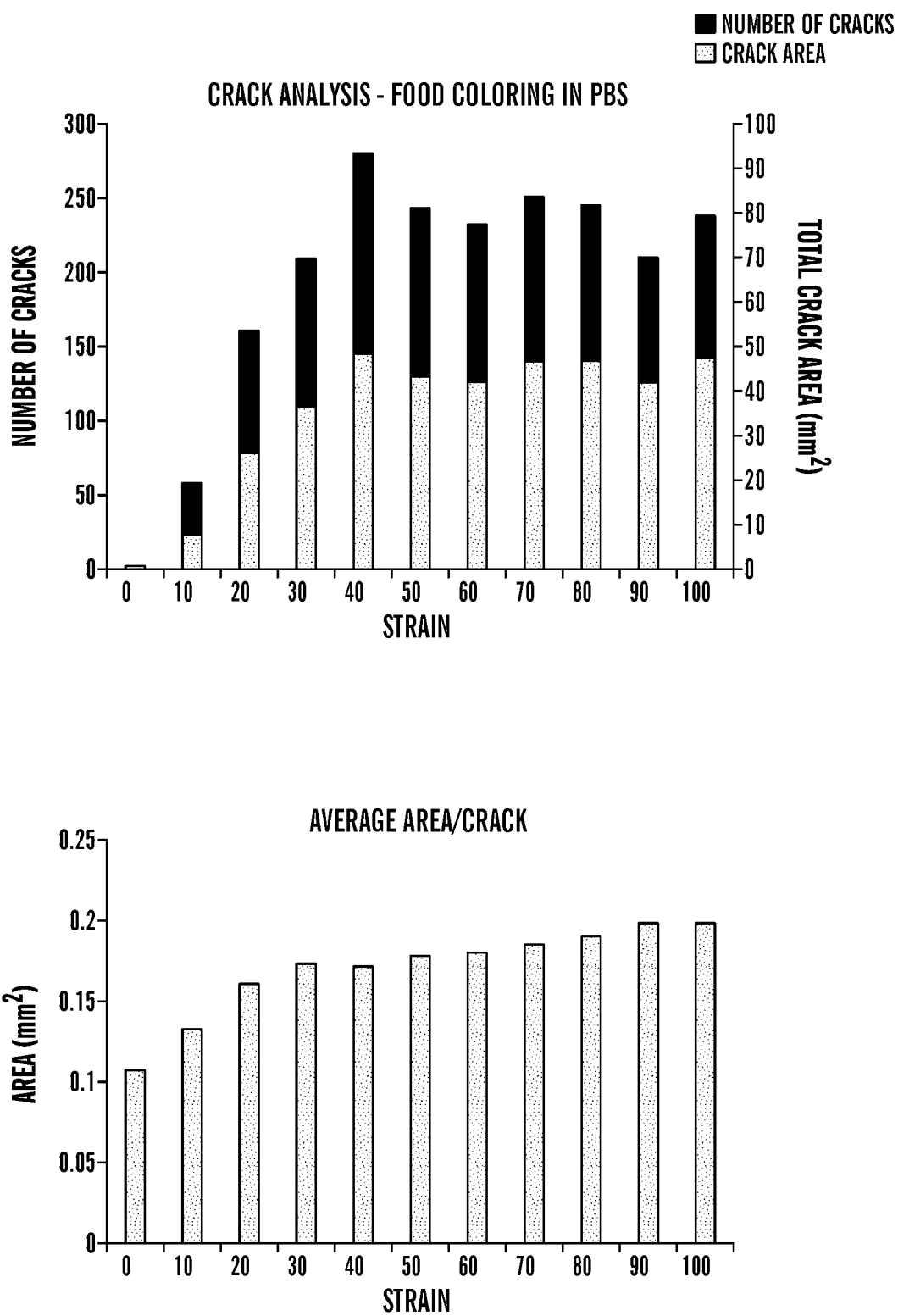
FIG. 33 are bar graphs showing analysis of crack propagation of a dye-loaded mesh with electrosprayed PGC-C18 and PCL coating with increasing strain from 0% to 100%. The coating was electrosprayed using a tip-to-collector distance of 15 cm.
Figure 34:
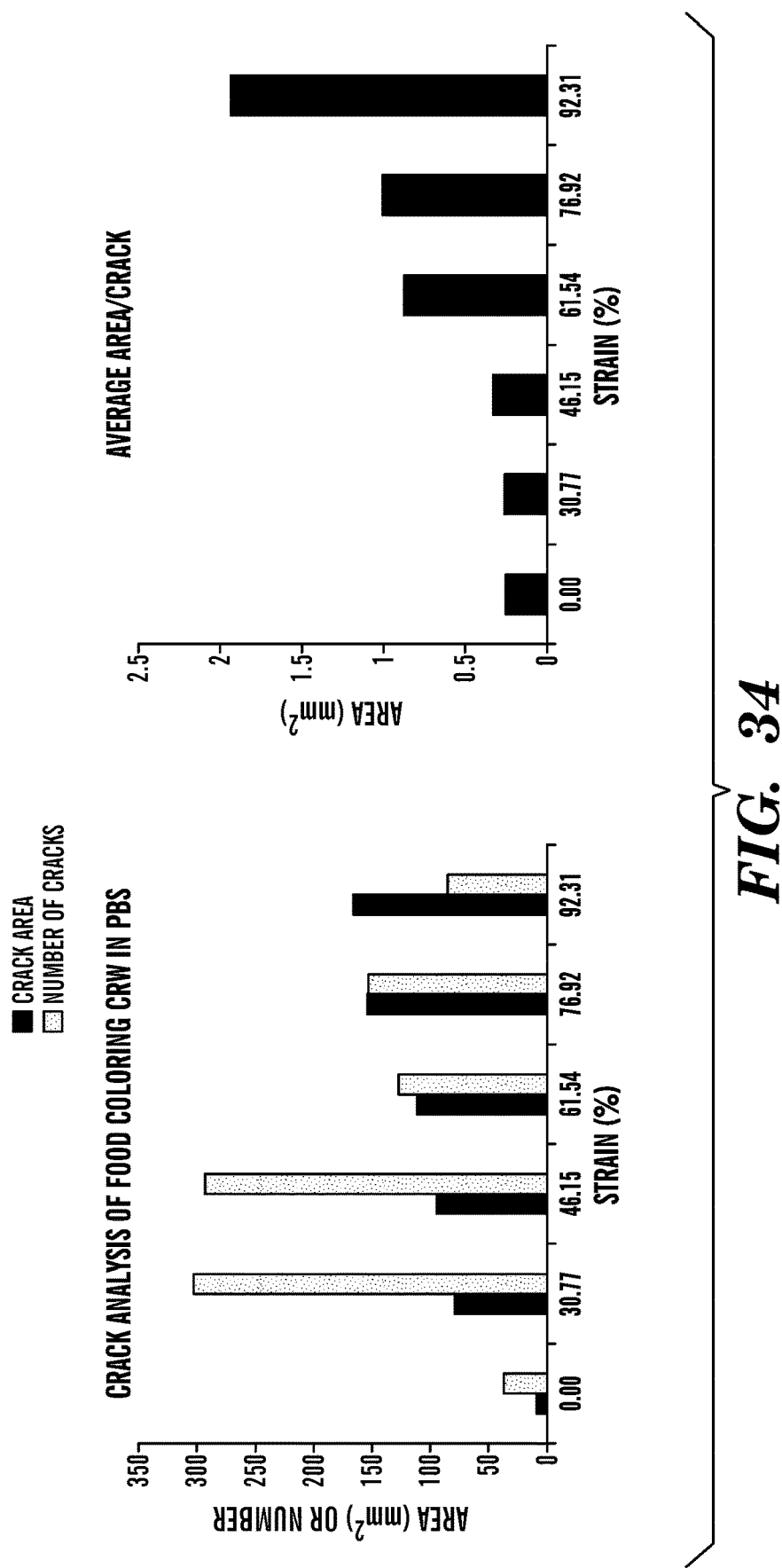
FIG. 34 are bar graphs showing analysis of crack propagation of a dye-loaded mesh with electrosprayed PGC-C18 and PCL coating with increasing strain from 0% to 100%. The coating was electrosprayed using a tip-to-collector distance of 10 cm.

Video analysis was performed on dye-loaded electrosprayed meshes as the tensile strain increased from 0% to 100% in phosphate-buffered saline (PBS). Still images from the video were processed using ImageJ software. The dark contrast from the dye in the matrix allowed color thresholding to determine crack area and crack number. The average area per crack was also calculated by dividing the crack area by the number of cracks at specific strains. FIGS. 33-34 depict the crack/fracture analysis of the superhydrophobic coatings and show that increasing strain causes more cracks form, and also that mature cracks begin to increase in area; all and any of which can contribute to altering the drug release rate by changing the fracture severity.

Example 27

Therapeutic Response of Cancer Cells to Cisplatin-Releasing Meshes

Figure 35:
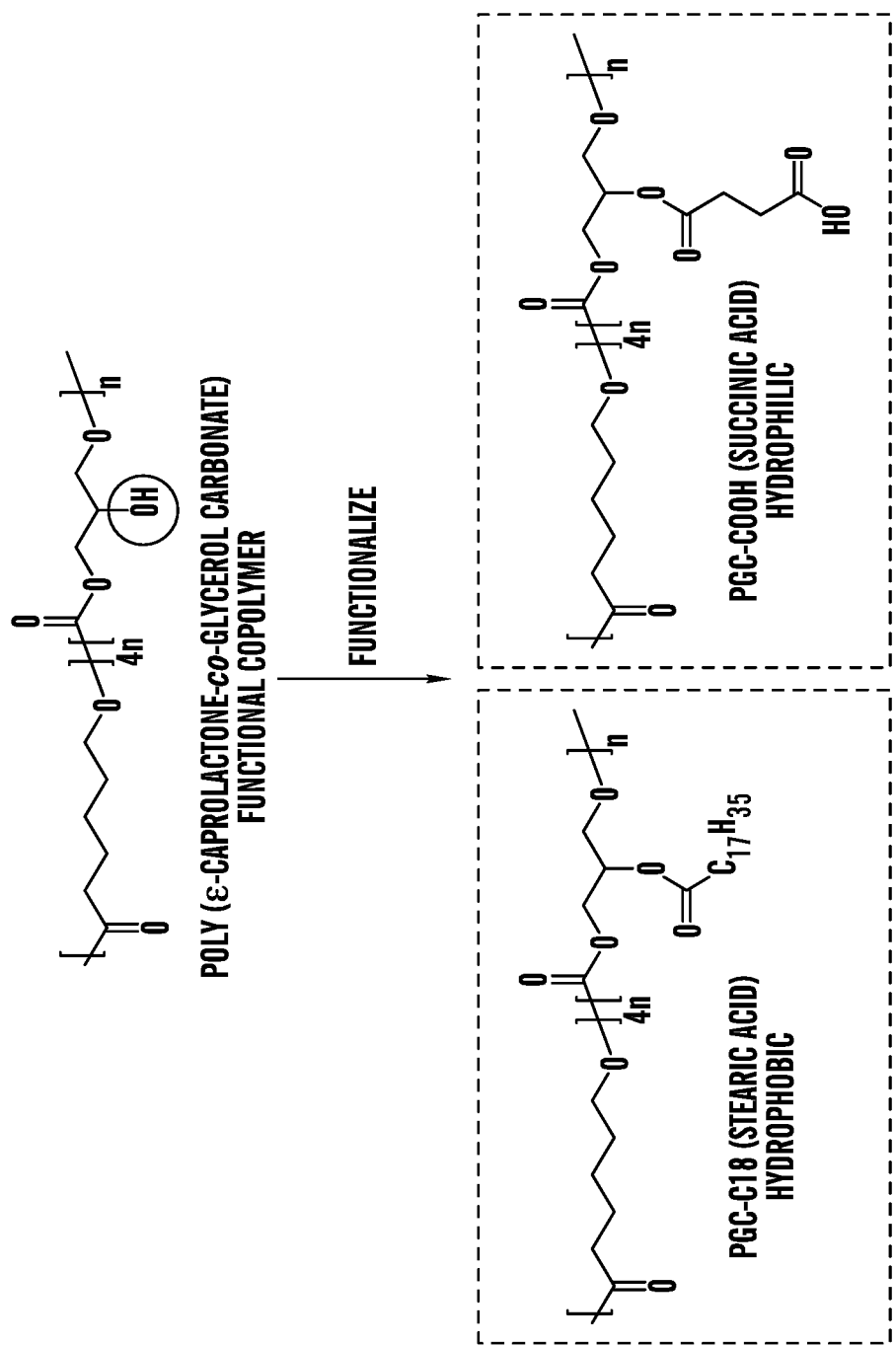
FIG. 35 is a schematic diagram showing a superhydrophobic dopant copolymer (left) and a hydrophilic dopant copolymer (right) used in this example.

An electrospun mesh fabricated in accordance with Example 15, where the copolymer dopant was varied to alter the wettability of the material. In one embodiment, the mesh was fabricated using 70% polycaprolactone and 30% poly(glycerol monostearate-co-caprolactone) ("superhydrophobic mesh"); in another embodiment, the mesh was fabricated using 90% polycaprolactone and 10% poly(glycerol-2-succinate-co caprolactone) ("hydrophilic mesh"); in another embodiment, the mesh was fabricated from pure polycaprolactone ("moderately hydrophobic mesh") (FIG. 35).

Figure 36:
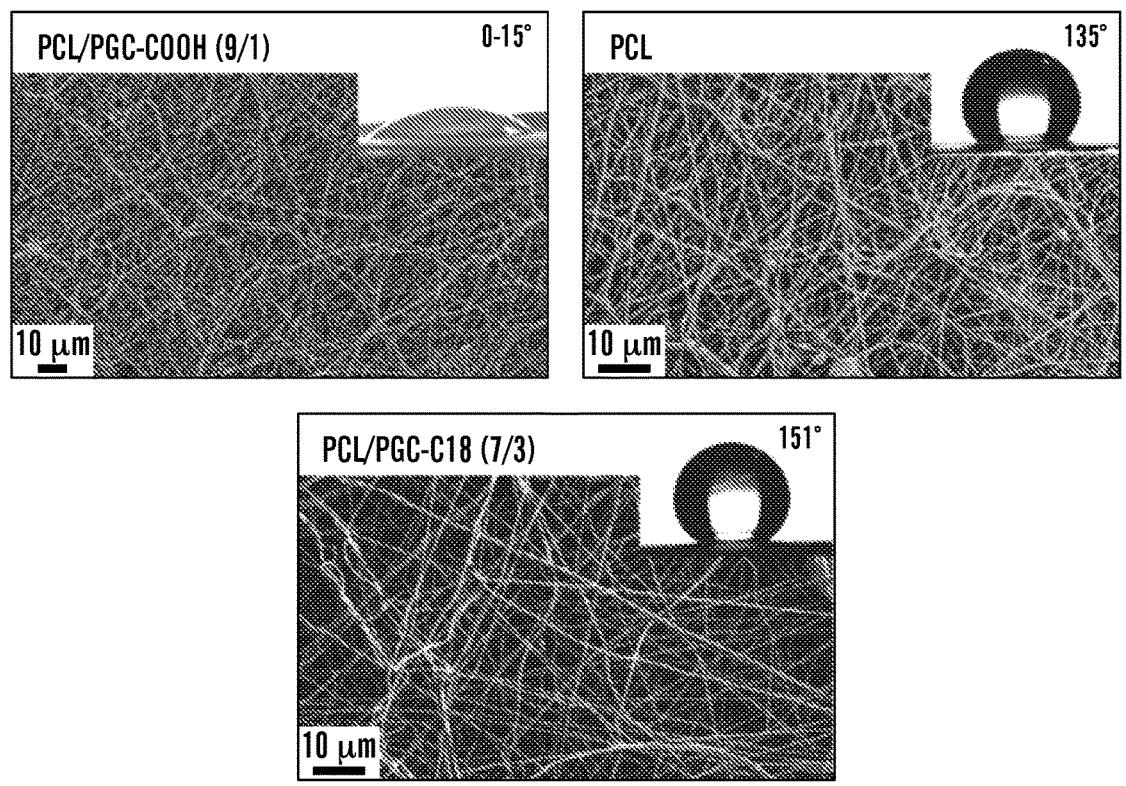
FIG. 36 are scanning electron micrographs and wettability measurements of electrospun meshes containing cisplatin. Top left is a hydrophilic mesh, top right is a hydrophobic mesh, bottom center is a superhydrophobic mesh.
Figure 37:
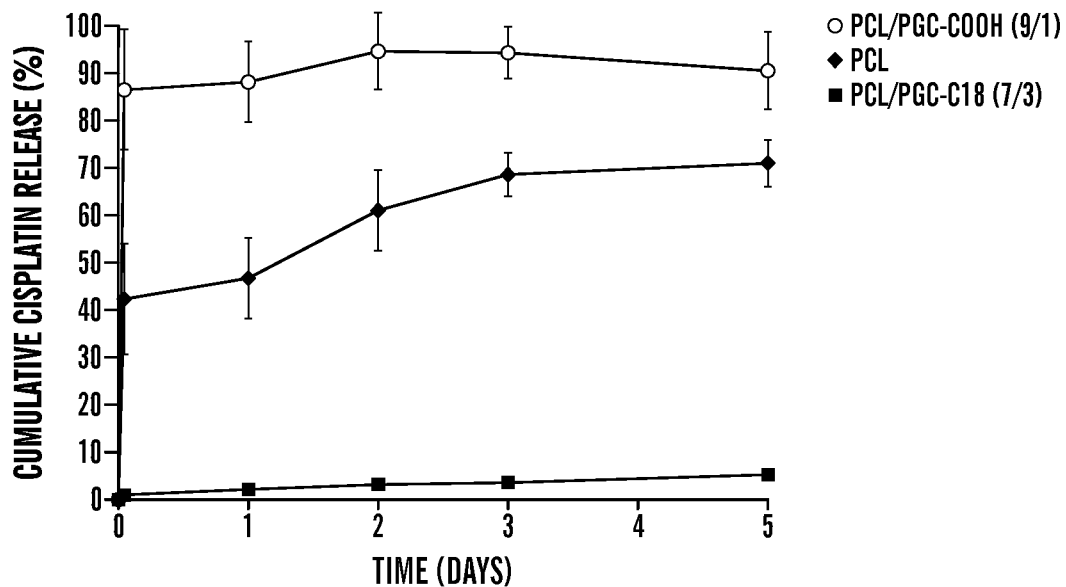
FIG. 37 shows percent release of cisplatin from electrospun meshes as a function of immersion time.

The resulting contact angles demonstrated the difference in wettability (FIG. 36), with the superhydrophobic having a contact angle of >150 degrees, the moderately hydrophobic mesh having a contact angle of 135 degrees. The hydrophilic mesh absorbed water and thus had a water contact angle of zero degrees. The percent release of cisplatin from these meshes as a function of immersion time in phosphate-buffered saline is shown in FIG. 37.

Figure 38:
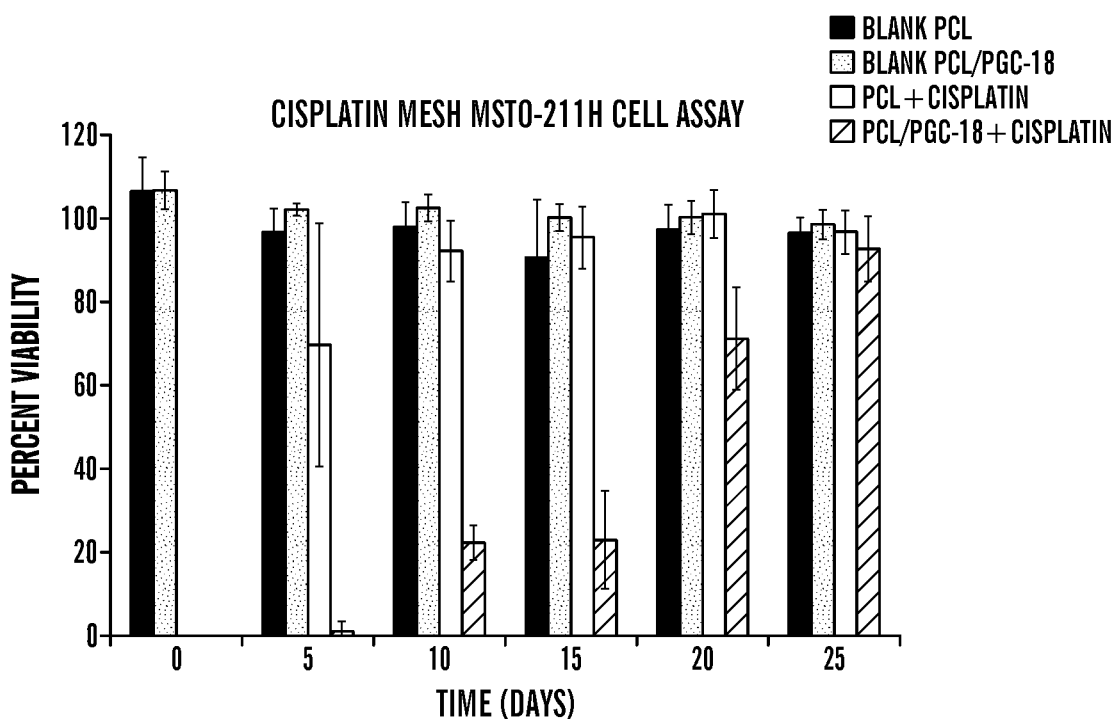
FIG. 38 shows percent viability of cancer cells (MSTO-211H) as a function of immersion time for PCL and superhydrophobic electrospun meshes without cisplatin (black and grey, respectively) and containing cisplatin (black stripes and grey stripes, respectively).

The difference in wettability between a moderately hydrophobic cisplatin-loaded electrospun mesh and a hydrophilic mesh is substantially different, yet their release rates of cisplatin are essentially similar. The superhydrophobic mesh, however, greatly delayed cisplatin release. The therapeutic efficacy of the moderately hydrophobic mesh and the superhydrophobic mesh was also tested using MSTO 211H mesothelioma cells in vitro (FIG. 38). The superhydrophobic mesh had prolonged cancer cell-killing capabilities compared to the moderately hydrophobic mesh. Therefore, superhydrophobic materials may be used to greatly delay the release of cisplatin due to the extreme resistance to wettability.

Example 28

Delivery of Cisplatin to OE33 Cancer Cells

Cisplatin is used in the treatment of esophageal cancer. The inventors demonstrate delivery of a therapeutic amount of cisplatin to effectively kill cancer cells in vitro. They used an esophageal cell line, OE33 (Sigma), to show the efficacy of cisplatin released from the tension-modulated drug delivery device, and that a dose-response curve can be generated using force and/or strain as the means to alter the dose. The $IC_{50}$ of cisplatin with OE33 is 2.17+/−0.33 µM for 72 hours of incubation (Minegaki et al, Oncology Letters 2013 5(2)). By altering the amount of force, the rate of cisplatin release can be controlled in order to provide a range of concentrations at fixed time points. The concentration of cisplatin can be either lower or higher than the IC50 value such that a similar curve may be created using force and/or strain on the x-axis, rather than, or in addition to, concentration. Hence, we anticipate the number of dead cells to coincide with (a) the amount of strain applied, and (b) the time allowed for release.

Cisplatin can be loaded into these systems as described in Example 14. Cisplatin can be used to achieve dose-dependent tumor cell death, and also strain-dependent cell death. A strain-dependent release of cisplatin, a small hydrophilic drug molecule, can be seen in FIG. 39. Because cisplatin is a cytotoxic chemotherapeutic drug, the amount of cisplatin released correlates with cell viability (FIG. 40). The inventors were able to deliver an efficacious amount of cisplatin to change the cell viability, as determined by MTS Assay.

Example 29

Step-Wise Release of Dye

Dye-loaded hydroentangled cellulose/polyester meshes were electrosprayed with poly(glycerol monostearate-co-ε-caprolactone) and poly(ε-caprolactone) in a 50:50 ratio, dissolved in 10% (w/v) chloroform as described in Example 2. The electrosprayed mesh was subjected to increasing strains, similar to the description in Example 17. Dye release in phosphate buffered saline with fetal bovine serum (10%) was quantified as described in Example 11. The dye release rate was determined at increasing strains and shown to be significantly different (p<0.05). (FIG. 41)

Example 30

Incorporation of Hydrophobic Drug into Mechanoresponsive Drug Delivery Device

SN-38, the active metabolite of irinotecan, was dissolved in 1:1 chloroform:methanol with DMF (dimethylformamide) to make a 1 mg/mL solution and dispensed onto the hydroentangled cellulose and polyester matrix core. After 24 hours of air-drying at room temperature to remove the solvents, the matrix containing incorporated hydrophobic drug was then coated on both sides by electrosprayed polymer particles or electrospun polymer fiber(s), in accordance with Examples 1-7.

Example 31

Quantification of Hydrophobic Drug Release from Mechanoresponsive Drug Delivery Device SN-38 from release media was quantified by mixing one (1) part release medium (containing drug) in three (3) parts 20 mM borate buffer (pH=9), which converts SN-38 to the carboxylate form. Fluorescence was detected by fluorimetry at an excitation of 380 nm and emission of 550 nm, as previously described (Yohe, J Controlled Release 2012, 162). (FIG. 42)

Example 32

Modulating Release of Hydrophobic Chemotherapeutic Agent by Varying the Amount of Applied Strain A drug delivery device with incorporated SN-38 was fabricated in accordance with Example 2, above. The ends of the material were placed between two pieces of foam tape and further secured by applying glue to the ends in contact with the foam tape. The ends were then placed between the grips of a tensile tester machine (Instron 5848 Microtester) and the sample length between the grips was recorded. A water bath was placed under the sample arms, and the drug delivery device was submerged beneath 300 mL of phosphate-buffered saline (PBS) or cell media, RPMI with 10% v/v fetal bovine serum. A magnetic stir bar was also added to the bath to ensure thorough mixing during the study. The Instron software was then programmed to extend the sample arms at a constant rate of 2 mm/s until a travel distance equivalent to thirty percent of the initial sample length was reached (corresponding to 30% strain), or equivalent to the entire initial sample length was reached (corresponding to 100% strain). Once the device was stretched, aliquots of release medium were sampled at predetermined time points. The percentage of SN-38 released into the surrounding aqueous environment was calculated using fluorimetry, as described in Example 31. Devices were also placed on the tensile tester, but in this instance they were not stretched (0% strain), to serve as control experiments. Release of the chemotherapy agent from devices subjected to 100% strain and more moderate from devices subjected to 30% strain. Devices not subjected to strain (i.e., controls) did not release appreciable amounts of drug. (FIG. 43)

Example 33

Delivery of SN-38 to OE33 Cancer Cells

By altering the amount of strain, the rate of SN-38 release can be controlled in order to provide a range of concentrations at fixed time points. FIG. 44 shows delivery of a therapeutic amount of SN-38 to effectively kill cancer cells (OE33, oesophageal cancer) in vitro. The concentration of SN-38 can be either lower or higher than the $IC_{50}$ value such that a similar curve can be created using force and/or strain, rather than, or in addition to, concentration. Hence, the number of dead cells coincides with (a) the amount of strain applied, and (b) the time allowed for release. As shown in FIG. 44, the inventors have demonstrated strain-dependent release of SN-38, a hydrophobic drug molecule. Because SN-38 is a toxic chemotherapeutic drug, the amount of SN-38 released correlates with cell viability. The inventors were able to deliver an efficacious amount of SN-38 to change the cell viability, as determined by MTS Assay. (FIG. 44)

Example 34

Incorporation of a Growth Factor (TNF-α) into a Mechanoresponsive Drug Delivery Device Tumor Necrosis Factor alpha (TNF-α, Sigma-Aldrich, 10 µg) was dissolved in 250 µL nanopure water and 50 µL of this solution was dispensed on top of an absorbent hydroentangled cellulose and polyester mesh, and soaked into the mesh. The mesh was allowed to air-dry at room temperature overnight to evaporate the solvent, leaving behind the growth factor. The surface was then coated with a hydrophobic or superhydrophobic barrier comprised of polymer particles or fiber(s), as described in Examples 1-7 above, and subsequently characterized as described in Examples 8 and 9 above.

Example 35

Quantification of Growth Factor (TNF-α) Release from Mechanoresponsive Drug Delivery Device The amount of TNF-α released from the drug delivery system into the surrounding aqueous environment can be quantified through cell viability assay with L929, WEHI 164, or WEHI 164-subclone 13. A standard curve is first created, and aliquots (sampled at different timepoints) from the release medium with unknown TNF-α concentrations were determined from this standard curve. The concentration values were then converted to amount (mass) of TNF-α released by multiplying the concentration by the total volume of solution into which the agent released. The amount of TNF-α actually released was then divided by the amount of TNF-α initially loaded into the device, to get a percentage of TNF-α released as a function of time.

Example 36

Modulating Release of Growth Factor (TNF-α) by Varying the Amount of Applied Strain A TNF-α-incorporated drug delivery device was fabricated in accordance with Examples 2 and 35 above. The coating was electrosprayed using a tip-to-collector distance of 10 cm. The ends of the material were placed between two pieces of foam tape and further secured by applying glue to the ends in contact with the foam tape. The ends were then placed between the grips of a stretch device and the sample length between the grips was recorded. A water bath was placed under the sample arms, and the drug delivery device was submerged beneath 120 mL of DMEM (cell media) containing 10% fetal bovine serum (FBS), and released under sterile conditions in a laminar flow hood. A magnetic stir bar was also added to the bath to ensure thorough mixing during the study. Testing a different strains were achieved by increasing travel distance equivalent to thirty percent of the initial sample length was reached (corresponding to 30% strain), or equivalent to the entire initial sample length was reached (corresponding to 100% strain). Once the device was stretched, aliquots of release medium were sampled at predetermined time points. The percentage of TNF-α released into the surrounding aqueous environment can be calculated from cell viability assays, as described in Example 35. Mechanoresponsive drug delivery systems were also placed on stretch device, but in this instance they were not stretched (0% strain) to serve as a control experiment. Release of the TNF-α is expected to be most rapid from devices subjected to 100% strain and more moderate from devices subjected to 30% strain. Devices not subjected to strain will not release appreciable amounts of TNF-α.

Example 37

Quantification of Collagen Content

Hydroxyproline is a major amino acid component of collagen, and thus a colormetric hydroyproline assay kit (Sigma-Aldrich) was used to detect the decrease in collagen production with increased delivery of TNF-α. Briefly, the preparation for the assay involves hydrolyzing cells with acid, followed by acid removal by vacuum oven. A mixture of Chloramine T, Oxidation Buffer, DMAB, Perchloric acid/Isopropanol Solution are added and the final signal is read at 570 nm with a plate reader. (FIG. 45)

Example 38

Modulating Release of TNF-α and Collagen Production by Varying Magnitude of Applied Strain with Dry Superhydrophobic Electrosprayed Coating TNF-α is known to inhibit synthesis of type I collagen in fibroblasts (Mauviel et al, FEBS Lett 1988; 236: 47-52) (Mauviel et al, J Invest Dermatol 1991; 96: 243-9). Therefore, delivery of TNF-α to 3T3 fibroblasts would decrease collagen production and fibrosis. 20,000 3T3 fibroblasts were plated into each 96-well plate and TNF-α release aliquots were incubated over 24-72 hours. The hydroxyproline assay was conducted as described in Example 37 to determine cellular response to TNF-α delivery. (FIG. 46)

Example 39

Hydrophobic Electrosprayed Coatings Cannot Modulate Release

Dye-loaded hydroentangled cellulose/polyester meshes were unable to effectively prevent dye release in the absence of strain. Hydrophobic coatings were made by electrospraying poly(ε-caprolactone), as described in Example 1. However, they failed to contribute to the mechanoresponsive drug delivery device when compared to superhydrophobic electrosprayed coatings in Examples 17 and 21. The dye release rate with the hydrophobic coating is not significant from the dye release rate from a superhydrophobic coating under 100% strain. (FIG. 47)

Example 40

Influence of Loading Rate on Release

As shown in Examples 17-21, 28, 29, and 32, the mechanoresponsive drug delivery device was extended at a constant rate of 2 mm/s with the tensile tester machine. In accordance to tests in Example 21, we determined whether the change in loading rate from 2 mm/s to 0.4 mm/s and 10 mm/s affected the dye release kinetics. At 100% strain, that is, when the device was extended to twice its original length, there was no appreciable difference in release. (FIG. 48)

Example 41

Superhydrophobic Coating Thickness Modulates Release Kinetics

The coating thickness of the superhydrophobic electrospray on the mechanoresponsive drug delivery device was increased from 100 μm to 300 μm. As in Example 21, the release kinetics of the dye was quantified at various strains. The thicker coating lead to a significantly slower dye release rate than the thinner coating. (FIG. 49)

Example 42

Determination of Critical Strain Energy Release Rate ($G_{Ic}$) and Plane-Strain Fracture Toughness ($K_{Ic}$) for Superhydrophobic Coating Mechanical analysis in accordance with ASTM Standard D 5049-99 with a polydimethylsiloxane (SYLGARD 184, Dow Corning) substrate analog of our system resulted in estimates of the plane-strain fracture toughness ($K_{Ic}$) and critical strain energy release rate ($G_{Ic}$) to be 44 kPa·m$^{1/2}$ and 7.61 N·mm$^{-1}$, respectively. $K_{Ic}$ was calculated from specifications for compact-tension specimens and $G_{Ic}$ is directly derived from the energy of the crack formation, integrating the force-displacement curve [up to $P_Q$, the intersection of the curve and 0.95*slope of the linear portion].

The modulus of the electrosprayed coating was determined to be 0.35 MPa (accounting for Poisson's ratio) from the relation: $E=K_{Ic}^2(1-\upsilon^2)/G_{Ic}$, after normalizing for the volume fraction of the electrosprayed coating in relation to the PDMS substrate. The $K_{Ic}$ and $G_{Ic}$ represent a lower limit of fracture resistance in terms of applied stress and strain, respectively, of the coating. Knowing these values and the stress magnitude at various strains (10% strain at 0.5 MPa, 30% strain at 1.1 MPa, 50% strain at 1.8 MPa, 100% strain at 3.2 MPa), the rate of release can be controlled. (FIGS. 50 and 51)

Example 43

Electrospinning Hydrophobic Elastic Polyurethane Meshes

Polyurethane (Selectophore, Sigma-Aldrich) was dissolved in 12.5% w/v hexafluoroisopropanol (HFIP). The solution was electrospun at 5 mL/hr, 10 mL/hr, and varying tip-to-collector distances to create a hydrophobic elastic core material for the mechanoresponsive drug delivery device. Note the increase in contact angle of 0° for the hydroentangled cellulose/polyester core to 125-128° for electrospun polyurethane.

TABLE 1

Electrospinning parameters for polyurethane meshes.

| Flow Rate | Advancing Contact Angle | Receding Contact Angle |
|---|---|---|
| 5 mL/hr | 128.2 +/− 2.5° | 112.5 +/− 6.6 |
| 10 mL/hr | 125.5 +/− 1.7° | 98.7 +/− 7.1 |

Contact angles were calculated as shown in Examples 1-2, 4, 8.

Example 44

Mechanical Properties of Electrospun Polyurethane Meshes

Samples of electrospun polyurethane meshes were tested with the tensile tester machine (Instron 5848 Microtester). The ends of the material were placed between two pieces of foam tape and further secured by applying glue to the ends in contact with the foam tape. The ends were then placed between the grips of a tensile tester machine and the sample length between the grips was recorded. The Instron software was then programmed to extend the sample arms at a constant rate of 2 mm/s until a travel distance equivalent to the initial sample length was reached (corresponding to 100% strain). Young's modulus (E) was calculated from the slope of strain (displacement/original length) vs strain (force/cross-sectional area). Elongation was calculated as the length necessary to break the material/original length, and the ultimate tensile strength is the highest stress value when the sample is under tension until breaking. The relaxation time was determined by first increasing strain to 100% (twice the original length) and determining the decrease in force while strain is held constant. (FIGS. 53 and 54)

TABLE 2

Mechanical properties of electrospun polyurethane meshes as a core material compared to hydroentangled cellulose/polyester mesh.

| Material Composition | Fiber Orientation | E (+) [kPa] | E (−) [kPa] | Elongation (mm/mm) | Ultimate Tensile Strength (kPa) | Relaxation Time (τ, s) at 100% strain |
|---|---|---|---|---|---|---|
| Polyurethane 5 mL/hr | Parallel | 618.43 +/− 43.71 | 538.85 +/− 12.30 | 3.34 | 2100 | 7.552 |
|  | Perpendicular | 307.51 +/− 32.50 | 252.27 +/− 11.06 | 4.48 | 1649 | 6.877 |
| Polyurethane 10 mL/hr | Parallel | 599.39 +/− 15.51 | 545.38 +/− 23.59 | 2.47 | 1564 | 7.054 |
|  | Perpendicular | 388.49 +/− 10.88 | 341.51 +/− 14.73 | 2.73 | 1649 | 7.186 |
| Hydroentangled cellulose/polyester mesh | Perpendicular | 3238.96 | N/A | 1.03 | 3234 | 6.058 |

Example 45

Incorporation of a Hydrophilic Dye into Hydrophobic Elastic Polyurethane Meshes

The hydrophobic polyurethane meshes were wet with ethanol or methanol and slightly air-dried for 1 minute. Hydrophilic dye was pipetted and soaked into the entire mesh, turning the entirety of the mesh green. The mesh was allowed to dry at room temperature to evaporate the solvent. The hydrophilic dye loading is approximately 1 µL/0.364 mm$^2$ of the polyurethane mesh as compared to 1 µL/0.288 mm$^2$ for the hydroentangled cellulose/polyester mesh. (FIG. 54)

Rhodamine and other alcohol-soluble agents can also be incorporated into the polyurethane system by pipetting the dye and solvent solution onto the substrate. The solution was allowed to dry at room temperature to evaporate the solvent. (FIG. 55)

Example 46

Electrospraying a Superhydrophobic Coating on Hydrophobic Elastic Substrate

Poly(glycerol monostearate-co-ε-caprolactone) [PGC-C18] and poly(s-caprolactone) were dissolved in 1:1 ratio in chloroform to make a 10% (w/v) solution. This solution was electrosprayed (flow rate of 3-5 mL/hr, a voltage of 10-25 kV, and distance of 10-15 cm) to create a layer or barrier comprised of discrete or interconnected polymer particles. The particles collected onto an elastic polyurethane mesh, which was attached to a grounded target through conductive copper tape. After one side had been treated, the meshes were gently removed from the copper tape, turned over, and placed back on the copper tape such that the untreated side could then be coated. The resulting surface of the polyurethane mesh was altered from the deposition of particles, such that rather than absorbing a water drop on its surface, it became extremely water-repellent, with water contact angles greater than or equal to 150 degrees. (FIG. 56-58)

The superhydrophobic coating can also be imparted on a clear thin polyurethane substrate. Under tension, the crack patterns are similar to those in Examples 22 and 26.

The superhydrophobic coating can also be imparted on a porous polyurethane substrate through electrospraying.

Example 47

Release of Protein From Hydrophobic Substrate

A porous hydrophobic polyurethane substrate with loaded with fluorescein isothiocyanate-labeled bovine serum albumin (FITC-BSA) in accordance with Example 12 above. The FITC-BSA-loaded substrate was submerged in phosphate-buffered saline (PBS) with 10% serum (fetal bovine serum) with a magnetic stir bar to ensure thorough mixing during the study. Release of FITC-BSA was determined as shown in Example 13. (FIG. 59)

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A drug-delivery device comprising a non-superhydrophobic core and a superhydrophobic coating layer on at least one surface of the core, wherein the core comprises an agent distributed in a matrix material, and wherein tensile strengths of the core and the coating layer differ by at least 10%, wherein the coating layer has a lower compressive toughness, a lower compressive strength and a lower compressive elastic modulus relative to the core, wherein the coating layer has an average surface roughness (Ra) of at least 90 nm, and wherein the coating layer does not comprise a drug, and wherein the coating layer has a compressive elastic modulus that is 90% or lower of the compressive elastic modulus of the core, a compressive toughness that is 90% or lower of the compressive toughness of the core, and a compressive strength that is 90% or lower of the compressive strength of the core.

2. The drug-delivery device of claim 1, wherein the coating layer has a contact angle of 155° or higher.

3. The drug-delivery device of claim 1, wherein the coating layer has a compressive elastic modulus in a range from about 0.01 MPa to about 1 MPa.

4. The drug-delivery device of claim 1, wherein the coating layer is composed of particles.

5. The drug-delivery device of claim 1, wherein the coating layer is multilayered.

6. The drug-delivery device of claim 1, wherein the coating layer comprises a material selected from the group consisting of polyesters, polycarbonates, polyamides, polyethers, polyanhydrides, polyacrylates, copolymers thereof, and any mixtures thereof.

7. The drug-delivery device of claim 1, wherein the coating layer comprises a material selected from the group consisting of poly(caprolactone), poly(lactide-co-glycolide), poly(glycerol monostearate-co-caprolatone), and any mixtures thereof.

8. The drug-delivery device of claim 1, wherein the core is in the form of a film, a particle, a mesh, a fiber, a gel, a hydrogel, a foam, a mat, a non-woven mat, or any combinations thereof.

9. The drug-delivery device of claim 1, wherein the matrix material of the core is comprised of an absorbent material.

10. The drug-delivery device of claim 1, wherein the matrix material of the core comprises a material selected from the group consisting of polyesters, polycarbonates, polyamides, polyethers, polyanhydrides, polyacrylates, polyurethanes, and mixture or copolymers thereof.

11. The drug-delivery device of claim 1, wherein the matrix material of the core comprises a material selected from the group consisting of poly(caprolactone), poly(glycerol monostearate-co-caprolactone), polyurethane, polyurea, collagen, hyaluronic acid, dextran, alginate, fibrin, alginate, PDMS, cellulose, hydroentangled cellulose, polyester mesh, and mixture or copolymers thereof.

12. The drug-delivery device of claim 1, wherein the core comprises a multilayered structure.

13. The drug-delivery device of claim 1, wherein the drug-delivery device is in form of an implant or an implantable device.

14. The drug-delivery device of claim 1, wherein the drug-delivery device is a balloon catheter, a stent, part of a cell scaffold, an implantable material used in a tissue expander or a gastric band.

15. The drug-delivery device of claim 1, wherein the agent is selected from the group consisting of small organic or inorganic molecules, peptides, peptide analogs and derivatives, peptidomimetics, proteins, antibodies, antigen or epitope binding fragments of antibodies, nucleic acids, nucleic acid analogs and derivatives, an extract made from biological materials, and any combinations thereof.

16. The drug-delivery device of claim 1, wherein the agent is selected from the group consisting of chemotherapeutic agents, radiosensitizers, receptor inhibitors and agonists, anti-neoplastic agents; immune modulators, cytokines, growth factors, or steroids with or without the co-incorporation of tumor or pathogen antigens, anesthetic agents; antibiotics, imaging agents, and any combinations thereof.

* * * * *